United States Patent
Wu et al.

(10) Patent No.: US 11,597,969 B2
(45) Date of Patent: Mar. 7, 2023

(54) CYCLOOCTATETRAENE CONTAINING DYES AND COMPOSITIONS

(71) Applicant: Illumina Cambridge Limited, Cambridge (GB)

(72) Inventors: Xiaolin Wu, Cambridge (GB); Xiaohai Liu, Cambridge (GB); Nikolai Nikolaevich Romanov, Cambridge (GB); Antoine Francais, Cambridge (GB); Patrick McCauley, Cambridge (GB); Michael Callingham, Cambridge (GB); Carole Anastasi, Cambridge (GB)

(73) Assignee: Illumina Cambridge Limited, Cambridge (GB)

( * ) Notice: Subject to any disclaimer, the term of this patent is extended or adjusted under 35 U.S.C. 154(b) by 121 days.

(21) Appl. No.: 17/103,169

(22) Filed: Nov. 24, 2020

(65) Prior Publication Data
US 2021/0155983 A1    May 27, 2021

Related U.S. Application Data

(60) Provisional application No. 62/941,583, filed on Nov. 27, 2019.

(51) Int. Cl.
  *C12Q 1/68* (2018.01)
  *C09B 57/02* (2006.01)
  *C12Q 1/6869* (2018.01)

(52) U.S. Cl.
  CPC .......... *C12Q 1/6869* (2013.01); *C09B 57/02* (2013.01)

(58) Field of Classification Search
  CPC ........................... C12Q 1/6869; C09B 57/02
  See application file for complete search history.

(56) References Cited

U.S. PATENT DOCUMENTS

| | | |
|---|---|---|
| 5,302,509 A | 4/1994 | Cheeseman |
| 6,172,218 B1 | 1/2001 | Brenner |
| 6,465,178 B2 | 10/2002 | Chappa et al. |
| 7,998,717 B2 | 8/2011 | Eid et al. |
| 8,388,982 B2 | 3/2013 | Kong et al. |
| 8,834,847 B2 | 9/2014 | Yue et al. |
| 9,115,353 B2 | 8/2015 | Klausing et al. |
| 9,217,178 B2 | 12/2015 | Fedurco et al. |
| 9,303,290 B2 | 4/2016 | Fedurco |
| 9,637,782 B2 | 5/2017 | Shen et al. |
| 9,856,529 B2 | 1/2018 | Klausing |
| 9,970,055 B2 | 5/2018 | Fedurco |
| 10,106,851 B2 | 10/2018 | Klausing |
| 10,214,768 B2 | 2/2019 | Romanov |
| 2010/0181535 A1 | 7/2010 | Tinnefeld et al. |
| 2014/0079923 A1 | 3/2014 | George et al. |
| 2014/0080721 A1 | 3/2014 | Klausing |
| 2015/0011731 A1 | 1/2015 | Blanchard et al. |
| 2016/0040225 A1 | 2/2016 | Wu et al. |
| 2018/0094140 A1 | 4/2018 | Romanov |
| 2018/0201981 A1 | 7/2018 | Romanov |
| 2019/0017111 A1 | 1/2019 | Cressina et al. |
| 2020/0190576 A1 | 6/2020 | Gatti-Lafranconi |
| 2020/0190659 A1 | 6/2020 | Gatti-Lafranconi |
| 2020/0216891 A1 | 7/2020 | Francais et al. |
| 2020/0277529 A1 | 9/2020 | Romanov et al. |
| 2020/0277670 A1 | 9/2020 | Romanov et al. |

FOREIGN PATENT DOCUMENTS

| | | |
|---|---|---|
| WO | WO 98/44151 | 10/1998 |
| WO | WO 00/006770 | 2/2000 |
| WO | WO 00/18957 | 4/2000 |
| WO | WO 00/31148 | 6/2000 |
| WO | WO 00/53812 | 9/2000 |
| WO | WO 01/01143 | 1/2001 |
| WO | WO 01/057248 | 8/2001 |
| WO | WO 02/12566 | 2/2002 |
| WO | WO 03/014392 | 2/2003 |
| WO | WO 04/018493 | 3/2004 |
| WO | WO 04/018497 | 3/2004 |
| WO | WO 05/024010 | 3/2005 |
| WO | WO 05/047301 | 5/2005 |
| WO | WO 05/065814 | 7/2005 |
| WO | WO 06/120433 | 11/2006 |
| WO | WO 07/020457 | 2/2007 |
| WO | WO 2013/109859 | 7/2013 |
| WO | WO 14/139596 | 9/2014 |

OTHER PUBLICATIONS

U.S. Appl. No. 63/057,758, filed Jul. 28, 2020, Romanov et al.
Altman et al., 2012, Cyanine fluorophore derivatives with enhanced photostability, Nat. Methods, 9(1):68-71.
Cope et al., 1952, Cyclic Polyolefins. XIX. Chloro- and bromocyclooctatetraenes, J. Am. Chem. Soc., 74:168-172.
Garcia-Lopez et al., 2016, Synthesis and photostability of unimolecular submersible nanomachines: toward single-molecule tracking in solution, Org. Lett, 18:2343-2346.
Margulies, Sep. 15, 2005, Genome sequencing in microfabricated high-density picolitre reactors, Nature, 437:376-380.
Scheit, K. H. (1980). *Nucleotide analogs: Synthesis and biological function.* New York: John Wiley & Sons, TOC, 5 pages.
Schendure et al., Sep. 9, 2005, Accurate multiplex plogy sequencing of an evolved bacterial genome, Science, 309(5741):1728-1732.
Schwechheimer et al., 2018, A new structure-activity relationship for cyanine dyes to improve photostability and fluorescence properties for live cell imaging, Chemical Science, 9:6557-6563.

(Continued)

*Primary Examiner* — Jezia Riley

(74) *Attorney, Agent, or Firm* — Knobbe Martens Olson & Bear LLP

(57) ABSTRACT

Embodiments of the present disclosure relate to cyclooctatetraene containing dyes and their uses as fluorescent labels. Also provided are composition containing cyclooctatetraene. The dyes and compositions may be used in various biological applications, such as nucleic acid sequencing.

20 Claims, 10 Drawing Sheets

(56) References Cited

OTHER PUBLICATIONS

Strome et al., Sep. 1971, Triplet quenching and continuous laser action in three fluorescein dyes, Optics Communications, 4(1):58-59.
Uhlman et al., Jun. 1990, Antisense oligonucleotides: a new therapeutic principle, Chemical Reviews, 90(4):543-584.
Zheng et al., 2014, Ultra-stable organic fluorophores for single-molecule research, Chem. Soc. Rev., 43:1044-1056.
Zheng et al., 2017, Electronic tuning of self-healing fluorophores for live-cell and single-molecule imaging, Chem. Sci., 8:755-762.
Houston et al., Jun. 26, 2019, The cubane paradigm in bioactive molecular discovery: further scope, limitations and the cyclooctatetraene complement, Organic & Biomolecular Chemistry, 17(28):6790-6798.
Ostapko et al., Jun. 25, 2020, Towards more photostable, brighter, and less phototoxic chromophores: synthesis and properties of porphyrins functionalized with cyclooctatetraene, Chemistry a European Journal, 26(70):16666-16675.
Pati et al., Sep. 10, 2020, Tuning the Baird aromatic triplet-state energy of cyclooctatetraene to maximize the self-healing mechanism in organic fluorophores, Proceedings of the National Academy of Sciences, 117(39):24305-24315.
Xing et al., May 23, 2019, Determining the necessity of phenyl ring [pi]-character in warfarin, 29(15):1954-1956.
Zheng et al., Dec. 2, 2013, The contribution of reactive oxygen species to the photobleaching or organic fluorophores, Photochemistry and Photobiology, 90(2):448-454.
International Search Report and Written Opinion dated Apr. 29, 2021 in application No. PCT/EP2020/081570.

CYCLOOCTATETRAENE CONTAINING DYES AND COMPOSITIONS

INCORPORATION BY REFERENCE TO PRIORITY APPLICATION

The present application claims the benefit of priority to U.S. Provisional Application No. 62/941,583, filed Nov. 27, 2019, which is hereby incorporated by reference in its entirety.

FIELD

The present disclosure relates to fluorescent compounds and compositions containing cyclooctatetraene or optionally substituted derivatives thereof. In particular, the fluorescent compounds and compositions may be used in various biological applications, such as nucleic acid sequencing applications.

BACKGROUND

Background

Non-radioactive detection of nucleic acids utilizing fluorescent labels is an important technology in molecular biology. Many procedures employed in recombinant DNA technology previously relied on the use of nucleotides or polynucleotides radioactively labeled with, for example $^{32}$P. Radioactive compounds permit sensitive detection of nucleic acids and other molecules of interest. However, there are serious limitations in the use of radioactive isotopes such as their expense, limited shelf life and more importantly safety considerations Eliminating the need for radioactive labels enhances safety whilst reducing the environmental impact and costs associated with, for example, reagent disposal. Methods amenable to non-radioactive fluorescent detection include by way of non-limiting example, automated DNA sequencing, hybridization methods, real-time detection of polymerase-chain-reaction products and immunoassays.

For many applications it is desirable to employ multiple spectrally distinguishable fluorescent labels in order to achieve independent detection of a plurality of spatially overlapping analytes. In such multiplex methods the number of reaction vessels may be reduced to simplify experimental protocols and facilitate the production of application-specific reagent kits. In multi-color automated DNA sequencing systems for example, multiplex fluorescent detection allows for the analysis of multiple nucleotide bases in a single electrophoresis lane, thereby increasing throughput over single-color methods, and reducing uncertainties associated with inter-lane electrophoretic mobility variations.

However, multiplex fluorescent detection can be problematic and there are a number of important factors that may constrain selection of appropriate fluorescent labels. First, it may be difficult to find dye compounds with suitably-resolved absorption and emission spectra in a given application. In addition, when several fluorescent dyes are used together, generating fluorescence signals in distinguishable spectral regions by simultaneous excitation may be complicated because absorption bands of the dyes are usually widely separated, so it may be difficult to achieve comparable fluorescence excitation efficiencies even for two dyes. Another consideration of particular importance to molecular biology methods is the extent to which the fluorescent dyes must be compatible with reagent chemistries such as, for example, DNA synthesis solvents and reagents, buffers, polymerase enzymes, and ligase enzymes. Further, since many excitation methods use high power light sources like lasers, the fluorescent dyes must be sufficiently photo-stable to withstand multiple excitation.

For high-accuracy fluorescence identification of nucleobases, scanning of fluorescently labeled nucleotides under intensive expose to light is typically involved. Extensive laser irradiation, however, may bleach fluorescent dyes and/or damage nucleotide samples in solution/on flow-cell surface or those to which the fluorescent dyes are conjugated. Such expose to light may also cause DNA sample damage. Thus, there is a need particularly in multiplex fluorescent DNA sequencing to protect fluorescent dyes from photo-bleaching and nucleotides from photo induced damages. The type and extent of photo-bleaching and photo-damages may vary depending on, for example, compounds chemical structure and some their physical-chemical properties like redox potential, excitation spectra of particular bio-label, intensity of particular light source irradiation, and time of exposure in particular measurement. Since lower wavelength light sources are delivering higher energy photons, blue LED/laser having short (400-500 nm) wavelength emission (e.g., 450-460 nm) are more likely to cause photo-bleaching of dyes and associated with light DNA damage.

Performing fluorescent detection steps in an array context, such as sequencing by synthesis, can cause fluorescence signal intensity loss. The possible mechanisms that underlie this signal loss are numerous and can include cleavage of individual nucleic acid units from the solid support. There are also a number of chemical pathways by which nucleic acid damage can occur during irradiation in fluorescence detection. For example, it has been indicated that exposure to ultraviolet (UV) radiation can cause DNA damage via the direct photochemical [2+2] photocycloaddition reaction of thymine or cytosine to provide cyclobutane containing fused pyrimidine dimers, such as TT, TC, and CC. Such direct photocycloaddition reactions can occur in the UV B and UV C regions which extend from about 100 nm to about 315 nm. In the UV A region through a portion of the visible region, spanning from about 315 nm to about 500 nm, a complex mixture of indirect mechanisms can also cause DNA damage through photosensitization of other components. Such indirect mechanisms can result oxidative DNA modification via interaction with different light induced reactive species, for example, Reactive Oxygen Species (ROS) such as singlet oxygen, superoxide anion, and hydroxyl radical. Finally, it also has also known that quite a few ROS are generated by interaction of dye molecules in an excited state with oxygen molecules. Any combination of direct or indirect nucleic acid damage due to various reactions observed can be the underlying cause of fluorescence signal intensity loss observed in the array context.

Antioxidants, radical scavengers, triplet eliminators and different other compounds like Triplet State Quenchers (TSQ) have attracted attention due to their potential to mitigate photo-bleaching of fluorophores under high irradiance even in the presence of oxygen (See, for example, U.S. Publication No. 2010/0181535A1). Most intensively such additives and their conjugates were explored for "Green" and "Red" cyanine dyes (See, for example, U.S. Publication No. 2015/0011731A1). However, there still exists a need for library of high-performance fluorescent bio-labels to be expanded further into the region of lower excitation wavelengths (e.g., 400-500 nm) where light induced DNA damage is the most pronounced. In addition, there is a need to further reduce fluorescent signal intensity loss for applications in sequencing by synthesis to facilitate sequencing of long nucleotide sequences, including sequences of 50, 75, 100, 200, and 500 nucleotides or more. Described herein are fluorescent compounds and compositions containing cyclooctatetraene (COT) or optionally substituted derivatives and derivatives thereof suitable for nucleic acid sequencing.

SUMMARY

Described herein are fluorescent compounds containing covalently bonded cyclooctatetraene or derivatives thereof and compositions containing cyclooctatetraene or derivatives thereof, the methods of preparation and uses in biological applications. Particularly, when used in nucleic acid sequencing applications, such fluorescent compounds and compositions can protect or mitigate against light induced fluorescent signal lost initiated or related to DNA and/or nucleotides photo-damages and photo-bleaching of the fluorescent labeling compounds.

Some aspect of the present disclosure relates to a fluorescent compound comprising a moiety covalently attached thereto, and the moiety could change population/occupancy of an excited state(s) of light absorbing molecules and may function as a photo-protecting group. In certain embodiments, the photo-protecting moiety may comprise an optionally substituted cyclooctatetraene moiety having the structure of formula (I):

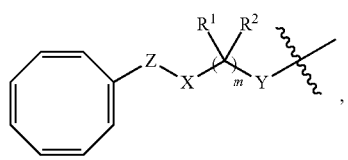
(I)

wherein:
each of $R^1$ and $R^2$ are each independently selected from the group consisting of H, hydroxyl, halogen, azido, thiol, nitro, cyano, optionally substituted amino, carboxyl, —C(O)OR$^5$, —C(O)NR$^6$R$^7$, optionally substituted alkyl, optionally substituted alkoxy, optionally substituted haloalkyl, optionally substituted haloalkoxy, optionally substituted alkenyl, optionally substituted alkynyl, optionally substituted aryl, optionally substituted aralkyl, optionally substituted carbocyclyl, optionally substituted heteroaryl, and optionally substituted heterocyclyl;

X and Y are each independently selected from the group consisting of a bond, —O—, —S—, —NR$^3$—, —C(=O)—, —C(=O)—O—, —C(=O)—NR$^4$—, —S(O)$_2$—, —NR$^3$—C(=O)—NR$^4$—, —NR$^3$—C(=S)—NR$^4$—, optionally substituted C$_{1-6}$ alkylene, and optionally substituted heteroalkylene;

Z is absent, optionally substituted C$_{2-6}$ alkenylene, or optionally substituted C$_{2-6}$ alkynylene;

each of $R^3$ and $R^4$ is independently H, optionally substituted C$_{1-6}$ alkyl, or optionally substituted C$_{6-10}$ aryl;

$R^5$ is optionally substituted C$_{1-6}$ alkyl, optionally substituted C$_{6-10}$ aryl, optionally substituted C$_{7-14}$ aralkyl, optionally substituted C$_{3-7}$ carbocyclyl, optionally substituted 5 to 10 membered heteroaryl, or optionally substituted 3 to 10 membered heterocyclyl;

each of $R^6$ and $R^7$ is independently H, optionally substituted C$_{1-6}$ alkyl, optionally substituted C$_{6-10}$ aryl, optionally substituted C$_{7-14}$ aralkyl, optionally substituted C$_{3-7}$ carbocyclyl, optionally substituted 5 to 10 membered heteroaryl, or optionally substituted 3 to 10 membered heterocyclyl;

the carbon atom to which $R^1$ and $R^2$ are attached in

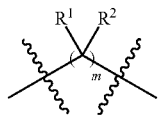

is optionally replaced with O, S, or N, provided that when said carbon atom is replaced with O or S, then $R^1$ and $R^2$ are both absent; when said carbon atom is replaced with N, then $R^2$ is absent; and m is an integral number between 0 and 10. In some embodiments, X and Y are not both a bond. In some further embodiments, the fluorescent compound is not a cyanine dye. In some further embodiments, the fluorescent compound is not a closed chain cyanine dye. In some further embodiments, the fluorescent compound may be excited by a light source having a wavelength between about 350 nm and about 500 nm, about 420 nm and about 480 nm, or about 450 nm and about 460 nm.

In some embodiments, the cyclooctatetraene moiety may comprise the structure of formula (Ia), (Ib), (Ic) or (Id):

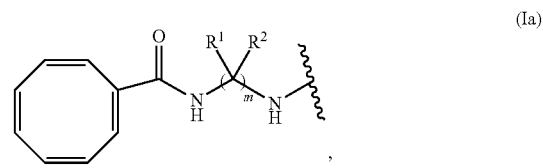
(Ia)

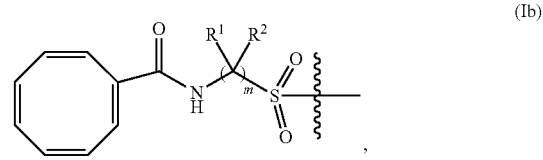
(Ib)

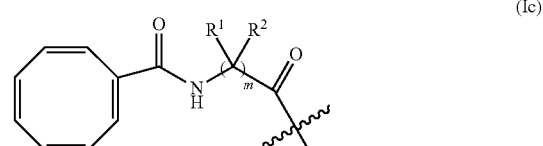
(Ic)

or

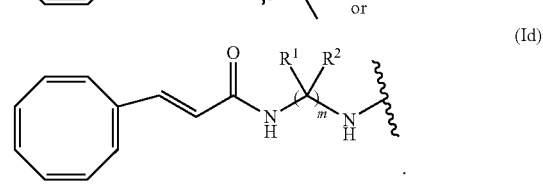
(Id)

Some aspect of the present disclosure relates to nucleotide or nucleoside labeled with a fluorescent compound having a COT moiety comprising the structure of formula (I), (Ia), (Ib), (Ic) or (Id) as described herein.

Some aspect of the present disclosure relates to a method of protecting a fluorescent dye from photo-bleaching, comprising covalently attaching the fluorescent dye to a COT moiety comprising of the structure of formula (I), (Ia), (Ib), (Ic) or (Id) as described herein. Some further aspect of the present disclosure relates to a method of protecting a nucleoside or nucleotide from light-induced degradation, comprising covalently attaching the nucleoside or nucleotide to a fluorescent compound comprising a COT moiety of the structure of formula (I), (Ia), (Ib), (Ic), or (Id) as described herein.

Some additional aspect of the present disclosure relates to a method of reducing or preventing light-induced degradation of nucleic acids during a nucleic acid sequencing reaction, comprising:

(a) incorporating a nucleotide into a copy polynucleotide strand complementary to at least a portion of a template polynucleotide strand, wherein the nucleotide comprises a 3' blocking group and is labeled with a fluorescent compound comprising the structure of formula (I), (Ia), (Ib), (Ic) or (Id) as described herein;

(b) detecting the identity of the nucleotide incorporated into the copy strand in the presence of a first buffer composition;

(c) chemically removing the label and the 3' blocking group from the nucleotide incorporated into the copy polynucleotide strand; and (d) washing the chemically removed label and the 3' blocking group away from the copy strand with a wash solution.

Some additional aspect of the present disclosure relates to a kit for use with a sequencing apparatus, comprising a plurality of chambers containing a plurality of compositions, wherein each chamber contains a single composition, wherein the plurality of compositions comprise: reagents for incorporating a nucleotide into a copy polynucleotide strand complementary to at least a portion of a template polynucleotide strand, wherein the nucleotide comprises a 3' blocking group and is labeled with a fluorescent compound comprising the structure of formula (I), (Ia), (Ib), (Ic) or (Id) as described herein; a buffer composition comprising at least one antioxidant; reagents for chemically removing a label and blocking moiety from the blocked, labeled nucleotide incorporated into the copy strand; and a wash solution.

Some aspects of the present disclosure relates to a composition for preventing or reducing photobleaching of a fluorescent dye, comprising cyclooctatetraene or an optionally substituted derivative thereof, and one or more antioxidants selected from the group consisting of taxifolin, quercetin, allyl thiourea, dimethyl thiourea, silibinin, and trolox, and optionally substituted derivatives and combinations thereof. In some further embodiment, the composition comprises cyclooctatetraene and quercetin, and optionally substituted derivatives and combinations thereof.

Some aspect of the present disclosure relates to a method of protecting a fluorescent dye from photobleaching, comprising contacting the fluorescent dye with a composition containing cyclooctatetraene as described herein. Some further aspects relate to a method of protecting a labeled nucleoside or nucleotide from light-induced degradation, comprising contacting the labeled nucleoside or nucleotide with the composition described herein.

Some aspect of the present disclosure relates to a method of reducing or preventing light-induced degradation of nucleic acids during a nucleic acid sequencing reaction, comprising:

(a) incorporating a nucleotide into a copy polynucleotide strand complementary to at least a portion of a template polynucleotide strand, wherein the nucleotide comprises a label and a 3' blocking group;

(b) detecting the identity of the nucleotide incorporated into the copy strand in the presence of a first buffer composition;

(c) chemically removing the label and the 3' blocking group from the nucleotide incorporated into the copy polynucleotide strand; and (d) washing the chemically removed label and the 3' blocking group away from the copy strand with a wash solution;

wherein the first buffer composition comprises cyclooctatetraene or an optionally substituted derivative thereof, and one or more antioxidants selected from the group consisting of taxifolin, quercetin, allyl thiourea, dimethyl thiourea, silibinin, and trolox, and optionally substituted derivatives and combinations thereof.

Some additional aspect of the present disclosure relates to a kit for use with a sequencing apparatus, comprising a plurality of chambers containing a plurality of compositions, wherein each chamber contains a single composition, wherein the plurality of compositions comprise: reagents for incorporating a 3' blocked, labeled nucleotide into a copy polynucleotide strand complementary to at least a portion of a template polynucleotide strand; a buffer composition comprising a composition containing cyclooctatetraene as described herein; reagents for chemically removing a label and blocking moiety from the blocked, labeled nucleotide incorporated into the copy strand; and a wash solution.

DETAILED DESCRIPTION

Figure 1:
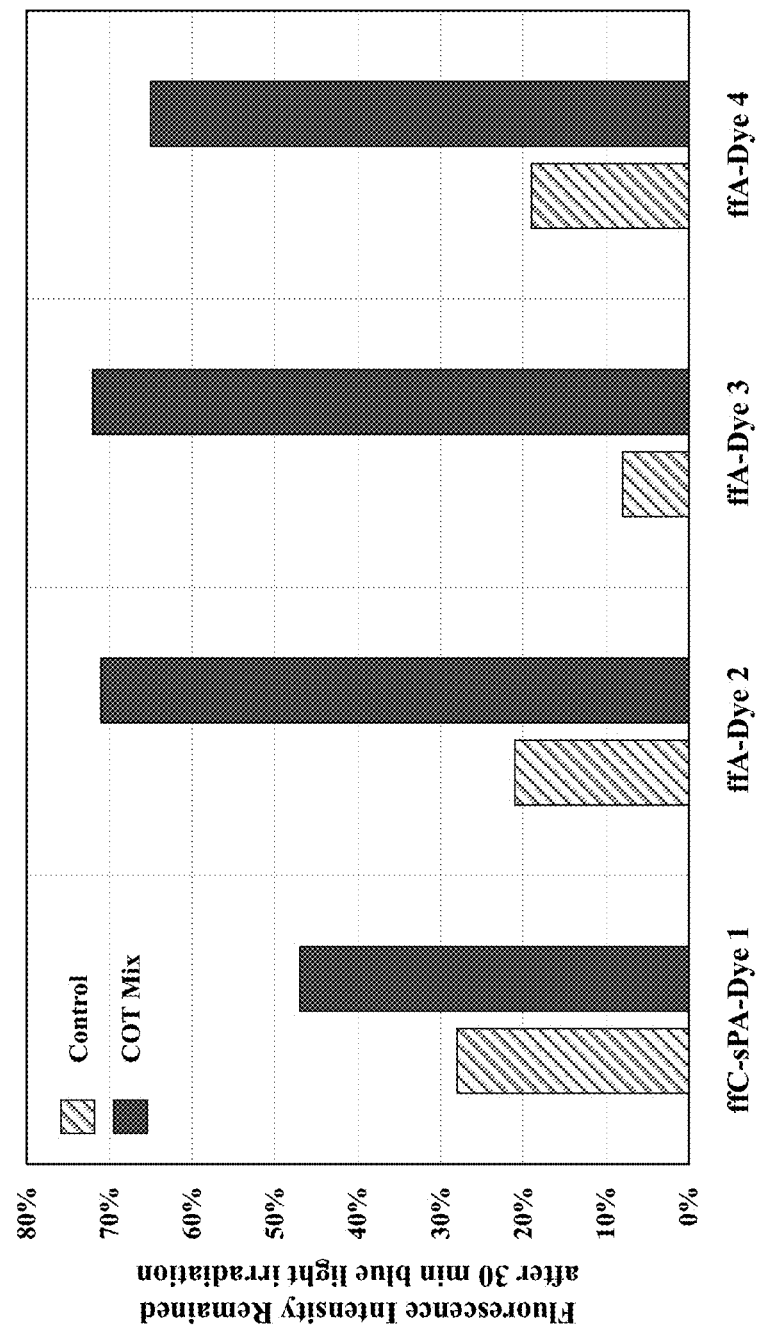
FIG. 1 illustrates the photobleaching rate of four fluorescent dyes after 30 minutes of blue LED light irradiation in a standard detection solution as compared to a solution containing cyclooctatetraene and quercetin as described herein.

The present disclosure relates to dye compounds and their application as fluorescent labels for biomolecules. In particular, disclosed herein are fluorescent compounds covalently bonded to a photo-protecting small organic molecule. Also enclosed are compositions containing such small organic molecule. The conjugates of these small organic molecule with the fluorescent compounds possess higher stability to light induced degradation. For example, such small organic molecule may be a triplet state eliminator, for example, compounds like 1,3,5-7-cyclooctatetraene or optionally substituted derivatives thereof may change population/occupancy of an excited state of the fluorescent compounds. The fluorescent compounds and compositions described herein may be used in nucleic acid sequencing applications.

Embodiments described herein relate to fluorescent compounds comprising a photo-protecting moiety covalently attached thereto. The photo-protecting moiety may comprise an optionally substituted cyclooctatetraene (COT) moiety. The COT moiety may comprise the structure of Formula (I), (Ia), (Ib), (Ic) or (Id) as described herein. These fluorescent compounds may be used as labels for nucleic acid sequencing applications, for example, as nucleotide labels during sequencing-by-synthesis.

Further embodiments described herein relate to compositions for using during the detecting or scanning step of the sequencing run where the labeled nucleotide is exposed to a light source, in particular to irradiation from a blue LED or laser. The composition comprises cyclooctatetraene one or more antioxidants. For example, the one or more antioxidants may be selected from the group comprising taxifolin, quercetin, allyl thiourea, dimethyl thiourea, silibinin, cyclooctatetraene, and trolox, and optionally substituted derivatives and combinations thereof. The composition may further include ascorbic acid or a salt thereof, for example, sodium ascorbate.

As described in details below, the COT containing fluorescent compounds and the compositions described herein may enhanced dye photostability when exposed to a light source irradiation, in particular to the blue light with wavelength between about 400 nm to about 500 nm (e.g., about 450 nm to about 460 nm). These compounds and composition also reduce or prevent DNA damage during sequencing runs.

Definition

The section headings used herein are for organizational purposes only and are not to be construed as limiting the subject matter described.

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "$C_a$-$C_b$" or "$C_{a-b}$" in which "a" and "b" are integers refer to the number of carbon atoms in an alkyl, alkenyl or alkynyl group, or the number of ring atoms of a cycloalkyl or aryl group. That is, the alkyl, the alkenyl, the alkynyl, the ring of the cycloalkyl, and ring of the aryl can contain from "a" to "b", inclusive, carbon atoms. For example, a "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, alkenyl, alkynyl, cycloalkyl, or aryl group, the broadest range described in these definitions is to be assumed. As used herein, the term "$C_{1-6}$" includes $C_1$, $C_2$, $C_3$, $C_4$, $C_5$ and $C_6$, and a range defined by any of the two numbers. For example, $C_{1-6}$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_2$-$C_6$ alkenyl includes $C_2$, $C_3$, $C_4$, $C_5$ and $C_6$ alkenyl, $C_2$-$C_5$ alkenyl, $C_3$-$C_4$ alkenyl, etc.; and $C_2$-$C_6$ alkynyl includes $C_2$, $C_3$, $C_4$, $C_5$ and $C_6$ alkynyl, $C_2$-$C_5$ alkynyl, $C_3$-$C_4$ alkynyl, etc. $C_3$-$C_8$ cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 6 carbon atoms. The alkyl group may be designated as "$C_{1-4}$ alkyl" or similar designations. By way of example only, "$C_{1-6}$ alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 6 carbon atoms. The alkenyl group may be designated as "$C_{2-6}$ alkenyl" or similar designations. By way of example only, "$C_{2-6}$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 6 carbon atoms. The alkynyl group may be designated as "$C_{2-6}$ alkynyl" or similar designations. By way of example only, "$C_{2-6}$ alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 6 carbon atoms. The heteroalkyl group may be designated as "$C_{1-6}$ heteroalkyl" or similar designations. The heteroalkyl group may contain one or more heteroatoms. By way of example only, "$C_{4-6}$ heteroalkyl" indicates that there are four to six carbon atoms in the heteroalkyl chain and additionally one or more heteroatoms in the backbone of the chain.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, an "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-6}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, a "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-6}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and Spiro[4.4] nonanyl.

As used herein, "cycloalkyl" means a fully saturated carbocyclyl ring or ring system. Examples include cyclopropyl, cyclobutyl, cyclopentyl, and cyclohexyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, a "cyano" group refers to a "—CN" group.

As used herein, a "carboxyl" group refers to a "—C(=O)OH" group.

As used herein, an "azido" group refers to a "—N$_3$" group.

As used herein, an "thiol" group refers to a "—SW" group, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, $C_{7-14}$ aralkyl, 5-10 membered heteroaryl, or 3-10 membered heterocyclyl, as defined herein.

As used herein, an "amino" group refers to —NH$_2$. An "optionally substituted amino" refers to —NH$_2$ where one or both hydrogen is replaced with $C_{1-6}$ alkyl, $C_{2-6}$ alkenyl, $C_{2-6}$ alkynyl, $C_{3-7}$ carbocyclyl, $C_{6-10}$ aryl, $C_{7-14}$ aralkyl, 5-10 membered heteroaryl, or 3-10 membered heterocyclyl, as defined herein.

As used herein, an "aminoalkyl" group refers to an amino group connected via an alkylene group.

As used herein, an "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

As used herein, a "C-carboxy" group refers to a "—C(=O)OR" group in which R is selected from the group consisting of hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes carboxyl (i.e., —C(=O)OH).

As used herein, a "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

As used herein, a "sulfino" group refers to a "—S(=O)OH" group.

A "sulfo" group refers to a "—S(=O)$_2$OH" or "—SO$_3$H" group.

A "sulfonate" group refers to a "—SO$_3^-$" group.

As used herein, a "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

As used herein, an "N-sulfonamido" group refers to a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

As used herein, a "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

As used herein, an "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-carbamyl" group refers to an "—N(R$_A$)OC(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, sulfo, sulfino, sulfonate, and oxo (=O). Wherever a group is described as "optionally substituted" that group can be substituted with the above substituents.

In some embodiments, substituted alkyl, alkenyl, alkynyl, aryl, heteroaryl, heterocyclyl or carbocyclyl groups are substituted with one or more substituents selected from the group consisting of halo, —CN, —$SO_3^-$, —$SO_3H$, —$SR^A$, —$OR^A$, —$NR^BR^C$, oxo, —$CONR^BR^C$, —$SO_2NR^BR^C$, —COOH, and —$COOR^B$, where $R^A$, $R^B$ and $R^C$ are each independently H, alkyl, substituted alkyl, alkenyl, substituted alkenyl, alkynyl, substituted alkynyl, aryl, or substituted aryl.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

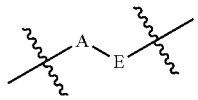

includes the substituent being oriented such that the A is attached at the leftmost attachment point of the molecule as well as the case in which A is attached at the rightmost attachment point of the molecule. In addition, if a group or substituent is depicted as

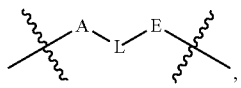

and L is either defined as a bond or L is absent, such group or substituent is equivalent to

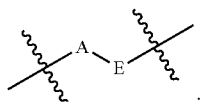

As used herein, "cyclooctatetraene" (COT) is a compound with the structure

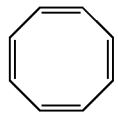

and the chemical formula $C_8H_8$, also known as 1,3,5,7-cyclooctatetraene, cycloocta-1,3,5,7 tetraene or [8] annulene. The dianion of COT (i.e., cyclooctatetraenide, $COT^{2-}$ or $[C_8H_8]^{2-}$) is aromatic. In some embodiments, COT may also refer to its positively- or negatively charged ion, (poly) ions, radical(s) or positively- or negatively charged ion-radical(s).

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof, such as deazapurine. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, deazapurine, 7-deazapurine, adenine, 7-deaza adenine, guanine, 7-deaza guanine, hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, when an oligonucleotide or polynucleotide is described as "comprising" a nucleoside or nucleotide described herein, it means that the nucleoside or nucleotide described herein forms a covalent bond with the oligonucleotide or polynucleotide. Similarly, when a nucleoside or nucleotide is described as part of an oligonucleotide or polynucleotide, such as "incorporated into" an oligonucleotide or polynucleotide, it means that the nucleoside or nucleotide described herein forms a covalent bond with the oligonucleotide or polynucleotide. In some such embodiments, the covalent bond is formed between a 3' hydroxy group of the oligonucleotide or polynucleotide with the 5' phosphate group of a nucleotide described herein as a phosphodiester bond between the 3' carbon atom of the oligonucleotide or polynucleotide and the 5' carbon atom of the nucleotide.

As used herein, "derivative" or "analogue" means a synthetic nucleotide or nucleoside derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate and phosphoramidate linkages. "Derivative", "analog" and "modified" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

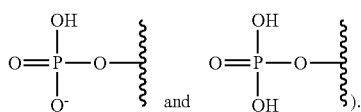 [SMILES: *OP(=O)([O-])O ; *OP(=O)(O)O]

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Sometimes, "protecting group" and "blocking group" can be used interchangeably.

As used herein, the prefixes "photo" or "photo-" mean relating to light or electromagnetic radiation. The term can encompass all or part of the electromagnetic spectrum including, but not limited to, one or more of the ranges commonly known as the radio, microwave, infrared, visible, ultraviolet, X-ray or gamma ray parts of the spectrum. The part of the spectrum can be one that is blocked by a metal region of a surface such as those metals set forth herein. Alternatively, or additionally, the part of the spectrum can be one that passes through an interstitial region of a surface such as a region made of glass, plastic, silica, or other material set forth herein. In particular embodiments, radiation can be used that is capable of passing through a metal. Alternatively, or additionally, radiation can be used that is masked by glass, plastic, silica, or other material set forth herein.

As used herein, the term "phasing" refers to a phenomenon in SBS that is caused by incomplete removal of the 3' blocking groups and fluorescent labels, and failure to complete the incorporation of a portion of DNA strands within clusters by polymerases at a given sequencing cycle. Pre-phasing is caused by the incorporation of nucleotides without effective 3' blocking groups, wherein the incorporation event goes 1 cycle ahead due to a termination failure. Phasing and pre-phasing cause the measured signal intensities for a specific cycle to consist of the signal from the current cycle as well as noise from the preceding and following cycles. As the number of cycles increases, the fraction of sequences per cluster affected by phasing and pre-phasing increases, hampering the identification of the correct base. Pre-phasing can be caused by the presence of a trace amount of unblocked 3'-OH nucleotides during sequencing by synthesis (SBS). The unblocked 3'—OH nucleotides could be generated during the manufacturing processes or possibly during the storage and reagent handling processes.

As used herein, the term "detection solution" refers to an aqueous based solution used during a detection step of sequencing which employs light irradiation to identify the incorporated nucleotides or nucleotide labeled with the fluorescent dyes to a copy of polynucleotide strand that is complementary to a template DNA. A detection solution typically contains one or more antioxidants, or reagents (such as phenolic compounds) that can act as scavengers or quenchers to oxygen radicals or other radicals formed during the detecting step. The detection solution reduces light-induced degradation upon exposure of an array of nucleic acids to illumination. In some embodiments, the detection solution comprises a composition containing COT as described herein.

As used herein the term "buffer," when used alone refers to a buffer solution not used as a detection solution. Buffer solutions include those used in polymerase reactions, hybridizations, washing, or any other operation performed prior to or after the use of the detection solution.

As used herein the term "phenolic compound" and "polyphenolic compound" refers to an aromatic compound having one- or multiple hydroxyl group(s) (i.e. phenolic groups) on a benzene or other aromatic- or heterocyclic ring. The benzene, or other aromatic/heterocyclic ring, can be optionally substituted with other substituents and/or fused rings. Exemplary polyphenolic compounds include, without limitation, trolox, gallic acid and lower alkyl esters thereof, monomethyl ethers thereof, and combinations of lower alkyl esters and monomethyl ethers thereof, pyrogallol, and hydroquinones, such as t-butyl hydroquinone (TBHQ), 2,4,5-trihydroxybutyrophenone (THBP).

As used herein, the term "light-induced degradation" means the light-induced damage to one or more nucleic acids or polynucleotide strands in an array of nucleic acids by exposure to light illumination. Such degradation includes the complete or partial removal of individual nucleic acids from the support to which the array is attached. For example, light-induced degradation can include cleavage of the phosphodiester backbone at any of the nucleotides within an individual nucleic acid. Such degradation can also include removal of or reaction of a nucleic acid base or fluorescent tag causing a loss in hybridization or fluorescence function. Light-induced degradation can also include photo-induced crosslinking of nucleotides. The result of light-induced degradation can manifest as a decrease in fluorescence detection sensitivity in one or more regions or sub-arrays of an array nucleic acids when cycling through repeated detection steps, as might be observed, for example, when performing sequencing by synthesis, sequencing by ligation and microarray scanning. When used in conjunction with the term "inhibiting," this refers to a complete or partial block in the extent of damage, for example, as can be quantified by the observed strength of fluorescent emission. Light induced damage can be presented, for example, as a function of fluorescence signal intensity decay versus number of repeated irradiation (detection) steps performed on the array of nucleic acids. This process is sometimes referred to as signal intensity decay. Another assessment of light damage can be estimated as a function of sequencing error rate versus number of repeated irradiation (detection) steps performed on the array of nucleic acids.

As used herein, the term "cyanine dye" refer to a family of dyes belonging to the polymethine group, in which the chromophoric system includes conjugated double bonds connecting two end groups: an electron acceptor and an electron donor. There are three types of cyanine dyes: (1) closed chain cyanines of the general structure:

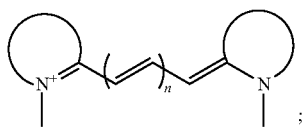

(2) hemicyanines of the general structure:

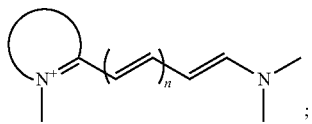

and (3) open chain cyanines of the general structure:

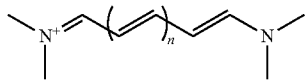

Non-limiting examples of closed chain cyanine dyes include Cy2, Cy3, Cy3B, Cy3.5, Cy5, Cy5.5, and Cy7 and analogs thereof.

Fluorescent Compounds with Covalently Bonded COT Moiety

Some embodiments described herein are related to fluorescent compounds having a cyclooctatetraene moiety comprises the structure of formula (I):

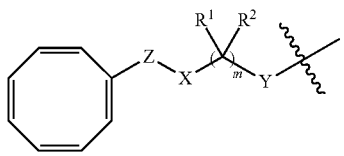

wherein:
each of $R^1$ and $R^2$ are each independently selected from the group consisting of H, hydroxyl, halogen, azido, thiol, nitro, cyano, optionally substituted amino, carboxyl, —C(O)OR$^5$, —C(O)NR$^6$R$^7$, optionally substituted alkyl, optionally substituted alkoxy, optionally substituted haloalkyl, optionally substituted haloalkoxy, optionally substituted alkenyl, optionally substituted alkynyl, optionally substituted aryl, optionally substituted aralkyl, optionally substituted carbocyclyl, optionally substituted heteroaryl, and optionally substituted heterocyclyl and combinations thereof;

X and Y are each independently selected from the group consisting of a bond, —O—, —S—, —NR$^3$—, —C(=O)—, —C(=O)—O—, —C(=O)—NR$^4$—, —S(O)$_2$—, —NR$^3$—C(=O)—NR$^4$, —NR$^3$—C(=S)—NR$^4$—, optionally substituted $C_{1-6}$ alkylene, and optionally substituted heteroalkylene where at least one carbon atom is replaced with O, S, or N;

Z is absent, optionally substituted $C_{2-6}$ alkenylene, or optionally substituted $C_{2-6}$ alkynylene; each of $R^3$ and $R^4$ is independently H, optionally substituted $C_{1-6}$ alkyl, or optionally substituted $C_{6-10}$ aryl;

$R^5$ is optionally substituted $C_{1-6}$ alkyl, optionally substituted $C_{6-10}$ aryl, optionally substituted $C_{7-14}$ aralkyl, optionally substituted $C_{3-7}$ carbocyclyl, optionally substituted 5 to 10 membered heteroaryl, or optionally substituted 3 to 10 membered heterocyclyl;

each of $R^6$ and $R^7$ is independently H, optionally substituted $C_{1-6}$ alkyl, optionally substituted $C_{6-10}$ aryl, optionally substituted $C_{7-14}$ aralkyl, optionally substituted $C_{3-7}$ carbocyclyl, optionally substituted 5 to 10 membered heteroaryl, or optionally substituted 3 to 10 membered heterocyclyl;

the carbon atom to which $R^1$ and $R^2$ are attached in

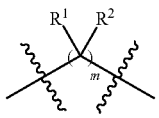

is optionally replaced with O, S, or N, provided that when said carbon atom is replaced with O or S, then $R^1$ and $R^2$ are both absent; when said carbon atom is replaced with N, then $R^2$ is absent; and m is an integral number between 0 and 10. In some embodiments, the

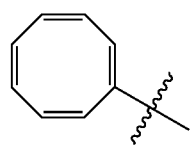 [SMILES: *C1=C/C=C\C=C/C=C\1]

portion may be optionally substituted. In some embodiments, X and Y are not both a bond. In some further embodiments, the fluorescent compound is not a cyanine dye. In some further embodiments, the fluorescent compound is not a closed chain cyanine dye. In some further embodiments, each of $R^1$ and $R^2$ are each independently selected from the group consisting of H, hydroxyl, halogen, azido, thiol, nitro, cyano, optionally substituted amino, carboxyl, optionally substituted $C_{1-6}$ alkyl, optionally substituted $C_{1-6}$ alkoxy, optionally substituted $C_{1-6}$ haloalkyl, optionally substituted $C_{1-6}$ haloalkoxy, optionally substituted $C_{2-6}$ alkenyl, optionally substituted $C_{2-6}$ alkynyl, optionally substituted $C_{6-10}$ aryl, optionally substituted $C_{7-14}$ aralkyl, optionally substituted $C_{3-7}$ carbocyclyl, optionally substituted 5 to 10 membered heteroaryl, and optionally substituted 3 to 10 membered heterocyclyl.

In some embodiments of the fluorescent compounds described herein, Z is absent and the cyclooctatetraene moiety comprises the structure of formula (I'):

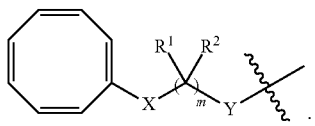

In other embodiments, Z is an optionally substituted $C_{2-6}$ alkenylene. In one embodiment, Z is

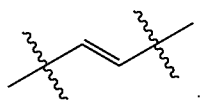

In other embodiments, Z is an optionally substituted $C_{2-6}$ alkynylene.

In some embodiments of the fluorescent compounds described herein, X is —C(=O)— or —C(=O)NR$^4$—. In some such embodiments, R$^4$ is H. In some other embodiments, R$^4$ is $C_{1-6}$ alkyl (e.g., methyl, ethyl, n-propyl, isopropyl, n-butyl, or tert-butyl). In some other embodiment, R$^4$ is substituted $C_{1-6}$ alkyl, for example, methyl, ethyl, n-propyl, n-butyl, isopropyl, isobutyl, n-pentyl, isopentyl, n-hexyl, or isohexyl, each independently substituted with one or more groups such as amino, carboxyl, —C(O)OR$^5$, or —C(O)NR$^6$R$^7$. In one example, R$^4$ is n-propyl substituted with carboxyl. In some embodiments, Y is —C(=O)O—, —NR$^3$— or —S(O)$_2$—. In some further embodiments, Y is —NR$^3$— and R$^3$ is H. In other embodiments, Y is —NR$^3$— and R$^3$ is a substituted $C_{1-6}$ alkyl, for example, methyl, ethyl, n-propyl, n-butyl, isopropyl, isobutyl, n-pentyl, isopentyl, n-hexyl, or isohexyl, each independently substituted with amino, carboxyl, —SO$_3$H, —SO$_3^-$, —O—SO$_3^-$—C(O)OR$^5$, or —C(O)NR$^6$R$^7$. In some further embodiments, R$^5$ is $C_{1-6}$ alkyl (e.g., ethyl, n-propyl, n-butyl, isopropyl, isobutyl, n-pentyl, isopentyl, n-hexyl, or isohexyl, each may independently substituted with amino, carboxyl, —SO$_3$H, —SO$_3^-$ or —O—SO$_3^-$). In some other embodiments, R$^5$ is $C_{6-10}$ aryl (such as phenyl, optionally substituted with halo, alkyl, alkoxy, haloalkyl, haloalkoxy, hydroxyl, cyano, amino, carboxyl, —SO$_3$H, —SO$_3^-$ or —O—SO$_3^-$). In some further embodiments, R$^6$ is H. In some further embodiments, both R$^6$ and R$^7$ are H. In some further embodiments, R$^6$ is an optionally substituted $C_{1-6}$ alkyl (e.g., ethyl, n-propyl, n-butyl, isopropyl, isobutyl, n-pentyl, isopentyl, n-hexyl, or isohexyl, each may independently substituted with amino, carboxyl, —SO$_3$H, —SO$_3^-$ or —O—SO$_3^-$). In some further embodiments, R$^6$ is H and R$^7$ is an optionally substituted $C_{1-6}$ alkyl, or both R$^6$ and R$^7$ are independently an optionally substituted $C_{1-6}$ alkyl (e.g., ethyl, n-propyl, n-butyl, isopropyl, isobutyl, n-pentyl, isopentyl, n-hexyl, or isohexyl, each may independently substituted with amino, carboxyl, —SO$_3$H, —SO$_3^-$ or —O—SO$_3^-$). In some embodiments, X and Y cannot both be a bond, for example, when X is a bond, Y is not a bond.

Other non-limiting examples of X, Y, and Z combination are exemplified in the Table 1 below.

TABLE 1

Exemplary X, Y, and Z in cyclooctatetraene moiety of formula (I)

| X | Y | Z |
|---|---|---|
| —C(=O)NR$^4$— | —NR$^3$— | absent |
| —C(=O)NR$^4$— | —NR$^3$— | (alkenylene) |
| —C(=O)NR$^4$— | —C(=O)— | absent |
| —C(=O)NR$^4$— | —C(=O)— | (alkenylene) |
| —C(=O)NR$^4$— | —C(=O)O— | absent |
| —C(=O)NR$^4$— | —C(=O)O— | (alkenylene) |
| —C(=O)NR$^4$— | —S(=O)$_2$— | absent |
| —C(=O)NR$^4$— | —S(=O)$_2$— | (alkenylene) |
| —C(=O)— | —NR$^3$— | absent |
| —C(=O)— | —NR$^3$— | (alkenylene) |
| —C(=O)— | —C(=O)—NR$^4$— | absent |
| —C(=O)— | —C(=O)—NR$^4$— | (alkenylene) |
| —C(=O)— | —NR$^3$—C(=O)—NR$^4$ | absent |
| —C(=O)— | —NR$^3$—C(=O)—NR$^4$ | (alkenylene) |
| —C(=O)— | —S(=O)$_2$— | absent |
| —C(=O)— | —S(=O)$_2$— | (alkenylene) |
| bond | —NR$^3$— | absent |
| bond | —NR$^3$— | (alkenylene) |

TABLE 1-continued

Exemplary X, Y, and Z in cyclooctatetraene moiety of formula (I)

| X | Y | Z |
|---|---|---|
| bond | —C(=O)O— | absent |
| bond | —C(=O)O— | 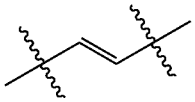 |

In some embodiments, the cyclooctatetraene moiety comprises the structure of formula (Ia):

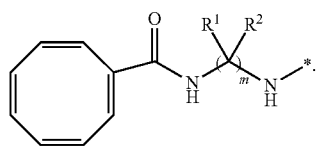
(Ia)

In some other embodiments, the cyclooctatetraene moiety comprises the structure of formula (Ib):

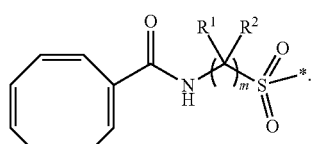
(Ib)

In some other embodiments, the cyclooctatetraene moiety comprises the structure of formula (Ic):

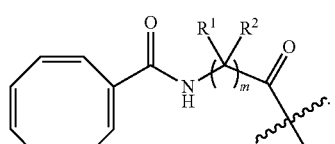
(Ic)

In some other embodiments, the cyclooctatetraene moiety comprises the structure of formula (Id):

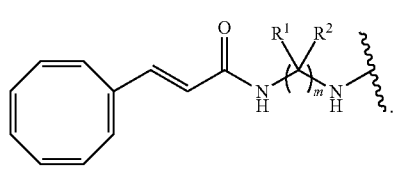
(Id)

In some embodiments of fluorescent compound comprising a COT moiety of formula (I), (Ia), (Ib), (Ic) or (Id), at least one of $R^1$ and $R^2$ is hydrogen. In some further embodiments, both $R^1$ and $R^2$ are hydrogen. In some other embodiments, $R^1$ is H and $R^2$ is an optionally substituted amino or carboxyl. In some embodiments, m is 1, 2, 3, 4, 5, or 6, and each of $R^1$ and $R^2$ is independently hydrogen, optionally substituted amino, or carboxyl, or combinations thereof. In some further embodiments, when m is 2, 3, 4, 5, or 6, one $R^1$ is amino or carboxyl, and the remaining $R^1$ and $R^2$ are hydrogen. one In some embodiments, at least one carbon atom to which $R^1$ and $R^2$ are attached in

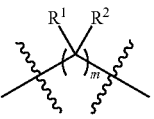

is replaced with O, S, or N. In some such embodiments, one carbon atom in

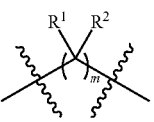

is replaced by an oxygen atom, and both $R^1$ and $R^2$ attached to said replaced carbon atom are absent. In some other embodiments, when one carbon atom in

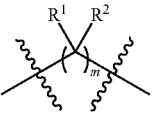

is replaced by an nitrogen atom, $R^2$ attached to said replaced carbon atom is absent, and $R^1$ attached to said replaced carbon atom is hydrogen, or $C_{1-6}$ alkyl. In some further embodiments, m is 2, 3, 4, 5 or 6, and each one of $R^1$ and $R^2$ is hydrogen. In some further embodiments, m is 2, 3, 4, 5, or 6 wherein each of $R^1$ and $R^2$ is hydrogen in

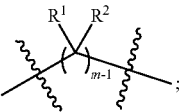

and wherein $R^1$ is H, and $R^2$ is amino, carboxyl, —C(O)OR$^5$, or —C(O)NR$^6$R$^7$ in the remaining

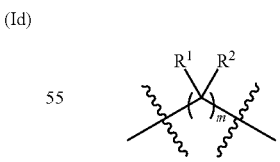

(for example, the remaining may

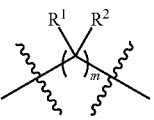

be located either in the terminal of the

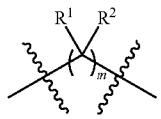

chain, or be in the middle of the

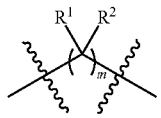

chain. In some further embodiments, when $R^1$ is H and $R^2$ is —C(O)OR$^5$, $R^5$ is H, $C_{1-6}$ alkyl, or optionally substituted phenyl. In some further embodiments, when $R^1$ is H and $R^2$ is —C(O)NR$^6$R$^7$, both $R^6$ and $R^7$ are H. In some further embodiments, when $R^1$ is H and $R^2$ is —C(O)OR$^5$, $R^5$ is an optionally substituted $C_{1-6}$ alkyl (e.g., ethyl, n-propyl, n-butyl, isopropyl, isobutyl, n-pentyl, isopentyl, n-hexyl, or isohexyl, each may independently substituted with amino, carboxyl, —SO$_3$H, —SO$_3^-$ or —O—SO$_3^-$). In some further embodiments, when $R^1$ is H and $R^2$ is —C(O)NR$^6$R$^7$, $R^6$ is H and $R^7$ is an optionally substituted $C_{1-6}$ alkyl, or both $R^6$ and $R^7$ are independently an optionally substituted $C_{1-6}$ alkyl (e.g., ethyl, n-propyl, n-butyl, isopropyl, isobutyl, n-pentyl, isopentyl, n-hexyl, or isohexyl, each may independently substituted with amino, carboxyl, —SO$_3$H, —SO$_3^-$ or —O—SO$_3^-$). Further non-limiting examples of

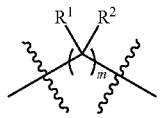

includes the following structures:

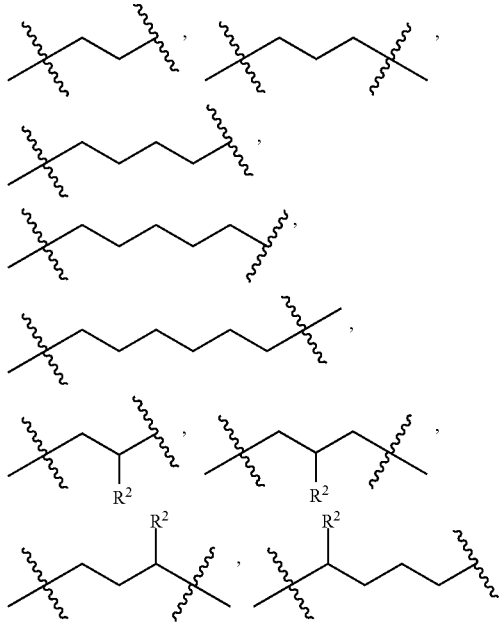

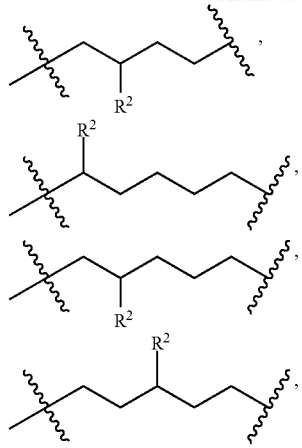

where each $R^2$ is independently amino, carboxyl, —C(O)OR$^5$, or —C(O)NR$^6$R$^7$ as described here. In further embodiments, any of the CH$_2$ carbon atom may also be replaced with O, S, or NH.

In some further embodiments, the fluorescent compounds described herein comprises a cyclooctatetraene moiety of the following structures:

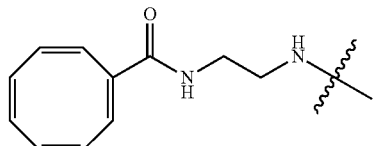

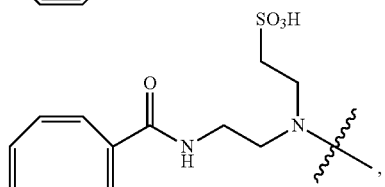

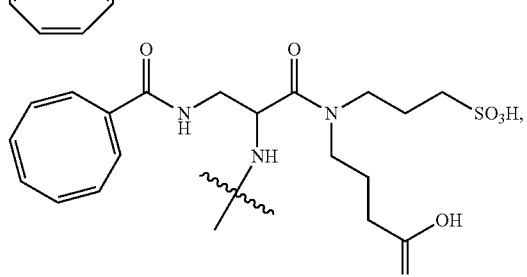

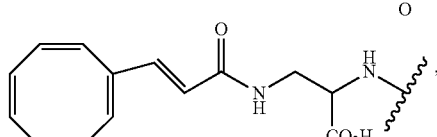

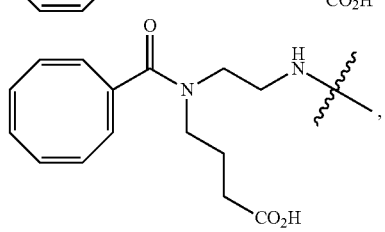

-continued

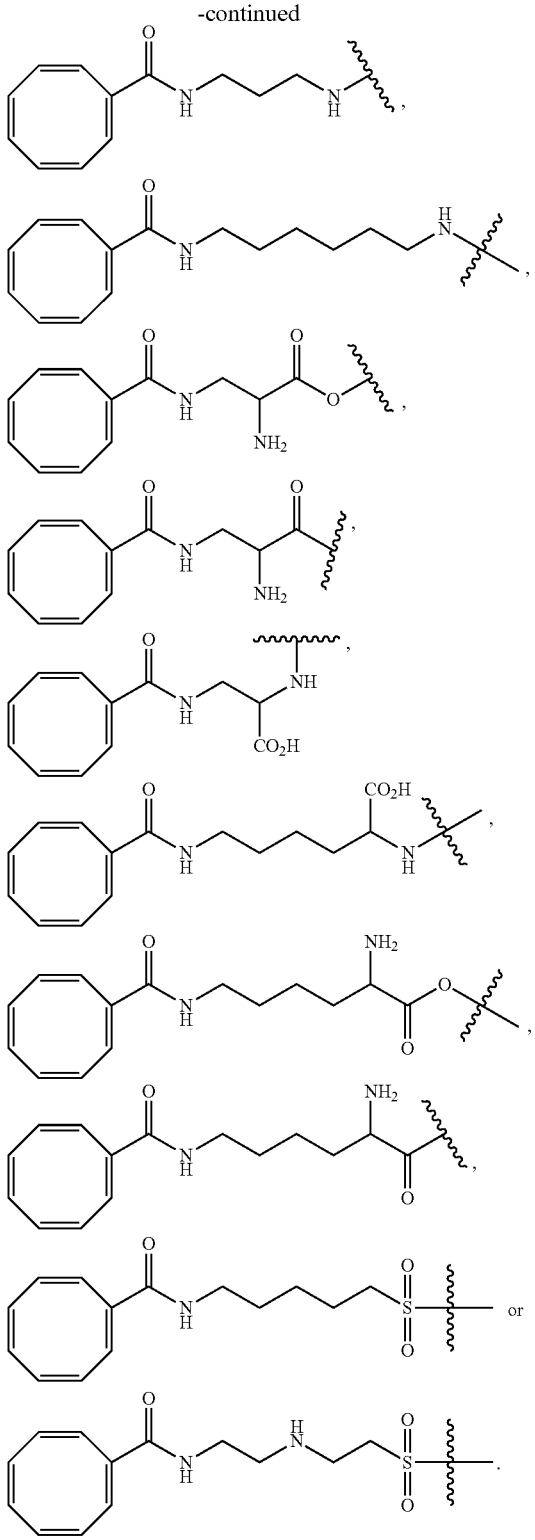

The alkyl or substituted alkyl disclosed herein is $C_{1-12}$ alkyl, or more preferably $C_1$-6 alkyl. In some embodiments, the alkoxy disclosed herein is $C_{1-12}$ alkoxy, or more preferably $C_{1-6}$ alkoxy. In some embodiments, the alkenyl and alkynyl groups disclosed herein are $C_{2-6}$ alkenyl and $C_{2-6}$ alkynyl. In some embodiments, the haloalkyl and haloalkoxy groups disclosed herein are $C_{1-12}$ haloalkyl and $C_{1-12}$ haloalkoxy, more preferably $C_{1-6}$ haloalkyl and $C_{1-6}$ haloalkoxy. In some embodiments, the optionally substituted aryl disclosed herein is optionally substituted $C_{6-10}$ aryl, for example, phenyl. In some embodiments, the optionally substituted aralkyl disclosed herein is optionally substituted $C_{7-14}$ aralkyl, for example, benzyl. In some embodiments, the optionally substituted heteroaryl disclosed herein is optionally substituted 5-10 membered heteroaryl; more preferably, optionally substituted 5-6 membered heteroaryl. In some embodiments, the optionally substituted carbocyclyl disclosed herein is optionally substituted 3-7 membered carbocyclyl, in particular 3-7 membered cycloalkyl. In some embodiments, optionally substituted heterocyclyl disclosed herein are optionally substituted 3-7 membered heterocyclyl, more preferably 5-6 membered heterocyclyl.

In some embodiments, the fluorescent compounds containing covalently bonded COT moiety may be excited by a light source having an emission wavelength between about 350 nm and about 500 nm. In some further embodiments, the fluorescent compound may be excited by a light source having an emission wavelength between about 420 nm and about 480 nm, or about 450 nm to about 460 nm.

In some embodiments of fluorescent compound comprising a COT moiety as described herein, the fluorescent compound is not a cyanine dye, for example, the fluorescent compound is not Cy2, Cy3, Cy5, or Cy7 dyes or derivatives thereof, or optionally substituted analogs thereof. In further embodiments, the fluorescent compound is not Cy5 or derivatives and optionally substituted analogs thereof.

Buffer Compositions Containing COT

Some embodiments of the present disclosure relate to a composition for preventing or reducing photobleaching of a fluorescent labels and/or preventing, reducing or mitigating DNA damage, comprising cyclooctatetraene or an optionally substituted derivative thereof, and one or more antioxidants selected from the group consisting of taxifolin, quercetin, allyl thiourea, dimethyl thiourea, silibinin, gallic acid derivatives, trolox, and optionally substituted derivatives and combinations thereof. In some further embodiment, the composition comprises cyclooctatetraene and quercetin, and optionally substituted derivatives and combinations thereof. In some embodiments, the fluorescent dye may be excited by a light source having an emission wavelength between about 350 nm and about 500 nm. In some embodiments, the fluorescent dye may be excited by a light source having a wavelength between about 420 nm and about 480 nm, or about 450 nm to about 460 nm. In some embodiments, the fluorescent dye is a COT moiety bonded compound as described herein.

In some embodiments, the composition is in an aqueous solution, for example, a water-based buffer solution. In some such embodiment, the composition is in a detection solution. In some further embodiments, cyclooctatetraene or the optionally substituted derivative in the aqueous solution is in a concentration of about 0.1 mM, 0.2 mM, 0.5 mM, 1.0 mM, 2.0 mM, 5.0 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM or 100 mM, or a range defined by any two of the preceding values. In some further embodiments, cyclooctatetraene or the optionally substituted derivative is in a concentration from about 0.1 mM to about 100 mM, or from about 1 mM to about 50 mM, from about 2 mM to about 25 mM, from about 5 mM to about 15 mM, or about 10 mM. In some embodiments, quercetin or the optionally substituted derivative in the aqueous solution is in a concentration of about 0.01 mM, 0.02 mM, 0.05 mM, 0.1 mM, 0.2 mM, 0.3 mM, 0.4 mM, 0.5 mM, 0.6 mM, 0.7 mM, 0.8 mM, 0.9 mM, 1.0 mM, 2.0 mM, 5.0 mM, or 10 mM, or a range defined by any two of the preceding values. In some further embodiments, quercetin or the optionally substituted derivative is in a concentration from about 0.01 mM to about 10 mM, from about 0.02 mM to about 5 mM, from about 0.05 mM to about 2 mM, from about 0.1 mM to about 1 mM, from about 0.2 mM to about 0.5 mM, or about 0.25 mM.

In some embodiments, the composition further comprises additional antioxidant(s), for example, ascorbic acid or a salt thereof (such as sodium ascorbate), or one or more polyphenolic compounds. The composition may further comprise one or more fluorescent dyes.

Some embodiments of the present disclosure relate to a method of protecting a fluorescent dye from photobleaching, comprising contacting the fluorescent dye with a composition containing cyclooctatetraene as described herein. Additional embodiments relate to a method of protecting a labeled nucleoside or nucleotide from light-induced degradation, comprising contacting the labeled nucleoside or nucleotide with the composition described herein. In some embodiments, the labeled nucleotide is incorporated into a polynucleotide strand. In some embodiments, the contacting of the labeled nucleotide with the COT containing composition described herein is during a detection step of a sequencing run.

Fluorescent Compounds

The photo-protecting COT moiety described herein may be covalently attached to various fluorescent dyes suitable for sequencing analysis, for example, sequencing by synthesis technologies for the purpose of preventing or reducing photobleaching of the dye and/or fluorescent signal decay during sequencing runs. Furthermore, a detection solution including a composition containing COT described herein may also be suitable for preventing or reducing DNA damage during the detection step of the nucleic acid sequencing application, after a nucleotide labeled with a fluorescent compound is incorporated into a polynucleotide strand complementary to at least a portion of a template polynucleotide strand.

In some embodiments, the fluorescent compounds used for nucleotide labeling are referred to as "blue dyes", meaning they may be excited by a short wavelength light source (LED or laser) between 400 nm to 500 nm, more particularly, between 450 nm to 460 nm. These compounds have been described in U.S. Publication Nos. 2018/0094140 and 2018/0201981, as well as U.S. Ser. Nos. 62/812,837 and 62/812,732, each of which is incorporated by reference in its entirety.

Fluorescent compounds of Formula (A)

In some embodiments, the fluorescent compounds are represented by Formula (A) or a salt or mesomeric form thereof:

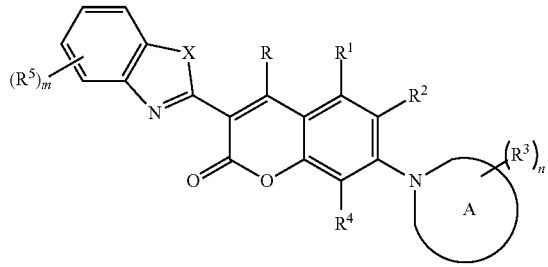

Formula (A)

wherein:
X is O, S, Se, or NR″, wherein R″ is H, $C_{1-6}$ alkyl, or $C_{6-10}$ aryl;
ring A is a 3 to 10 membered heterocyclyl; R, $R^1$, $R^2$, and $R^4$ are each independently H, halo, —CN, —$CO_2H$, amino, —OH, C-amido, N-amido, —$NO_2$, —$SO_3H$, —$SO_2NR^aR^b$, optionally substituted alkyl, optionally substituted alkenyl, optionally substituted alkynyl, optionally substituted alkoxy, optionally substituted aminoalkyl, optionally substituted carbocyclyl, optionally substituted heterocyclyl, optionally substituted aryl, or optionally substituted heteroaryl;
each $R^3$ is independently halo, —CN, —$CO_2H$, —$(CH_2)_p$—$CO_2R^c$, —$(CH_2)_q$—$C(O)NR^dR^e$, amino, —OH, C-amido, N-amido, —$NO_2$, —$SO^3H$, —$SO_2NR^aR^b$, optionally substituted $C_{1-6}$ alkyl, optionally substituted $C_{2-6}$ alkenyl, optionally substituted $C_{2-6}$ alkynyl, optionally substituted carbocyclyl, optionally substituted heterocyclyl, optionally substituted aryl, or optionally substituted heteroaryl, or two $R^3$ form oxo (=O);
wherein p and q are each 1, 2, 3 or 4;
each $R^5$ is independently halo, —CN, —$CO_2R^f$, amino, —OH, C-amido, N-amido, —$NO_2$, —$SO^3H$, —$SO_2NR^aR^b$, optionally substituted alkyl, optionally substituted alkenyl, optionally substituted alkynyl, optionally substituted alkoxy, optionally substituted aminoalkyl, optionally substituted carbocyclyl, optionally substituted heterocyclyl, optionally substituted aryl, or optionally substituted heteroaryl;
each $R^a$ and $R^b$ is independently H or optionally substituted $C_{1-6}$ alkyl;
each $R^c$, $R^d$, $R^e$ and $R^f$ is independently H, optionally substituted $C_{1-6}$ alkyl, optionally substituted carbocyclyl, optionally substituted heterocyclyl, optionally substituted aryl, or optionally substituted heteroaryl;
m is 0, 1, 2, 3, or 4; and
n is 0, 1, 2, 3, 4 or 5.

Fluorescent compounds of Formula (B)

In some embodiments, the fluorescent compounds are represented by Formula (B) or a salt or mesomeric form thereof:

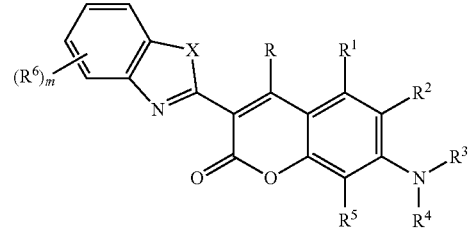

Formula (B)

wherein:
X is O, S, Se, or NR″, wherein R″ is H, $C_{1-6}$ alkyl or $C_{6-10}$ aryl;
each of $R^1$, $R^2$ and $R^5$ is independently H, halo, —CN, —$CO_2H$, amino, —OH, C-amido, N-amido, —$NO_2$, —$SO_3H$, —$SO_2NR^aR^b$, optionally substituted alkyl, optionally substituted alkenyl, optionally substituted alkynyl, optionally substituted alkoxy, optionally substituted aminoalkyl, optionally substituted carbocyclyl, optionally substituted heterocyclyl, optionally substituted aryl, or optionally substituted heteroaryl;

R is H, halo, —CN, —CO$_2$H, amino, —OH, C-amido, N-amido, —NO$_2$, —SO$_3$H, —SO$_2$NR$^a$R$^b$, optionally substituted alkyl, optionally substituted alkenyl, optionally substituted alkynyl, optionally substituted alkoxy, optionally substituted aminoalkyl, optionally substituted carbocyclyl, optionally substituted heterocyclyl, or optionally substituted heteroaryl;

each R$^3$ and R$^4$ is independently C$_{1-6}$ alkyl, —(CH$_2$)$_p$—CO$_2$R$^c$, —(CH$_2$)$_q$—C(O)NR$^d$R$^e$, —(CH$_2$)$_n$—SO$_3$H, —(CH$_2$)$_t$—SO$_2$NR$^a$R$^b$, and wherein each p, q, n and t is independently 1, 2, 3, 4, 5 or 6;

each R$^6$ is independently halo, —CN, —CO$_2$R$^f$, amino, —OH, C-amido, N-amido, —NO$_2$, —SO$_3$H, —SO$_2$NR$^a$R$^b$, optionally substituted alkyl, optionally substituted alkenyl, optionally substituted alkynyl, optionally substituted alkoxy, optionally substituted aminoalkyl, optionally substituted carbocyclyl, optionally substituted heterocyclyl, optionally substituted aryl, or optionally substituted heteroaryl;

each R$^a$ and R$^b$ is independently H or optionally substituted C$_{1-6}$ alkyl;

each R$^c$, R$^d$, W and R$^f$ is independently H, optionally substituted C$_{1-6}$ alkyl, optionally substituted carbocyclyl, optionally substituted heterocyclyl, optionally substituted aryl, or optionally substituted heteroaryl; and m is 0, 1, 2, 3, or 4.

Fluorescent compounds of Formula (C)

In some embodiments, the fluorescent compounds are represented by Formula (C) or a salt or mesomeric form thereof:

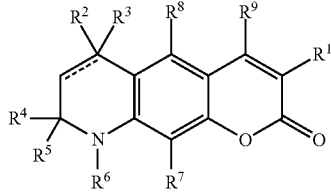

Formula (C)

wherein R$^1$ is

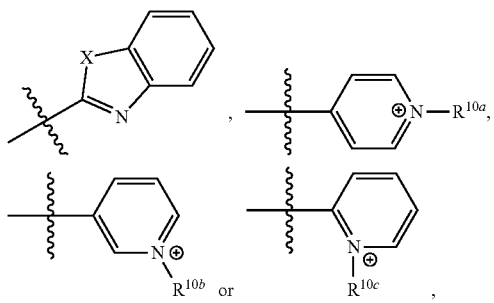

and wherein R$^1$ is optionally substituted with one or more substituents selected from the group consisting of alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, carboxyl, C-carboxy, O-carboxy, C-amido, N-amido, nitro, sulfonyl, sulfo, sulfino, sulfonate, S-sulfonamido, N-sulfonamido, optionally substituted aryl, optionally substituted heteroaryl, optionally substituted cycloalkyl, and optionally substituted heterocyclyl;

each R$^2$, R$^3$, R$^4$, R$^5$, and R$^9$ is independently selected from the group consisting of H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl;

each R$^6$, R$^{10a}$, R$^{10b}$ and R$^{10c}$ is independently selected from the group consisting of H, alkyl, substituted alkyl, alkenyl, alkynyl, aminoalkyl, haloalkyl, heteroalkyl, alkoxyalkyl, sulfonyl hydroxide, optionally substituted aryl, optionally substituted heteroaryl, optionally substituted carbocyclyl, and optionally substituted heterocyclyl;

each R$^7$ and R$^8$ is independently selected from the group consisting of H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl;

alternatively, R$^6$ and R$^7$ together with the atoms to which they are attached form a ring or ring system selected from the group consisting of optionally substituted 5-10 membered heteroaryl or optionally substituted 5-10 membered heterocyclyl;

X is selected from the group consisting of O, S, NR$^{11}$, and Se;

R$^{11}$ is selected from the group consisting of H, alkyl, substituted alkyl, alkenyl, alkynyl, aminoalkyl, carboxyalkyl, sulfonatoalkyl, haloalkyl, heteroalkyl, alkoxyalkyl, sulfo, optionally substituted aryl, optionally substituted heteroaryl, optionally substituted carbocyclyl, and optionally substituted heterocyclyl; and the bond represented by a solid and dashed line ═══ is selected from the group consisting of a single bond and a double bond, provided that when ═══ is a double bond, then R$^3$ is absent.

Fluorescent compounds of Formula (D)

In some embodiments, the fluorescent compounds are represented by Formula (D) or a salt or mesomeric form thereof:

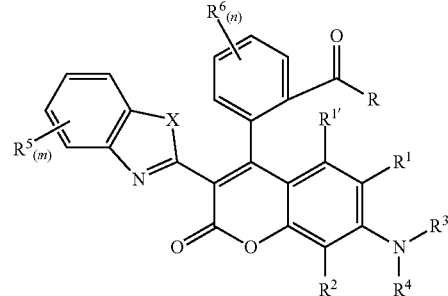

Formula (D)

wherein each R$^1$, R$^2$, and R$^{1'}$ is independently selected from the group consisting of H, alkyl, substituted alkyl, alkoxy, alkenyl, alkynyl, haloalkyl, haloalkoxy, alkoxyalkyl, amino, aminoalkyl, aminosulfonyl, halo, cyano, hydroxy, hydroxyalkyl, heteroalkyl, C-carboxy, O-carboxy, C-amido, N-amido, nitro, sulfonyl, sulfo, sulfino, sulfonate, sulfonyl halide, S-sulfonamido, N-sulfonamido, optionally substituted carbocyclyl, optionally substituted aryl, optionally substituted heteroaryl and optionally substituted heterocyclyl;

alternatively, $R^1$ and $R^{1'}$ together and with the atoms to which they are attached form a ring or ring system selected from the group consisting of optionally substituted carbocyclyl, optionally substituted aryl, optionally substituted heteroaryl, and optionally substituted heterocyclyl;

each $R^3$ and $R^4$ is independently selected from the group consisting of H, alkyl, substituted alkyl, alkenyl, alkynyl, aminoalkyl, haloalkyl, heteroalkyl, alkoxyalkyl, sulfonyl hydroxide, optionally substituted aryl, optionally substituted heteroaryl, optionally substituted carbocyclyl, and optionally substituted heterocyclyl;

alternatively, $R^1$ and $R^3$ together with the atoms to which they are attached form a ring or ring system selected from the group consisting of optionally substituted 5-10 membered heteroaryl or optionally substituted 5-10 membered heterocyclyl;

alternatively, $R^2$ and $R^4$ together with the atoms to which they are attached form a ring or ring system selected from the group consisting of optionally substituted 5-10 membered heteroaryl and optionally substituted 5-10 membered heterocyclyl;

$R^5$ and $R^6$ is independently selected from the group consisting of alkyl, substituted alkyl, alkoxy, alkenyl, alkynyl, haloalkyl, haloalkoxy, alkoxyalkyl, amino, aminoalkyl, aminosulfonyl, halo, cyano, hydroxy, hydroxyalkyl, heteroalkyl, C-carboxy, O-carboxy, C-amido, N-amido, nitro, sulfonyl, sulfo, sulfino, sulfonate, sulfonyl halide, S-sulfonamido, N-sulfonamido, optionally substituted carbocyclyl, optionally substituted aryl, optionally substituted heteroaryl and optionally substituted heterocyclyl;

R is selected from —$OR^7$ or —$NR^8R^9$;

$R^7$ is selected from the group consisting of H, alkyl, substituted alkyl, optionally substituted aryl, optionally substituted heteroaryl, optionally substituted carbocyclyl, and optionally substituted heterocyclyl;

each $R^8$ and $R^9$ is independently selected from the group consisting of H, alkyl, substituted alkyl, alkenyl, alkynyl, aminoalkyl, carboxyalkyl, sulfonatoalkyl, haloalkyl, heteroalkyl, alkoxyalkyl, sulfo, optionally substituted aryl, optionally substituted heteroaryl, optionally substituted carbocyclyl, and optionally substituted heterocyclyl;

X is selected from the group consisting of O, S, $NR^{10}$, and Se;

$R^{10}$ is selected from the group consisting of H, alkyl, substituted alkyl, optionally substituted aryl, optionally substituted heteroaryl, optionally substituted carbocyclyl, and optionally substituted heterocyclyl;

m is an integer selected from 0 to 4; and n is an integer selected from 0 to 4.

In some specific embodiments, non-limiting exemplary blue dye compounds are shown as the following:

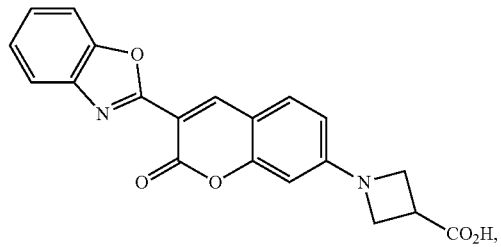

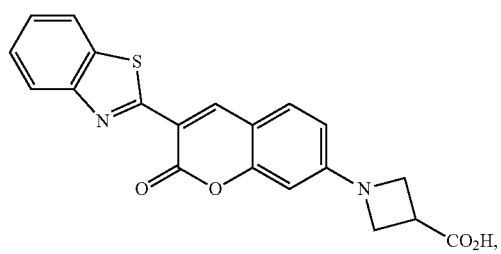

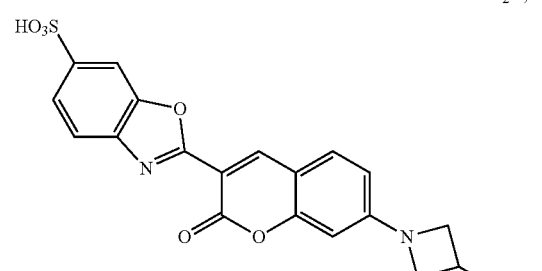

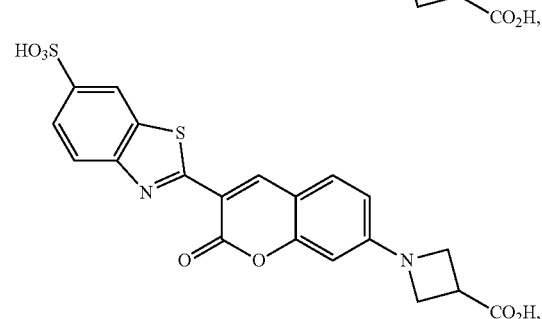

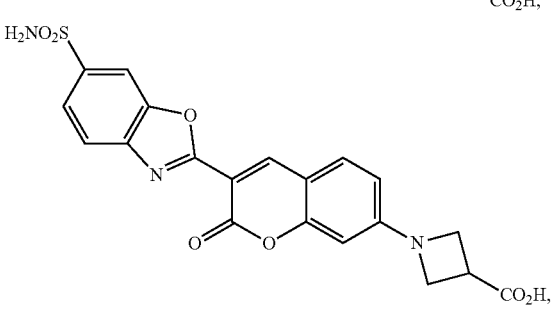

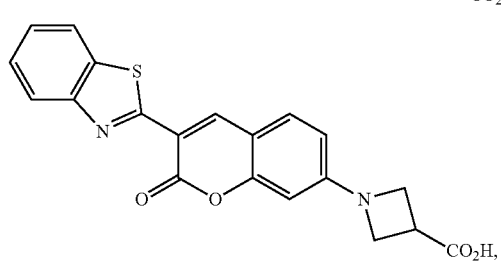

-continued
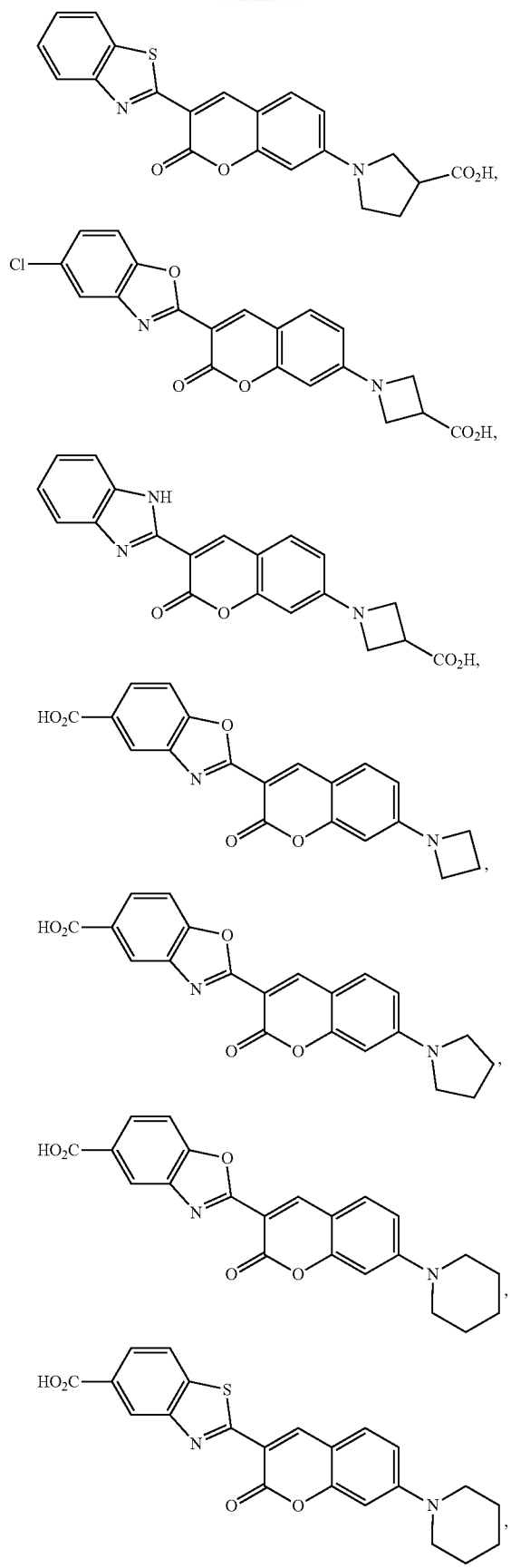
-continued
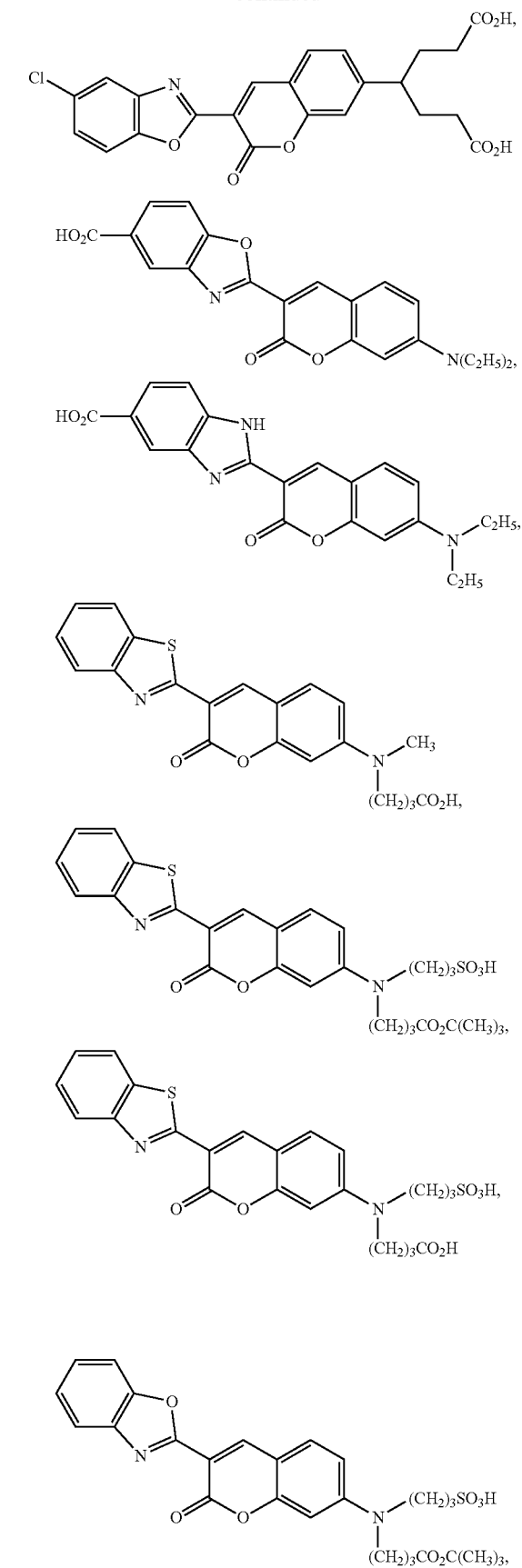

-continued
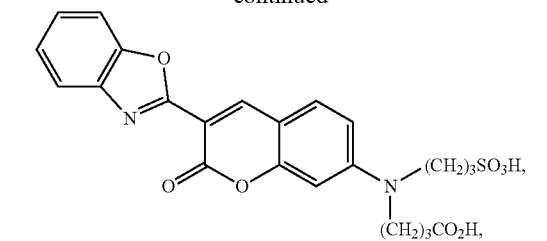
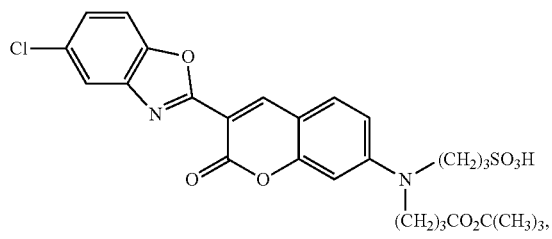
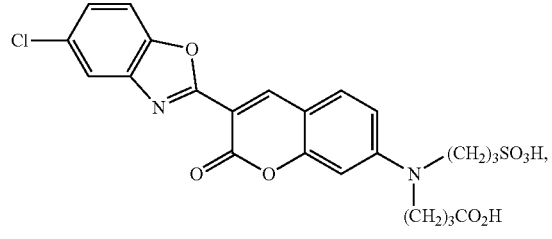
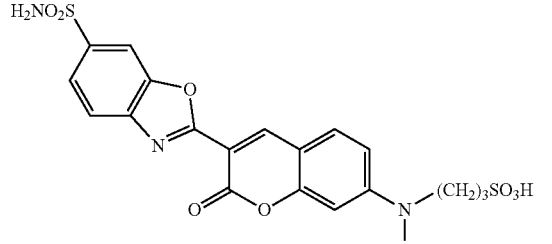
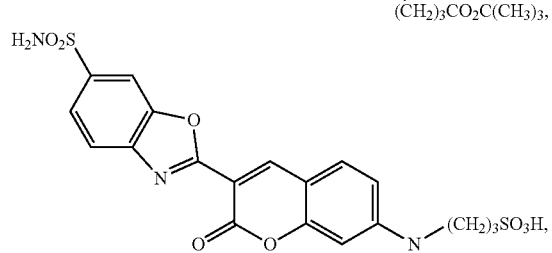
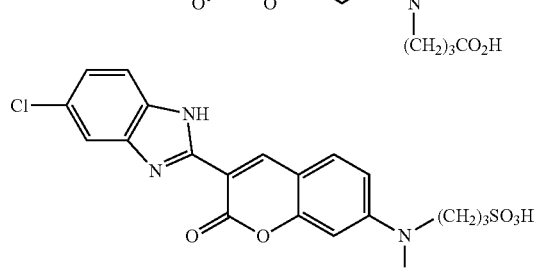
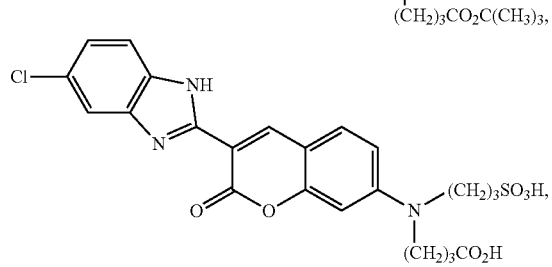
-continued
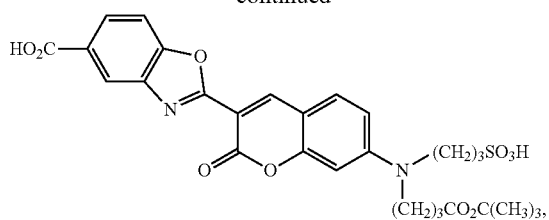
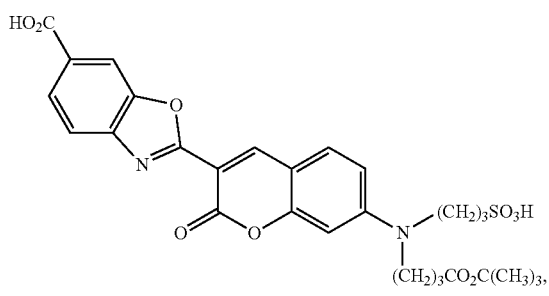
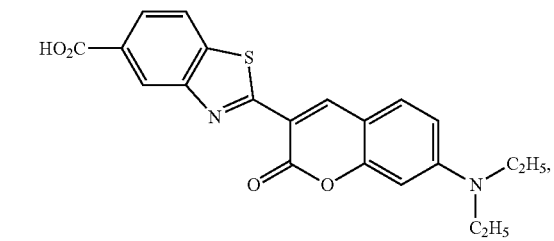
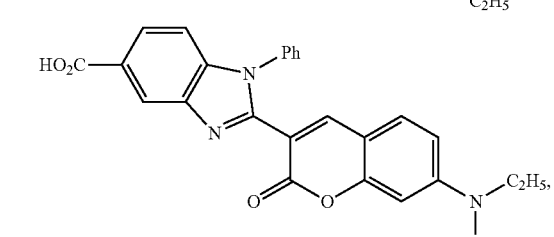
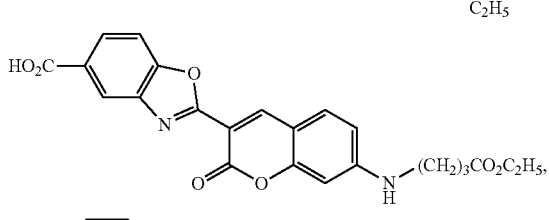
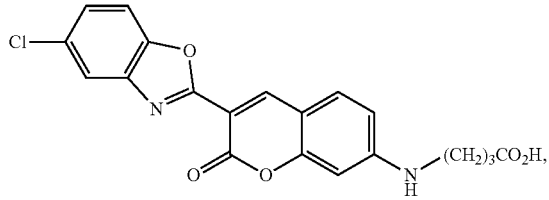
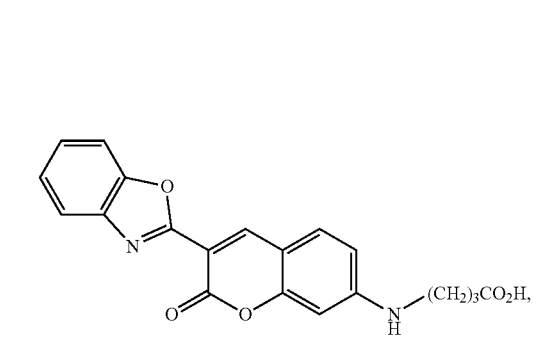

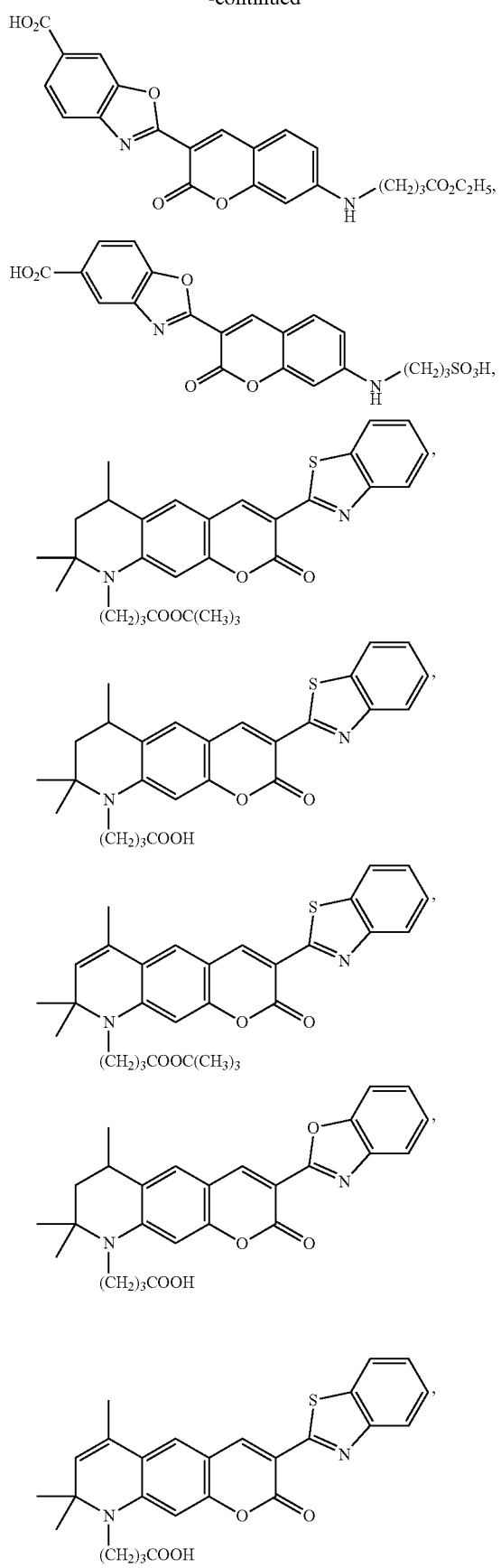
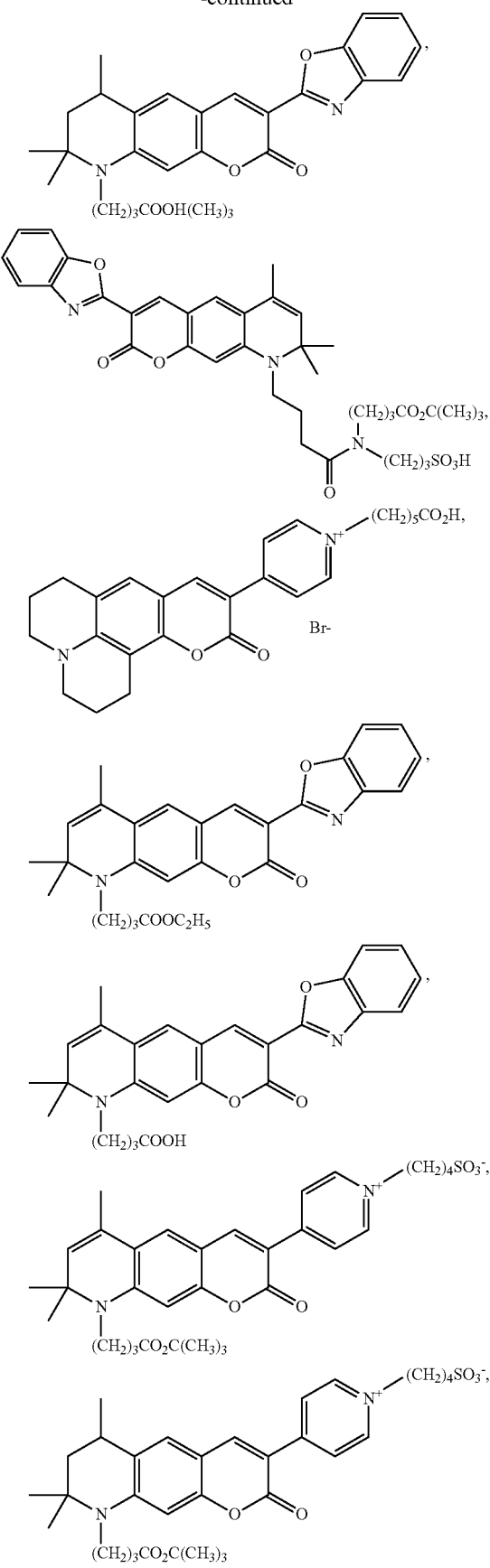

39
-continued
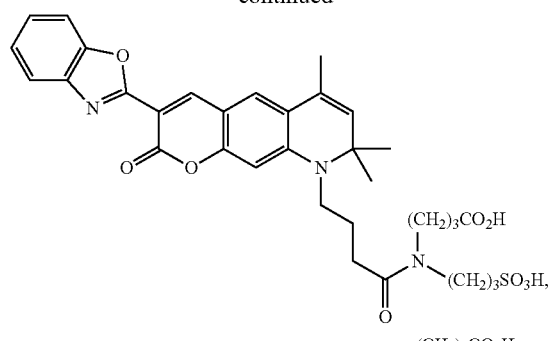
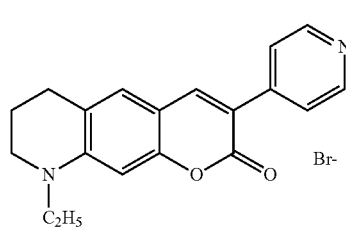
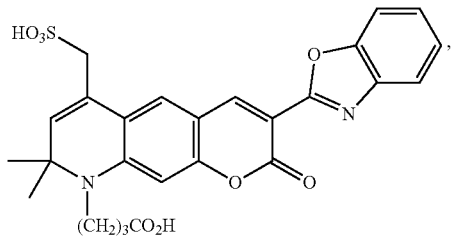
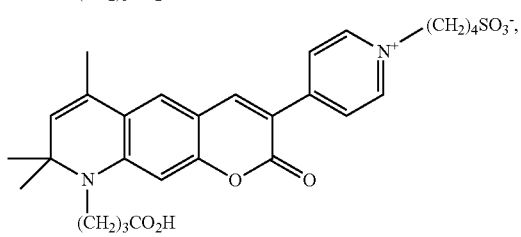
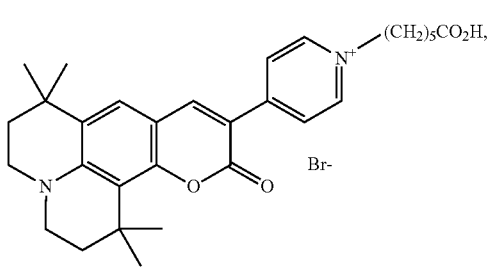
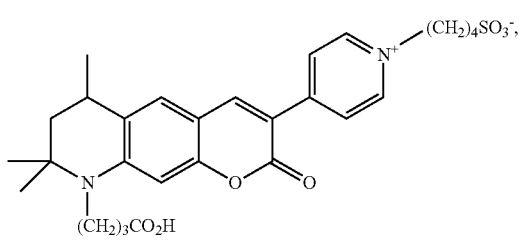
40
-continued
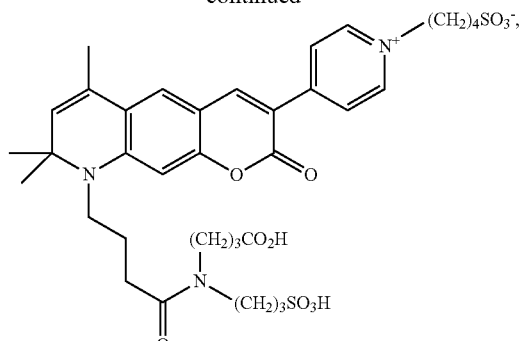
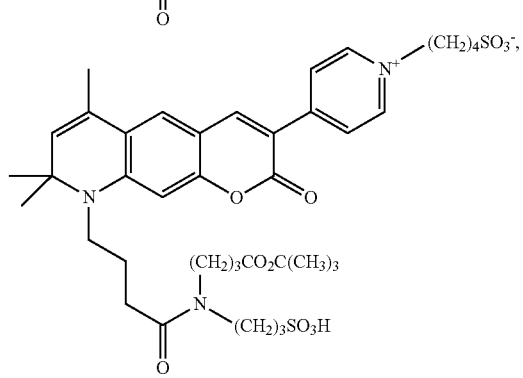
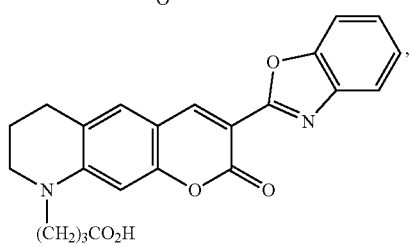
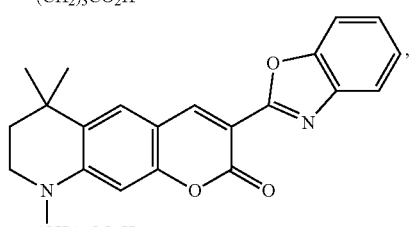
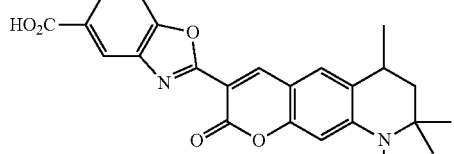
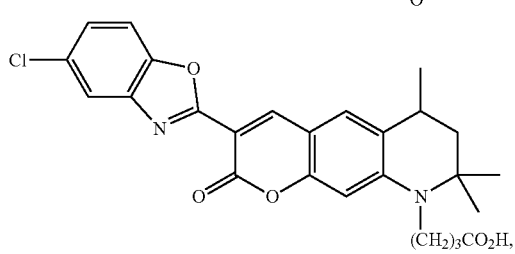

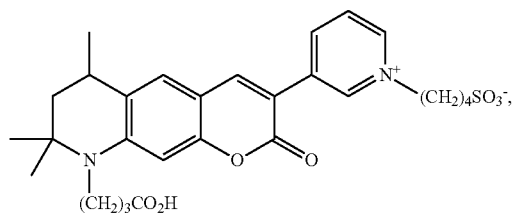
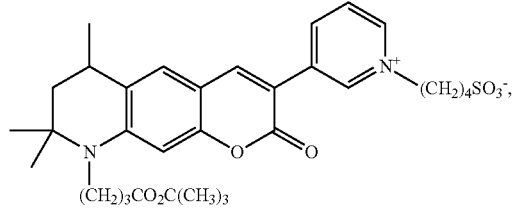
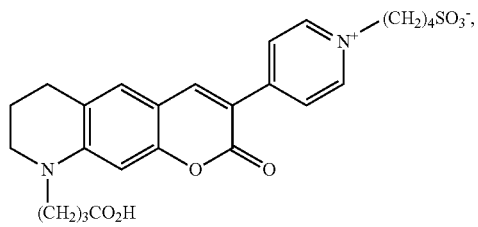
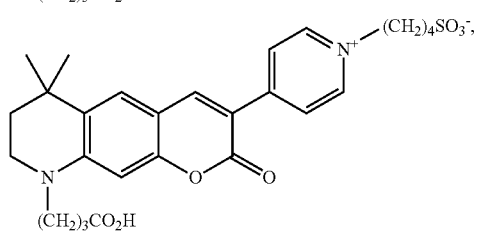
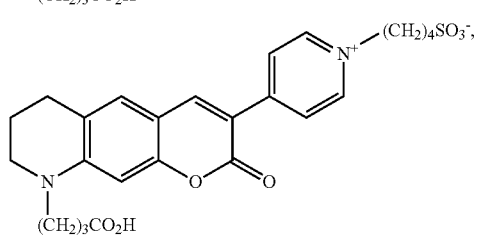
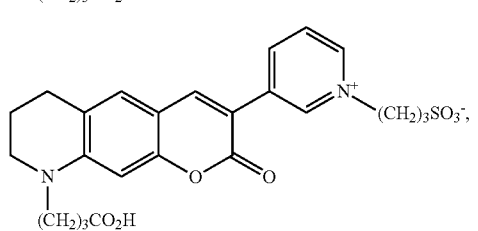
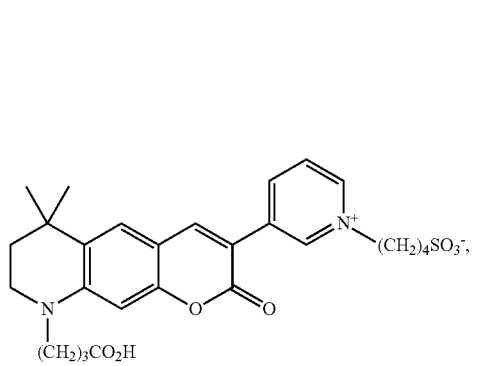
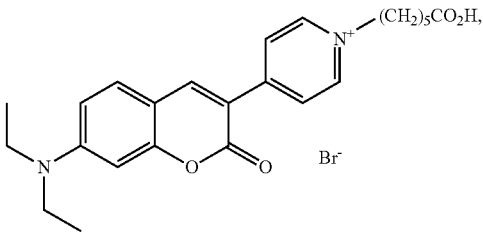
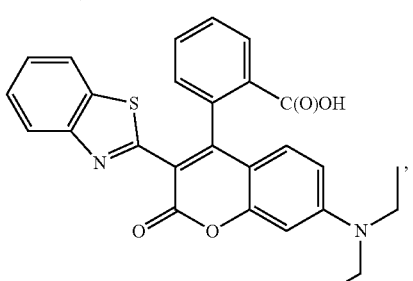
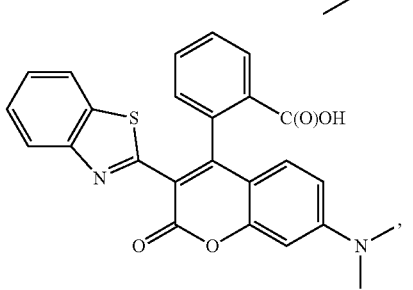
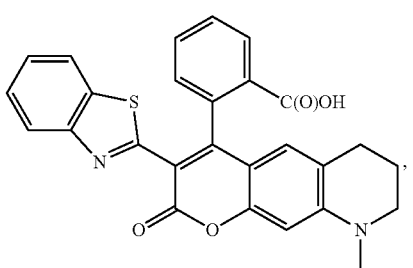
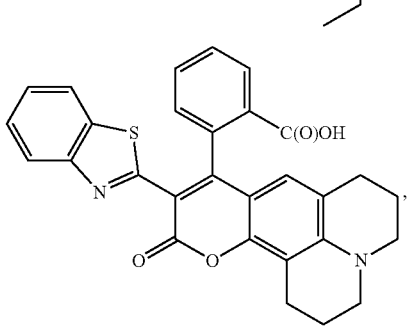
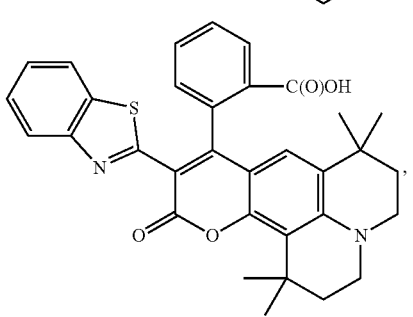

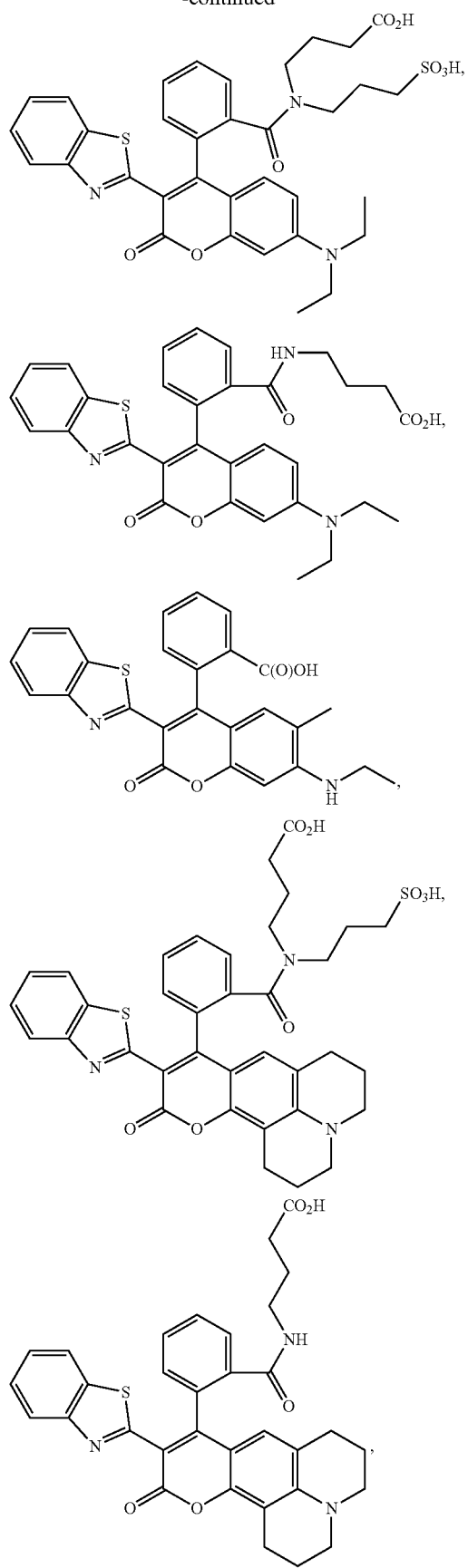
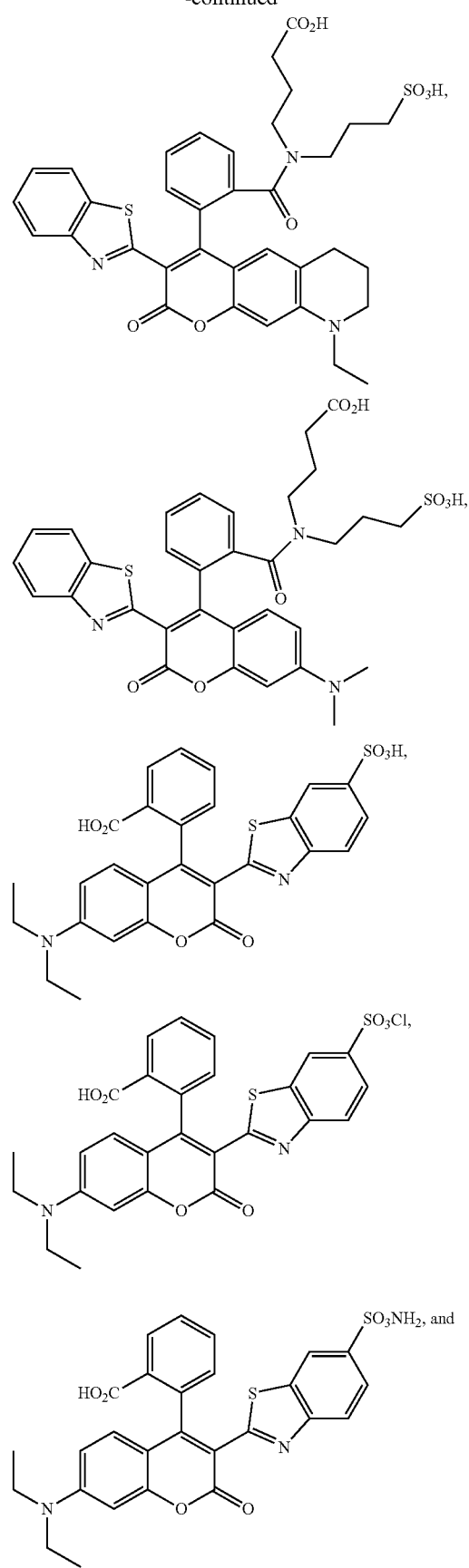

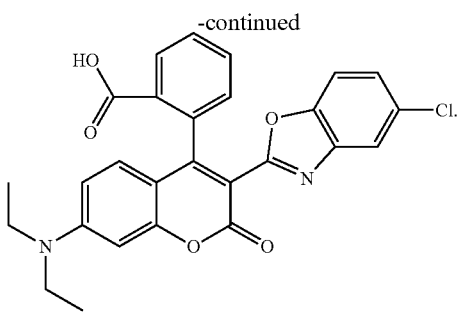

Additional exemplary dye compounds are disclosed in U.S. provisional application No. 63/057,758, which is incorporated by reference.

Synthesis of COT Bonded Dyes

Some aspect of the present disclosure relates to a method of protecting a fluorescent dye from photo-bleaching, comprising covalently attaching the fluorescent dye to a COT moiety comprising of the structure of formula (I), (Ia), (Ib), (Ic) or (Id) as described herein. Some further aspect of the present disclosure relate to a method of protecting a nucleoside or nucleotide from light-induced degradation, comprising covalently attaching the nucleoside or nucleotide to a fluorescent compound comprising a COT moiety of the structure of formula (I), (Ia), (Ib), (Ic) or (Id) as described herein.

The fluorescent dyes described herein may be covalently linked to a COT moiety via various methods. For example, a COT moiety may be introduced to a fluorescent compound by reacting a substituted COT compound containing an amino-reactive functional group, for example, with carboxyl group (—CO$_2$H), sulfo (—SO$_3$H) or sulfonate group (—SO$_3$⁻) of a fluorescent compound.

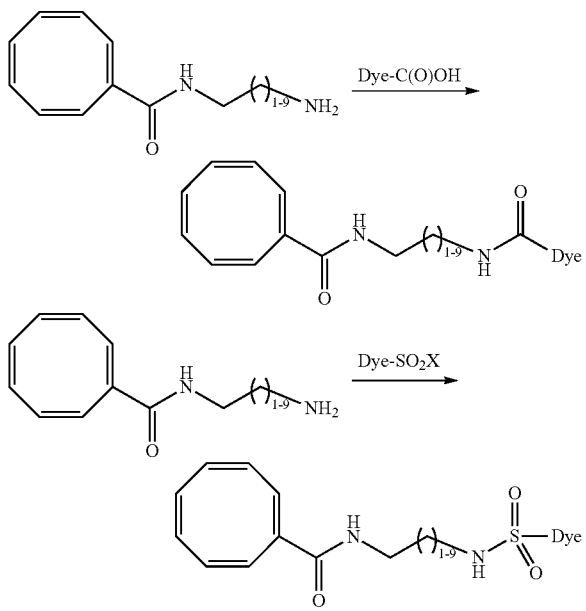

In other examples, COT moiety may be introduced to the fluorescent compound by reacting a carboxyl, sulfo, or sulfonate group of a COT moiety containing compound with an amino group of the dye.

Labeled Nucleotides

The COT moiety-bonded fluorescent compounds described herein are suitable for attachment to substrate moieties. Substrate moieties can be virtually any molecule or substance to which the fluorescent dyes described herein can be conjugated or adjoined and, by way of non-limiting example, may include nucleosides, nucleotides, polynucleotides, carbohydrates, ligands, particles, solid surfaces, organic and inorganic polymers and combinations or assemblages thereof, such as chromosomes, nuclei, living cells and the like. The dyes can be affixed by an optional linker by a variety of means including hydrophobic attraction, ionic attraction and covalent attachment. Particularly the dyes are conjugated to the substrate by covalent attachment. More particularly the covalent attachment is by means of a linker group. In some instances, such labeled nucleotides are also referred to as "modified nucleotides."

A particular useful application of the COT moiety-bonded fluorescent dyes as described herein is for labeling of biomolecules, for example, nucleotides or oligonucleotides. Some embodiments of the present application are directed to a nucleotide or oligonucleotide labeled with the fluorescent compounds as described herein.

Fluorescent dye molecules with appropriate spectral properties (such as Stokes shift, absorption and fluorescence intensity, position of absorption and fluorescence maxima and shape of absorption and fluorescence bands) can improve the speed and accuracy of nucleic acid sequencing. In some cases, Stokes Shift may be a key aspect in the detection of the fluorescence in biological applications. For example, the detection of emitted light can be difficult to distinguish from the excitation light when using fluorophores with absorption and fluorescence max very close to each other (i.e., small Stokes shift), because the excitation and emission wavelengths greatly overlap. In contrast, fluorophores with large Stokes shifts are easy to distinguish because of the greater separation between the excitation and emission wavelengths. The Stokes shift is especially critical in multiplex fluorescence applications, because the emission wavelength of one fluorophore may overlap, and therefore excite, another fluorophore in the same sample. In addition, fluorescence signal intensity is especially important when measurements are made in water based biological buffers and/or at higher temperature as fluorescence of most dyes is significantly lower at such conditions. Moreover, the nature of the base to which a dye is attached also affects the fluorescence maximum, fluorescence intensity and other spectral dye properties. The sequence specific interactions between the fluorescent dye and the nucleobase can be tailored by specific design of the fluorescent dyes. Optimization of the structure of the fluorescent dyes can adjust their fluorescent properties and also improve the efficiency of nucleotide incorporation, reduce the level of sequencing errors and decrease the usage of reagents in, and therefore the costs of, nucleic acid sequencing.

In some embodiments, the fluorescent compounds described herein may be covalently attached to oligonucleotides or nucleotides via the nucleotide base. For example, the labeled nucleotide or oligonucleotide may have the label attached to the C5 position of a pyrimidine base or the C7 position of a 7-deaza purine base through a linker moiety. The labeled nucleotide or oligonucleotide may also have a 3'-OH blocking group covalently attached to the ribose or deoxyribose sugar of the nucleotide.

In some embodiments, the covalently attached COT moiety as described herein does not change or substantially change the fluorescence properties (such as Stokes shift, fluorescence intensity, position of fluorescence maximum and shape of fluorescence band) of the dye.

3'-OH Blocking Groups

The labeled nucleotide or oligonucleotide may also have a blocking group covalently attached to the ribose or deoxyribose sugar of the nucleotide. The blocking group may be attached at any position on the ribose or deoxyribose sugar. In particular embodiments, the blocking group is at the 3'-OH position of the ribose or deoxyribose sugar of the nucleotide. Various 3'-OH blocking group are disclosed in WO2004/018497, WO2014/139596 and U.S. Pub. No. 2020/0216891, which are hereby incorporated by references. For example the blocking group may be azidomethyl (—CH$_2$N$_3$) or substituted azidomethyl (e.g., —CH(CHF$_2$)N$_3$ or CH(CH$_2$F)N$_3$), or allyl connecting to the 3' oxygen atom of the ribose or deoxyribose moiety. In some embodiments, the 3' blocking group is azidomethyl, forming 3'-OCH$_2$N$_3$ with the 3' carbon of the ribose or deoxyribose.

In some other embodiments, the 3' blocking group and the 3' oxygen atom form an acetal group of the structure

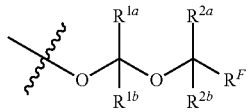

covalently attached to the 3' carbon of the ribose or deoxyribose, wherein:
- each $R^{1a}$ and $R^{1b}$ is independently H, $C_1$-$C_6$ alkyl, $C_1$-$C_6$ haloalkyl, $C_1$-$C_6$ alkoxy, $C_1$-$C_6$ haloalkoxy, cyano, halogen, optionally substituted phenyl, or optionally substituted aralkyl;
- each $R^{2a}$ and $R^{2b}$ is independently H, $C_1$-$C_6$ alkyl, $C_1$-$C_6$ haloalkyl, cyano, or halogen;
- alternatively, $R^{1a}$ and $R^{2a}$ together with the atoms to which they are attached form an optionally substituted five to eight membered heterocyclyl group;
- $R^F$ is H, optionally substituted $C_2$-$C_6$ alkenyl, optionally substituted $C_3$-$C_7$ cycloalkenyl, optionally substituted $C_2$-$C_6$ alkynyl, or optionally substituted ($C_1$-$C_6$ alkylene)Si($R^{3a}$)$_3$; and
- each $R^{1a}$ is independently H, $C_1$-$C_6$ alkyl, or optionally substituted $C_6$-$C_{10}$ aryl.

Additional 3'-OH blocking groups are disclosed in U.S. Publication No. 2020/0216891 A1, which is incorporated by reference in its entirety. Non-limiting examples of the acetal blocking group (AOM)

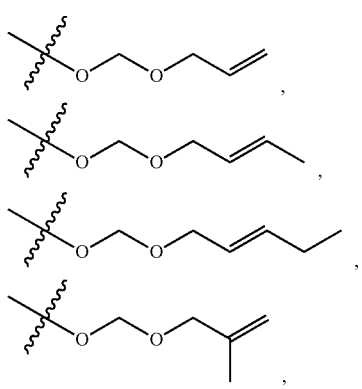

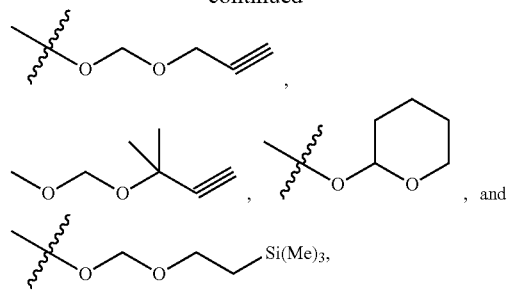

each covalently attached to the 3' carbon of the ribose or deoxyribose.

Deprotection of the 3'-OH Blocking Groups

In some embodiments, the azidomethyl 3'hydroxyl protecting group may be removed or deprotected by using a water soluble phosphine reagent. Non-limiting examples include tris(hydroxymethyl)phosphine (THMP), tris(hydroxyethyl)phosphine (THEP) or tris(hydroxylpropyl)phosphine (THP or THPP). 3'-acetal blocking groups described herein may be removed or cleaved under various chemical conditions. For acetal blocking groups

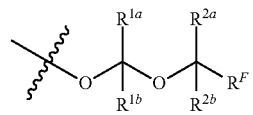

that contain a vinyl or alkenyl moiety, non-limiting cleaving condition includes a Pd(II) complex, such as Pd(OAc)$_2$ or allylPd(II) chloride dimer, in the presence of a phosphine ligand, for example tris(hydroxymethyl)phosphine (THMP), or tris(hydroxylpropyl)phosphine (THP or THPP). For those blocking groups containing an alkynyl group (e.g., an ethynyl), they may also be removed by a Pd(II) complex (e.g., Pd(OAc)$_2$ or allyl Pd(II) chloride dimer) in the presence of a phosphine ligand (e.g., THP or THMP).

Palladium Cleavage Reagents

In some embodiments, the 3' hydroxyl blocking group described herein may be cleaved by a palladium catalyst. In some such embodiments, the Pd catalyst is water soluble. In some such embodiments, is a Pd(0) complex (e.g., Tris(3, 3',3"-phosphinidynetris(benzenesulfonato)palladium(0) nonasodium salt nonahydrate). In some instances, the Pd(0) complex may be generated in situ from reduction of a Pd(II) complex by reagents such as alkenes, alcohols, amines, phosphines, or metal hydrides. Suitable palladium sources include Na$_2$PdCl$_4$, Pd(CH$_3$CN)$_2$Cl$_2$, (PdCl(C$_3$H$_5$))$_2$, [Pd(C$_3$H$_5$)(THP)]Cl, [Pd(C$_3$H$_5$)(THP)$_2$]Cl, Pd(OAc)$_2$, Pd(Ph$_3$)$_4$, Pd(dba)$_2$, Pd(Acac)$_2$, PdCl$_2$(COD), and Pd(TFA)$_2$. In one such embodiment, the Pd(0) complex is generated in situ from Na$_2$PdCl$_4$. In another embodiment, the palladium source is allyl palladium(II) chloride dimer [(PdCl(C$_3$H$_5$))$_2$]. In some embodiments, the Pd(0) complex is generated in an aqueous solution by mixing a Pd(II) complex with a phosphine. Suitable phosphines include water soluble phosphines, such as tris(hydroxypropyl)phosphine (THP), tris(hydroxymethyl)phosphine (THMP), 1,3,5-triaza-7-phosphaadamantane (PTA), bis(p-sulfonatophenyl)phenylphosphine dihydrate potassium salt, tris(carboxyethyl)phosphine (TCEP), and triphenylphosphine-3,3',3"-trisulfonic acid trisodium salt.

In some embodiments, the Pd(0) is prepared by mixing a Pd(II) complex [(PdCl($C_3H_5$))$_2$] with THP in situ. The molar ratio of the Pd(II) complex and the THP may be about 1:2, 1:3, 1:4, 1:5, 1:6, 1:7, 1:8, 1:9, or 1:10. In some further embodiments, one or more reducing agents may be added, such as ascorbic acid or a salt thereof (e.g., sodium ascorbate). In some embodiments, the cleavage mixture may contain additional buffer reagents, such as a primary amine, a secondary amine, a tertiary amine, a carbonate salt, a phosphate salt, or a borate salt, or combinations thereof. In some further embodiments, the buffer reagent comprises ethanolamine (EA), tris(hydroxymethyl)aminomethane (Tris), glycine, sodium carbonate, sodium phosphate, sodium borate, 2-dimethylethanolamine (DMEA), 2-diethylethanolamine (DEEA), N,N,N',N'-tetramethylethylenediamine(TEMED), or N,N,N',N'-tetraethylethylenediamine (TEEDA), or combinations thereof. In one embodiment, the buffer reagent is DEEA. In another embodiment, the buffer reagent contains one or more inorganic salts such as a carbonate salt, a phosphate salt, or a borate salt, or combinations thereof. In one embodiment, the inorganic salt is a sodium salt.

Linkers

The dye compounds as disclosed herein may include a reactive linker group at one of the substituent positions for covalent attachment of the compound to a substrate or another molecule. Reactive linking groups are moieties capable of forming a bond (e.g., a covalent or non-covalent bond), in particular a covalent bond. In a particular embodiment the linker may be a cleavable linker. Use of the term "cleavable linker" is not meant to imply that the whole linker is required to be removed. The cleavage site can be located at a position on the linker that ensures that part of the linker remains attached to the dye and/or substrate moiety after cleavage. Cleavable linkers may be, by way of non-limiting example, electrophilically cleavable linkers, nucleophilically cleavable linkers, photocleavable linkers, cleavable under reductive conditions (for example disulfide or azide containing linkers), oxidative conditions, cleavable via use of safety-catch linkers and cleavable by elimination mechanisms. The use of a cleavable linker to attach the dye compound to a substrate moiety ensures that the label can, if required, be removed after detection, avoiding any interfering signal in downstream steps.

Useful linker groups may be found in PCT Publication No. WO2004/018493 (herein incorporated by reference), examples of which include linkers that may be cleaved using water-soluble phosphines or water-soluble transition metal catalysts formed from a transition metal and at least partially water-soluble ligands. In aqueous solution the latter form at least partially water-soluble transition metal complexes. Such cleavable linkers can be used to connect bases of nucleotides to labels such as the dyes set forth herein.

Particular linkers include those disclosed in PCT Publication No. WO2004/018493 (herein incorporated by reference) such as those that include moieties of the formulae:

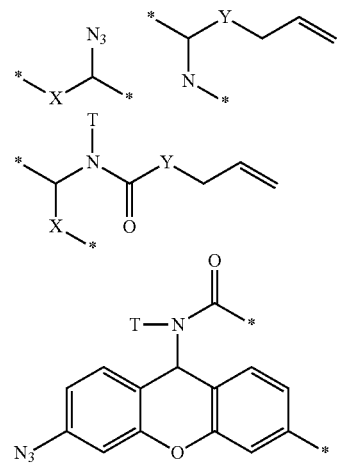

(wherein X is selected from the group comprising O, S, NH and NQ wherein Q is a $C_{1-10}$ substituted or unsubstituted alkyl group, Y is selected from the group comprising O, S, NH and N(allyl), T is hydrogen or a $C_1$-$C_{10}$ substituted or unsubstituted alkyl group and * indicates where the moiety is connected to the remainder of the nucleotide or nucleoside). In some aspects, the linkers connect the bases of nucleotides to labels such as, for example, the dye compounds described herein.

Additional examples of linkers include those disclosed in U.S. Publication No. 2016/0040225 (herein incorporated by reference), such as those include moieties of the formulae:

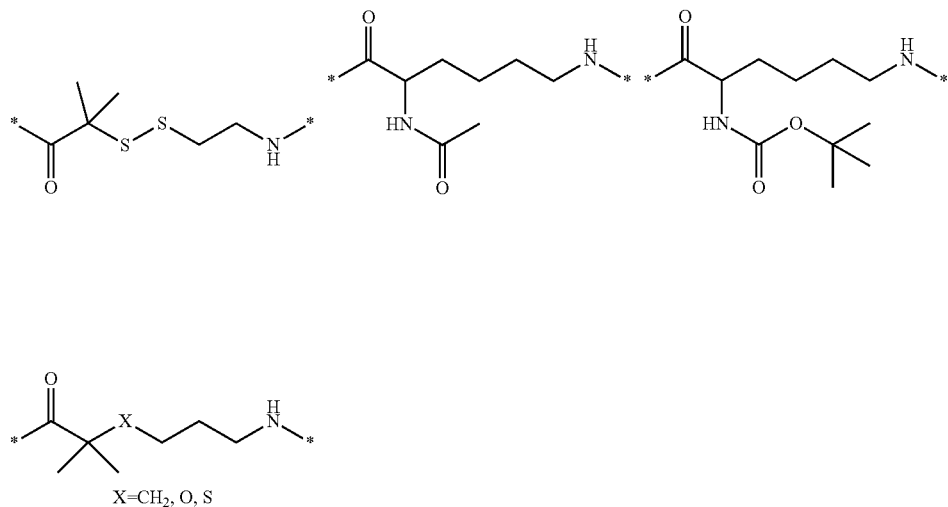

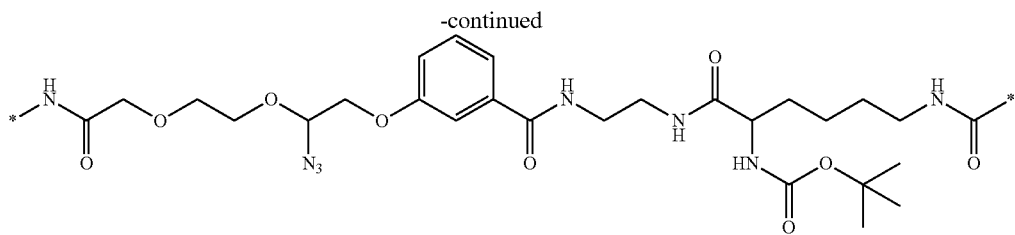

(wherein * indicates where the moiety is connected to the remainder of the nucleotide or nucleoside). The linker moieties illustrated herein may comprise the whole or partial linker structure between the nucleotides/nucleosides and the labels.

Additional examples of linkers include those disclosed in U.S. Publication Nos. 2019/0017111 and 2020/0216891 (herein incorporated by reference), such as those include moieties of the formula:

In particular embodiments, the length of the linker between a fluorescent dye (fluorophore) and a nucleobase, for example a substituted guanine base can be altered, for example, by introducing a polyethylene glycol spacer group, thereby increasing the fluorescence intensity compared to the same fluorophore attached to the guanine base through other linkages known in the art. Exemplary linkers and their properties are set forth in PCT Publication No. WO2007020457 (herein incorporated by reference). The

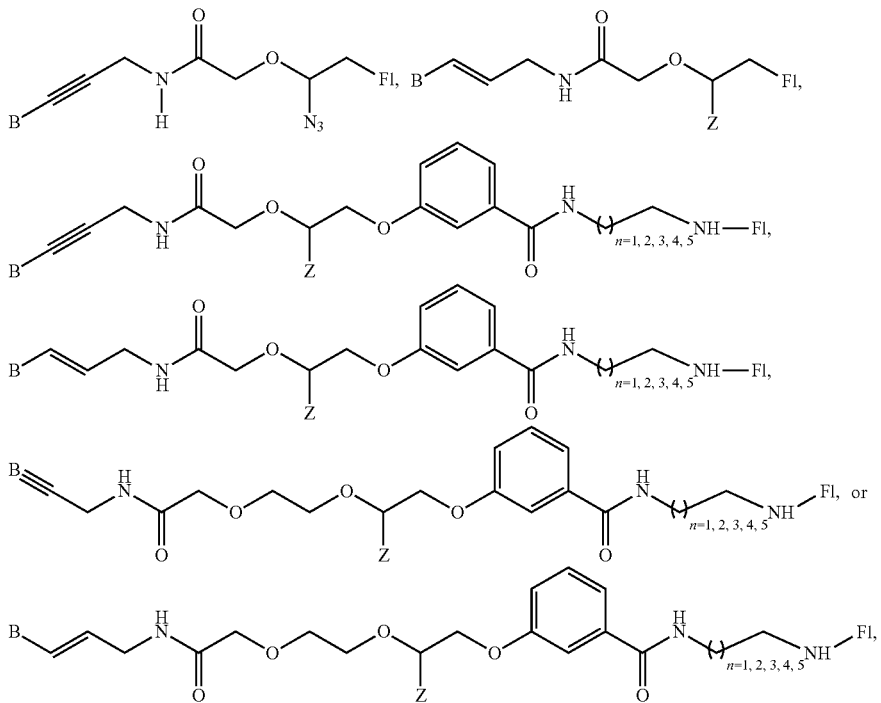

wherein B is a nucleobase; Z is —N$_3$ (azido), —O—C$_1$-C$_6$ alkyl, —O—C$_2$-C$_6$ alkenyl, or —O—C$_2$-C$_6$ alkynyl; and Fl comprises a dye moiety, which may contain additional linker structure. One of ordinary skill in the art understands that the dye compound described herein is covalently bounded to the linker by reacting a functional group of the dye compound (e.g., carboxyl) with a functional group of the linker (e.g., amino). In one embodiment, the cleavable linker comprises

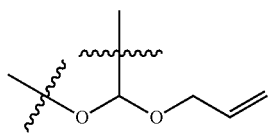 [SMILES: *OC(*)OCC=C]

("AOL" linker moiety) where Z is —O-allyl.

design of linkers, and especially their increased length, can allow improvements in the brightness of fluorophores attached to the guanine bases of guanosine nucleotides when incorporated into polynucleotides such as DNA. Thus, when the dye is for use in any method of analysis which requires detection of a fluorescent dye label attached to a guanine-containing nucleotide, it is advantageous if the linker comprises a spacer group of formula —((CH$_2$)$_2$O)$_n$—, wherein n is an integer between 2 and 50, as described in WO 2007/020457.

Nucleosides and nucleotides may be labeled at sites on the sugar or nucleobase. As known in the art, a "nucleotide" consists of a nitrogenous base, a sugar, and one or more phosphate groups. In RNA, the sugar is ribose and in DNA is a deoxyribose, i.e., a sugar lacking a hydroxyl group that is present in ribose. The nitrogenous base is a derivative of purine or pyrimidine. The purines are adenine (A) and guanine (G), and the pyrimidines are cytosine (C) and thymine (T) or in the context of RNA, uracil (U). The C-1 atom of deoxyribose is bonded to N-1 of a pyrimidine or N-9 of a purine. A nucleotide is also a phosphate ester of a nucleoside, with esterification occurring on the hydroxyl group attached to the C-3 or C-5 of the sugar. Nucleotides are usually mono, di- or triphosphates.

A "nucleoside" is structurally similar to a nucleotide but is missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogues are available which do not alter the capability of the nucleotide or nucleoside to undergo Watson-Crick base pairing. "Derivative" or "analogue" means a compound or molecule whose core structure is the same as, or closely resembles that of a parent compound, but which has a chemical or physical modification, such as, for example, a different or additional side group, which allows the derivative nucleotide or nucleoside to be linked to another molecule. For example, the base may be a deazapurine. In particular embodiments, the derivatives should be capable of undergoing Watson-Crick pairing. "Derivative" and "analogue" also include, for example, a synthetic nucleotide or nucleoside derivative having modified base moieties and/or modified sugar moieties. Such derivatives and analogues are discussed in, for example, Scheit, *Nucleotide analogs* (John Wiley & Son, 1980) and Uhlman et al., *Chemical Reviews* 90:543-584, 1990. Nucleotide analogues can also comprise modified phosphodiester linkages including phosphorothioate, phosphorodithioate, alkyl-phosphonate, phosphoranilidate, phosphoramidate linkages and the like.

The fluorescent dye may be attached to any position on the nucleotide base, through a linker, provided that Watson-Crick base pairing can still be carried out. Particular nucleobase labeling sites include the C5 position of a pyrimidine base or the C7 position of a 7-deaza purine base. As described above a linker group may be used to covalently attach a dye to the nucleoside or nucleotide.

In particular embodiments the labeled nucleoside or nucleotide may be enzymatically incorporable and enzymatically extendable. Accordingly a linker moiety may be of sufficient length to connect the nucleotide to the compound such that the compound does not significantly interfere with the overall binding and recognition of the nucleotide site of a nucleic acid replication enzyme. Thus, the linker can also comprise a spacer unit. The spacer distances, for example, the nucleotide base from a cleavage site or label.

Nucleosides or nucleotides labeled with the COT moiety-bonded fluorescent dyes described herein may have the formula:

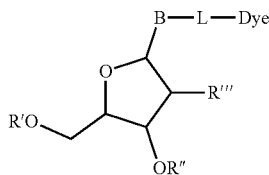

where Dye is a dye compound containing a covalently bonded COT moiety comprising the structure of formula (I), (Ia), (Ib), (Ic) or (Id); B is a nucleobase, such as, for example uracil, thymine, cytosine, adenine, 7-deaza adenine, guanine, 7-deaza guanine, and the like; and L is an optional linker group which may or may not be present. R' can be H, or —OR' is monophosphate, diphosphate, triphosphate, thiophosphate, a phosphate ester analog, —O— attached to a reactive phosphorous containing group or —O— protected by a blocking group. R" can be H, a phosphoramidite, or a 3'-OH blocking group; and R'" is H or OH; where R" is phosphoramidite, R' is an acid-cleavable hydroxyl protecting group which allows subsequent monomer coupling under automated synthesis conditions.

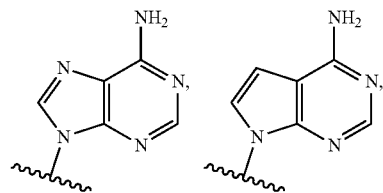

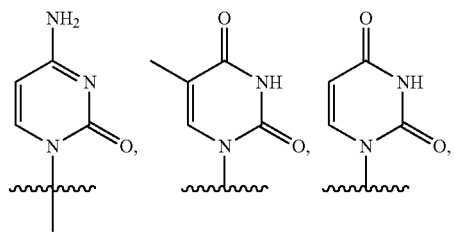

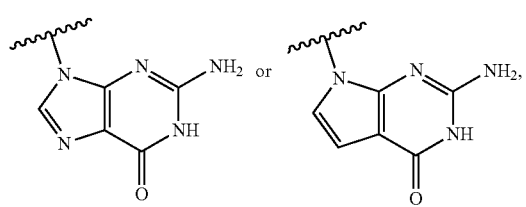

In some further embodiments, B comprises or optionally substituted derivatives and analogs thereof. In some further embodiments, the labeled nucleobase comprises the structure

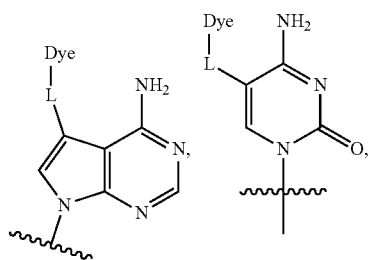

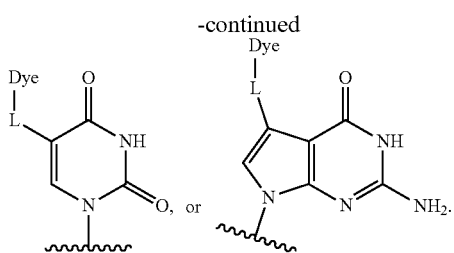

In some instances, the blocking group is separate and independent of the dye compound, i.e. not attached to it. Alternatively, the dye may comprise all or part of the 3'-OH blocking group. Thus R" can be a 3'-OH blocking group which may or may not comprise the dye compound. In additional alternative embodiments, there is no blocking group on the 3' carbon of the pentose sugar and the dye (or dye and linker construct) attached to the base, for example, can be of a size or structure sufficient to act as a block to the incorporation of a further nucleotide from a point other than the 3' site. Thus the block can be due to steric hindrance or can be due to a combination of size, charge and structure.

The use of a blocking group allows polymerization to be controlled, such as by stopping extension when a labeled nucleotide is incorporated. If the blocking effect is reversible, for example by way of non-limiting example by changing chemical conditions or by removal of a chemical block, extension can be stopped at certain points and then allowed to continue. Non-limiting examples of 3'-OH blocking groups include those disclosed in WO 2004/018497 and WO2014/139596, and U.S. Publication No. 2020/0216891, which are hereby incorporated by references. For example the blocking group may be azidomethyl (—CH$_2$N$_3$) or substituted azidomethyl (e.g., —CH(CHF$_2$)N$_3$ or CH(CH$_2$F)N$_3$), allyl, or (AOM)

In a particular embodiment the linker and blocking group are both present and are separate moieties which are both cleavable under substantially similar conditions. Thus, deprotection and deblocking processes may be more efficient since only a single treatment will be required to remove both the dye compound and the blocking group.

The present disclosure also directs to encompassing polynucleotides incorporating dye compounds described herein. Such polynucleotides may be DNA or RNA comprised respectively of deoxyribonucleotides or ribonucleotides joined in phosphodiester linkage. Polynucleotides may comprise naturally occurring nucleotides, non-naturally occurring (or modified) nucleotides other than the labeled nucleotides described herein or any combination thereof, provided that at least one nucleotide labeled with a COT moiety containing fluorescent dye is present. Polynucleotides may also include non-natural backbone linkages and/or non-nucleotide chemical modifications. Chimeric structures comprised of mixtures of ribonucleotides and deoxyribonucleotides comprising at least one labeled nucleotide are also contemplated.

Non-limiting exemplary labeled nucleotides as described herein include the following structures. "Dye" as shown in each of the structure may refer to either the covalently bonded COT moiety containing fluorescent compounds as described herein, or fluorescent compounds without COT moiety, such as those of Formula (A), (B), (C) or (D).

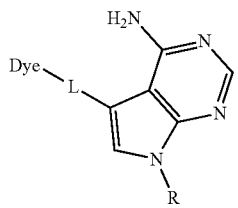

A

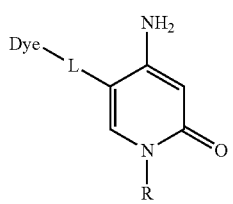

C

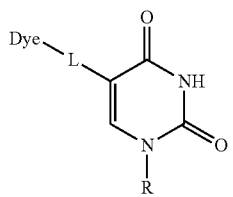

T

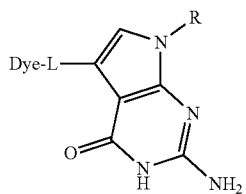

G

57
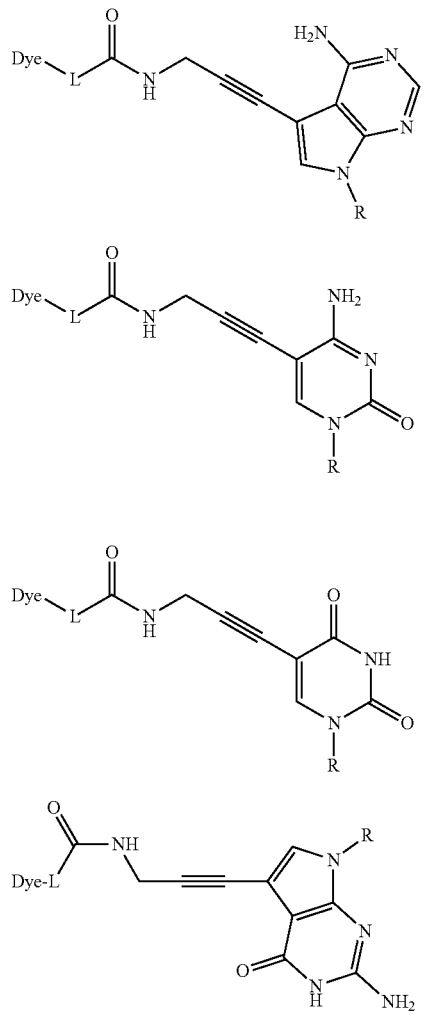
A
C
T
G
58
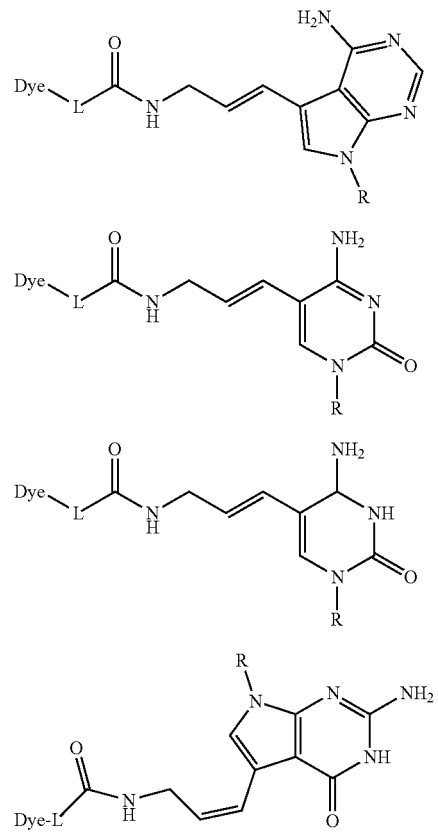
A
C
T
G
wherein: L represents a linker and R represents a ribose or deoxyribose moiety as described above, or a ribose or deoxyribose moiety with the 5' position substituted with mono-, di- or tri-phosphates. In some embodiments, non-limiting exemplary fluorescent dye conjugates are shown below.
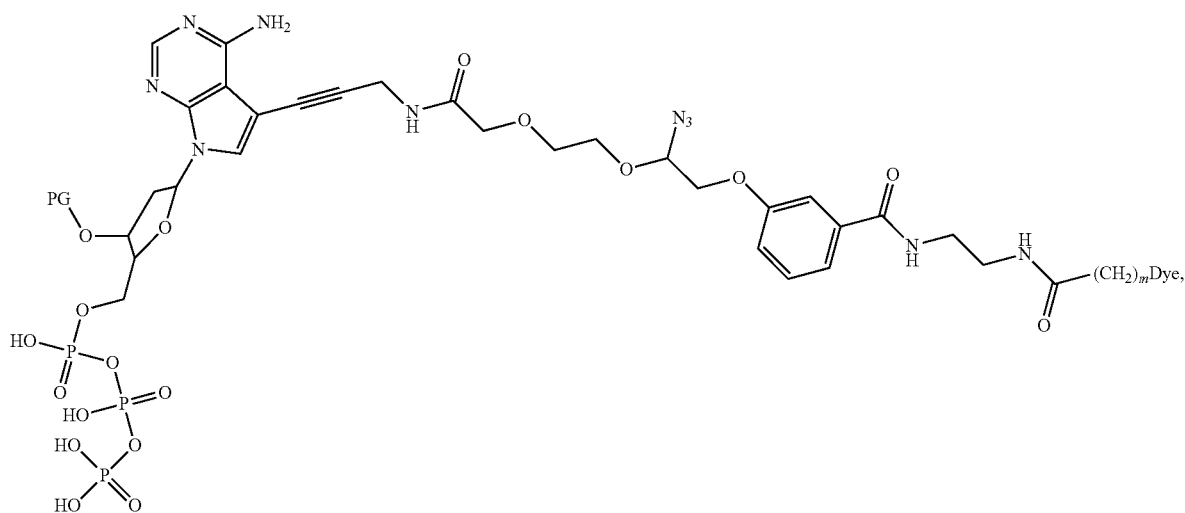
ffA-LN3-Dye -continued
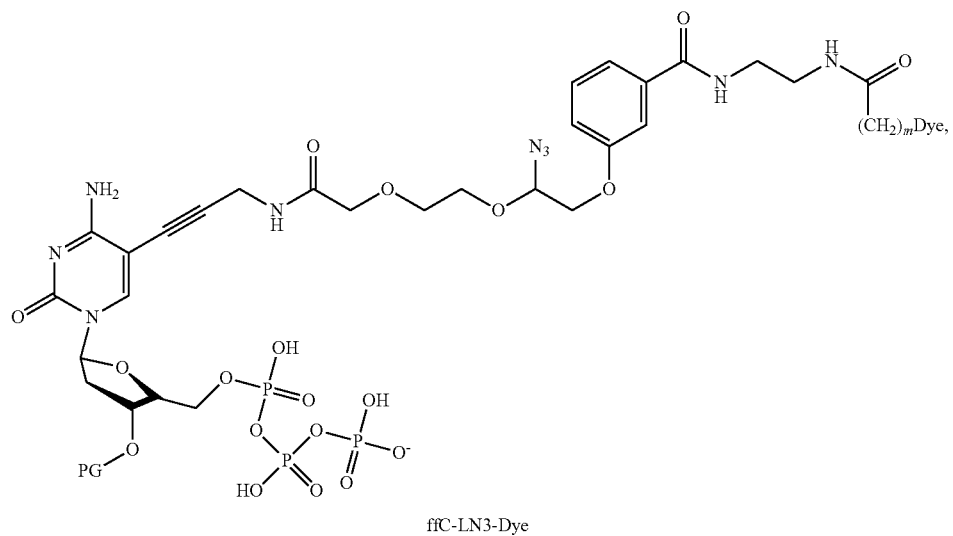
ffC-LN3-Dye
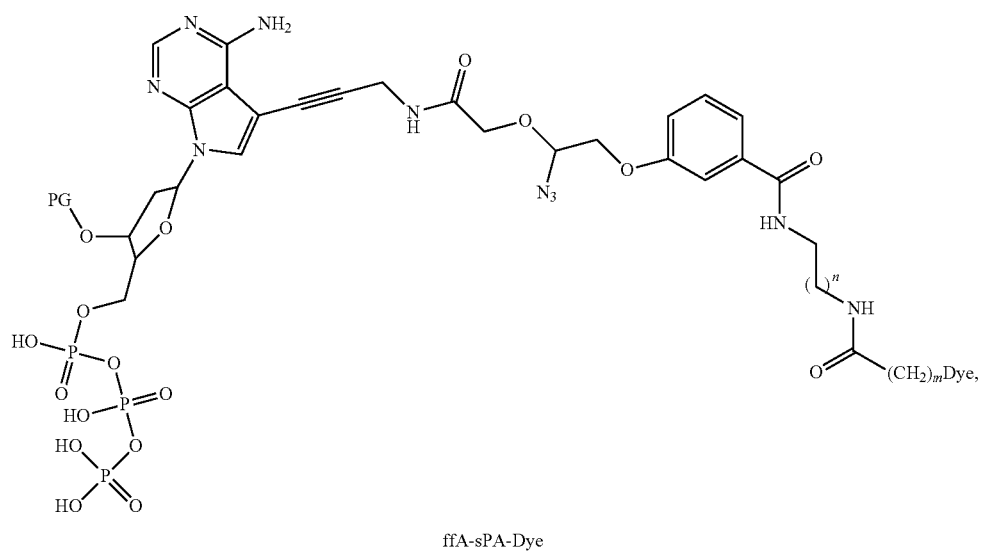
ffA-sPA-Dye
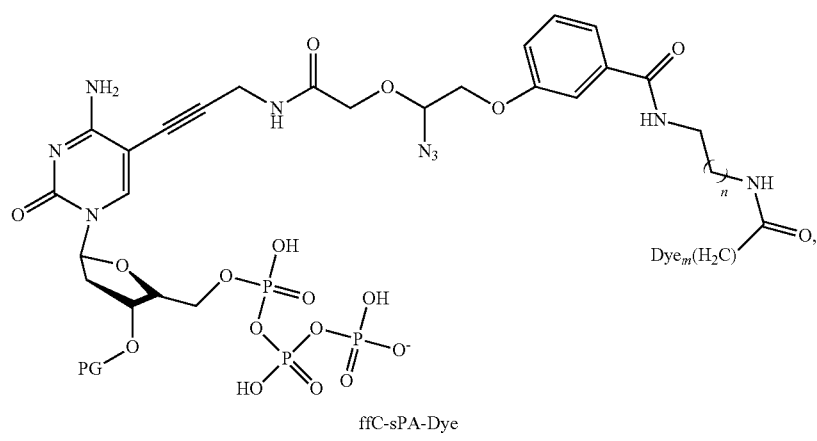
ffC-sPA-Dye -continued
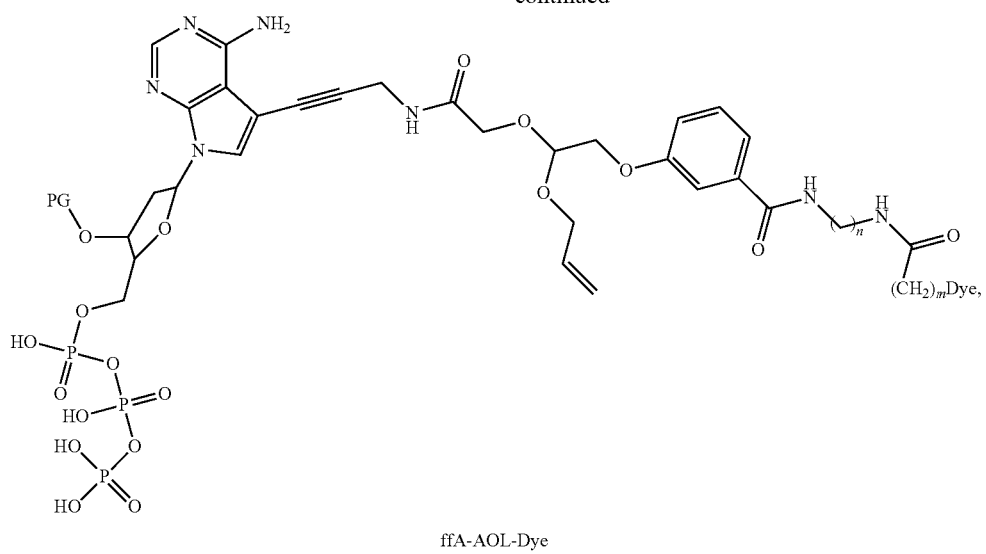
ffA-AOL-Dye
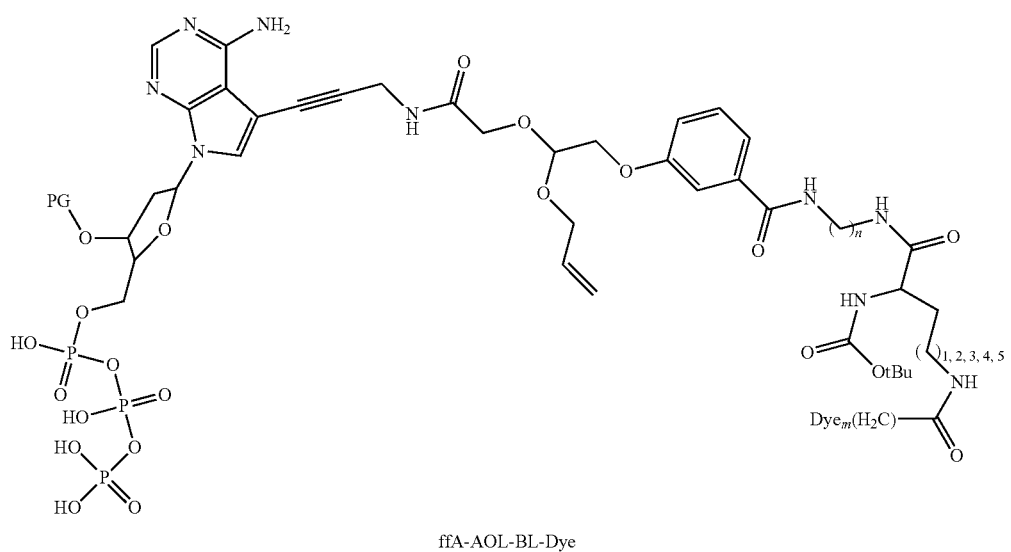
ffA-AOL-BL-Dye
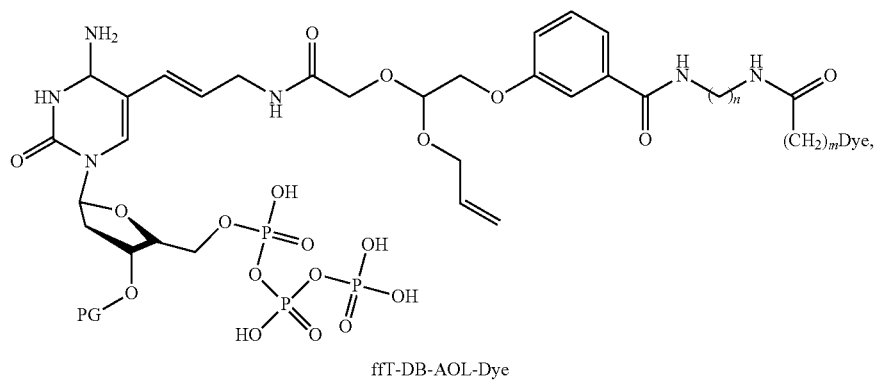
ffT-DB-AOL-Dye

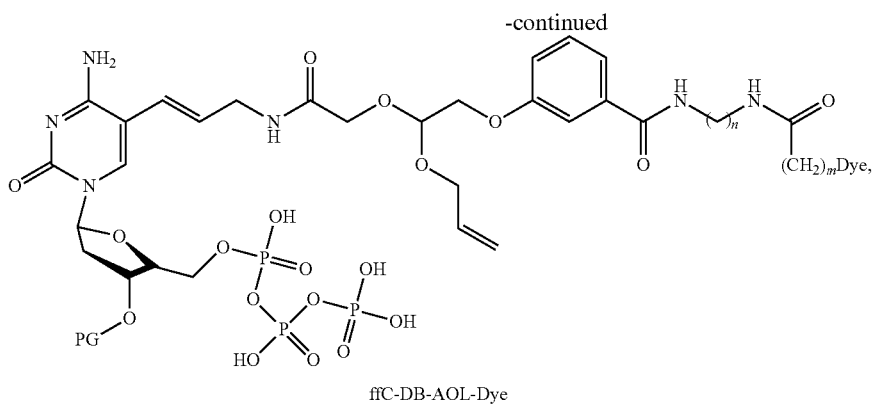

ffC-DB-AOL-Dye

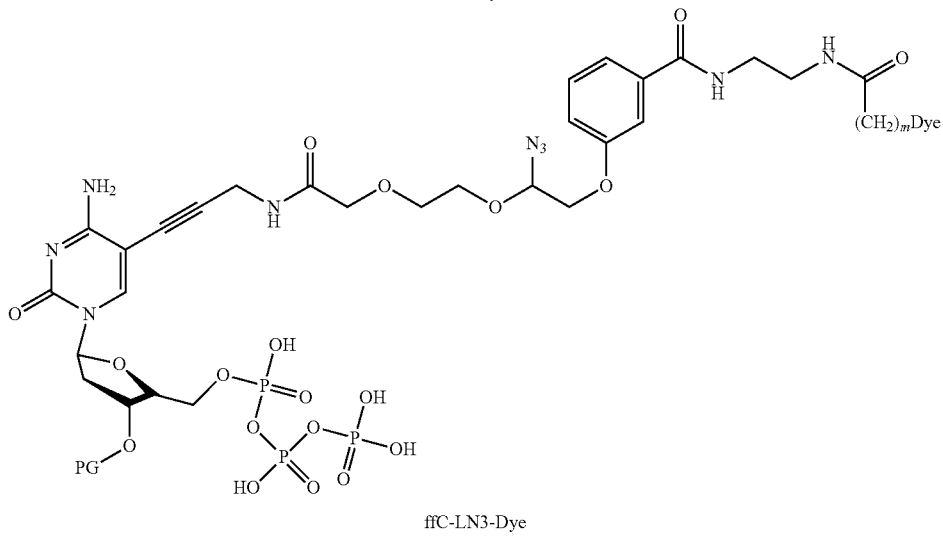

ffC-LN3-Dye wherein PG stands for the 3' OH blocking groups described herein; n is an integer of 1, 2, 3, 4, 5, 6, 7, 8, 9, or 10; and m is 0, 1, 2, 3, 4, or 5. In one embodiment, —O-PG is AOM. In another embodiment, —O-PG is —O-azidomethyl. In one embodiment, n is 5.

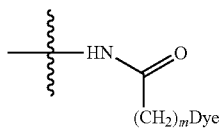

refers to the connection point of the Dye with the cleavable linker as a result of a reaction between an amino group of the linker moiety and the carboxyl group of the Dye. In each structure, when m is 0, the carboxyl group of the dye is directed attached to the ffN linker by reacting with an amino moiety of the linker to form an amide bond. In some instances, the linker "sPA" is also known as "sPA-LN3".

In any embodiments of the labeled nucleotide described herein, the nucleotide is a nucleotide triphosphate.

Additional aspects of the present disclosure relate to an oligonucleotide comprising a labeled nucleotide described herein. In some embodiments, the oligonucleotide is hybridized to at least a portion of a target polynucleotide. In some embodiments, the target polynucleotide is immobilized on a solid support. In some further embodiments, the solid support comprises an array of a plurality of immobilized target polynucleotides.

Kits

Some embodiments disclosed herein are kits including nucleosides and/or nucleotides labeled with the COT modified fluorescent dyes described herein. Such kits will generally include at least one nucleotide or nucleoside labeled with a dye together with at least one further component. The further component(s) may be further labeled or unlabeled nucleotides or nucleosides. For example, nucleotides labeled with dyes may be supplied in combination with unlabeled or native nucleotides, and/or with fluorescently labeled nucleotides or any combination thereof. Combinations of nucleotides may be provided as separate individual components or as nucleotide mixtures. In some embodiments, the kits comprise one or more nucleotides wherein at least one nucleotide is a nucleotide labeled with a COT moiety-bonded fluorescent compound described herein. The kits may comprise two or more labeled nucleotides. The nucleotides may be labeled with two or more fluorescent labels. Two or more of the labels may be excited using a single excitation source, which may be a laser.

The kits may contain four labeled nucleotides (e.g., A, C, T, G), where the first of four nucleotides is labeled with a COT modified fluorescent compound as disclosed herein, and the second, third, and fourth nucleotides are each may be labeled with a different fluorescent compound (each may also be COT modified), wherein each fluorescent compound has a distinct fluorescence maximum and each of the fluorescent compounds is distinguishable from the other three compounds. The kits may be such that two or more of the fluorescent compounds have a similar absorbance maximum but different Stokes shift.

The COT modified fluorescent compounds, nucleotides labeled with the COT modified compounds or kits described herein may be used in sequencing, expression analysis, hybridization analysis, genetic analysis, RNA analysis or protein binding assays. The use may be on an automated sequencing instrument. The sequencing instrument may contain two lasers operating at different wavelengths.

Where kits comprise a plurality, particularly two, more particularly four, nucleotides labeled with a dye compound, the different nucleotides may be labeled with different dye compounds, or one may be dark, with no dye compounds. Where the different nucleotides are labeled with different dye compounds it is a feature of the kits that said dye compounds are spectrally distinguishable fluorescent dyes. As used herein, the term "spectrally distinguishable fluorescent dyes" refers to fluorescent dyes that emit fluorescent energy at wavelengths that can be distinguished by fluorescent detection equipment (for example, a commercial capillary based DNA sequencing platform) when two or more such dyes are present in one sample. When two nucleotides labeled with fluorescent dye compounds are supplied in kit form, the spectrally distinguishable fluorescent dyes can be excited at the same wavelength, such as, for example by the same laser in some embodiments. When four nucleotides labeled with fluorescent dye compounds are supplied in kit form, two of the spectrally distinguishable fluorescent dyes can both be excited at one wavelength and the other two spectrally distinguishable dyes can both be excited at another wavelength in some embodiments. Particular excitation wavelengths are about 460 nm.

In some embodiments, at least one nucleotide may be labelled with a dye which excitable with two lasers with different wavelength.

In one embodiment a kit comprises a nucleotide labeled with a COT modified dye described herein and a second nucleotide labeled with a second dye wherein the dyes have a difference in absorbance maximum of at least 10 nm, particularly 20 nm to 50 nm. More particularly the two dye compounds have Stokes shifts of between 15-40 nm or between 20-40 nm. As used herein, the term "Stokes shift" is the distance between the peak absorption and peak emission wavelengths.

In a further embodiment said kit further comprises two other nucleotides labeled with fluorescent dyes wherein said dyes are may be excited by the light sources with emission at about 440 nm to about 560 nm.

In an alternative embodiment, the kits may contain nucleotides where the same base is labeled with two different compounds. A first nucleotide may be labeled with COT modified dye described herein. A second nucleotide may be labeled with a spectrally distinct dye, for example a 'red' dye absorbing at greater than 600 nm. A third nucleotide may be labeled as a mixture of the COT modified dye described herein and the spectrally distinct dye, and the fourth nucleotide may be 'dark' and contain no label. In simple terms therefore the nucleotides 1-4 may be labeled 'green', 'red', 'red/green', and dark. To simplify the instrumentation further, four nucleotides can be labeled with a two dyes excited with a single light source, and thus the labeling of nucleotides 1-4 may be 'green 1', 'green 2' 'green 1/green 2', and dark.

In other embodiments the kits may include a polymerase enzyme capable of catalyzing incorporation of the nucleotides into a polynucleotide. Other components to be included in such kits may include buffers and the like. The nucleotides labeled with the COT moiety-bonded fluorescent dyes described herein, and other any nucleotide components including mixtures of different nucleotides, may be provided in the kit in a concentrated form to be diluted prior to use. In such embodiments a suitable dilution buffer may also be included.

Some additional embodiments of the present disclosure relates to a kit for use with a sequencing apparatus, comprising a plurality of chambers containing a plurality of compositions, wherein each chamber contains a single composition, wherein the plurality of compositions comprise: reagents for incorporating a nucleotide into a copy polynucleotide strand complementary to at least a portion of a template polynucleotide strand, wherein the nucleotide comprises a 3' blocking group and is labeled with a COT modified fluorescent compound comprising the structure of formula (I), (Ia), (Ib), (Ic) or (Id) as described herein; a buffer composition comprising at least one antioxidant; reagents for chemically removing a label and blocking moiety from the blocked, labeled nucleotide incorporated into the copy strand; and a wash solution. In some embodiments, the fluorescent compound is a blue dye. In some further embodiments, the fluorescent compound is exemplified as Formulas (A), (B), (C) and (D). In some embodiments, the buffer solution may comprises, COT, quercetin, ascorbic acid, or sodium ascorbate, gallic acid derivatives or combinations thereof. In some further embodiments, the buffer composition may also comprises a scavenger, for example, a compound with a disulfide or an azido moiety, lipoic acid or 3,3'-dithiodipropionic acid (DDPA). In some embodiments, the reagents for incorporating a nucleotide into the polynucleotide strand include a polymerase. In some embodiments, the reagents for chemically removing a label and blocking moiety of the incorporated nucleotide comprises a phosphine, such as a trialkylphosphine. None-limiting examples of trialkylphosphines include tris(3-hydroxypropyl)phosphine (THP), tris-(2-carboxyethyl)phosphine (TCEP), tris(hydroxymethyl)phosphine (THMP), or tris(2-hydroxyethyl)phosphine (THEP). In some embodiments, the 3'blocking group contains an azido group (e.g., azidomethyl). In some embodiments, the wash solution may also comprises a ROS or radical scavenger(s).

Some additional embodiments of the present disclosure relates to a kit for use with a sequencing apparatus, comprising a plurality of chambers containing a plurality of compositions, wherein each chamber contains a single composition, wherein the plurality of compositions comprise: reagents for incorporating a 3' blocked, labeled nucleotide into a copy polynucleotide strand complementary to at least a portion of a template polynucleotide strand; a buffer composition comprising a composition containing cyclooctatetraene as described herein; reagents for chemically removing a label and blocking moiety from the blocked, labeled nucleotide incorporated into the copy strand; and a wash solution. In some embodiments, the buffer composition may also comprises quercetin, ascorbic acid, or sodium ascorbate, gallic acid derivatives or combinations thereof. In some further embodiments, the buffer composition may also comprises a ROS or/and radical scavenger, for example, a compound with a disulfide or an azido moiety, lipoic acid or 3,3'-dithiodipropionic acid (DDPA). In some embodiments, the reagents for incorporating a nucleotide into the polynucleotide strand include a polymerase. In some embodiments, the reagents for chemically removing a label and blocking moiety of the incorporated nucleotide comprises a phosphine, such as a trialkylphosphine. None-limiting examples of trialkylphosphines include tris(3-hydroxypropyl)phosphine (THP), tris-(2-carboxyethyl)phosphine (TCEP), tris(hydroxymethyl)phosphine (THMP), or tris(2-hydroxyethyl)phosphine (THEP). In some embodiments, the 3'blocking group contains an azido group (e.g., azidomethyl). In some embodiments, the wash solution may also comprises a scavenger.

Methods of Sequencing

Nucleotides (or nucleosides) comprising a COT moiety-bonded fluorescent dye described herein may be used in any method of analysis which requires detection of a fluorescent label attached to a nucleotide or nucleoside, whether on its own or incorporated into or associated with a larger molecular structure or conjugate. Some embodiments of the present application are directed to methods of sequencing including: (i) incorporating at least one labeled nucleotide as described herein into a polynucleotide; and (ii) detecting the labeled nucleotide(s) incorporated into the polynucleotide by detecting the fluorescent signal from the COT moiety-bonded fluorescent dye attached to said nucleotide(s).

In some embodiments, at least one labeled nucleotide is incorporated into a polynucleotide in the synthetic step by the action of a polymerase enzyme. However, other methods of incorporating labeled nucleotides to polynucleotides, such as chemical oligonucleotide synthesis or ligation of labeled oligonucleotides to unlabeled oligonucleotides, are not excluded. Therefore, the term "incorporating" a nucleotide into a polynucleotide encompasses polynucleotide synthesis by chemical methods as well as enzymatic methods.

Some specific embodiments of the present disclosure relates to a method of reducing or preventing light-induced degradation of nucleic acids during a nucleic acid sequencing reaction, comprising:
(a) incorporating a nucleotide into a copy polynucleotide strand complementary to at least a portion of a template polynucleotide strand, wherein the nucleotide comprises a label and a 3' blocking group;
(b) detecting the identity of the nucleotide incorporated into the copy strand in the presence of a first buffer composition;
(c) chemically removing the label and the 3' blocking group from the nucleotide incorporated into the copy polynucleotide strand; and
(d) washing the chemically removed label and the 3' blocking group away from the copy strand with a wash solution; wherein the first buffer composition comprises cyclooctatetraene or an optionally substituted derivative thereof, and one or more antioxidants selected from the group consisting of taxifolin, quercetin, allyl thiourea, dimethyl thiourea, silibinin, and trolox, and optionally substituted derivatives and combinations thereof.

In some embodiments of the method described herein, the buffer composition may also comprises quercetin, ascorbic acid, or sodium ascorbate, gallic acid or its derivatives, or combinations thereof. In some further embodiment, the buffer composition comprises both cyclooctatetraene and quercetin, or optionally substituted derivatives thereof. In some further embodiments, cyclooctatetraene or the optionally substituted derivative is in a concentration from about 0.1 mM to about 100 mM, or from about 1 mM to about 50 mM, from about 2 mM to about 25 mM, from about 5 mM to about 15 mM, or about 10 mM. In some further embodiments, quercetin or the optionally substituted derivative is in a concentration from about 0.01 mM to about 10 mM, from about 0.02 mM to about 5 mM, from about 0.05 mM to about 2 mM, from about 0.1 mM to about 1 mM, from about 0.2 mM to about 0.5 mM, or about 0.25 mM.

Some additional embodiments provided herein relate to a method of reducing or preventing light-induced degradation of nucleic acids during a nucleic acid sequencing reaction, comprising:
(a) incorporating a nucleotide into a copy polynucleotide strand complementary to at least a portion of a template polynucleotide strand, wherein the nucleotide comprises a 3' blocking group and is labeled with a COT-modified fluorescent compound comprising the structure of formula (I), (Ia), (Ib), (Ic) or (Id) as described herein;
(b) detecting the identity of the nucleotide incorporated into the copy strand in the presence of a first buffer composition;
(c) chemically removing the label and the 3' blocking group from the nucleotide incorporated into the copy polynucleotide strand; and
(d) washing the chemically removed label and the 3' blocking group away from the copy strand with a wash solution.

In some embodiments of the sequencing methods described herein, the fluorescent compound is a blue dye. In some further embodiments, the fluorescent compound is exemplified as Formulas (A), (B), (C) and (D). In some embodiments, the buffer solution may comprises, ascorbic acid, or sodium ascorbate, or combinations thereof. In some further embodiments, the buffer composition may also comprises a scavenger, for example, a compound with a disulfide or an azido moiety, lipoic acid or 3,3'-dithiodipropionic acid (DDPA). In some embodiments, the reagents for incorporating a nucleotide into the polynucleotide strand include a polymerase. In some embodiments, the 3'blocking group contains an azido group (e.g., azidomethyl). In some embodiments, the wash solution may also comprises a scavenger. In some further embodiments, the wash solution comprises the first buffer solution. In some embodiments, steps (a) to (d) is repeated until a sequence of the portion of the template polynucleotide strand is determined. In some such embodiments, steps (a) to (d) is repeated at least 50 times, at least 75 times, at least 100 times, at least 125 times, or at least 150 times. In some embodiments, step (b) comprises performing one or more fluorescent measurements by irradiating the copy polynucleotide strand incorporated with the nucleotide with a light source in the presence of the first buffer composition. In some such embodiments, the light source has a wavelength from about 400 nm to about 500 nm. In some embodiments, removing the label and the 3' blocking group from the nucleotide incorporated into the copy polynucleotide strand comprises contacting the copy strand with a phosphine, such as a trialkylphosphine. None-limiting examples of trialkylphosphines include tris(3-hydroxypropyl)phosphine (THP), tris-(2-carboxyethyl)phosphine (TCEP), tris(hydroxymethyl)phosphine (THMP), or tris(2-hydroxyethyl)phosphine (THEP). In any embodiments of the methods described herein, the labeled nucleotide is a nucleotide triphosphate. In any embodiments of the method described herein, the template polynucleotide strand is attached to a solid support, such as a flow cell.

In some embodiments of the method described herein, the use of COT modified fluorescent compound as described herein as a nucleotide label in sequencing run may reduce the photobleaching or DNA damage caused by light irradiation by at least 5%, 10%, 15%, 20%, 25%, 30%, 35%, 40%, 45%, 50%, 55%, 60%, 65%, 70%, 75%, or 80%, as compared to the same fluorescent compound without COT modification. In some such embodiments, photobleaching or DNA damage is measured by the percent remaining fluorescent intensity after 10 minutes, 20 minutes, or 30 minutes light irradiation, or after 1, 10, 25, 50, 75, 100, 125 or 150 sequencing runs. In some such embodiments, the photobleaching is caused by a blue light having a wavelength between 450 nm to 460 nm. In some such embodiments, the fluorescent intensity is measured in a detection solution as described herein. In other embodiment, the fluorescent intensity is measured on a solid support surface, such as flow cell.

In some embodiments of the method described herein, the use of a buffer composition containing COT and quercetin as described herein in a detection solution during sequencing may reduce photobleaching or DNA damage caused by light irradiation by at least 5%, 10%, 15%, 20%, 25%, 30%, 35%, 40%, 45%, 50%, 55%, 60%, 65%, 70%, 75%, or 80%, as compared to a detection solution without COT and quercetin. In some such embodiments, photobleaching or DNA damage is measured by the percent remaining fluorescent intensity after 10 minutes, 20 minutes, or 30 minutes light irradiation, or after 1, 10, 25, 50, 75, 100, 125 or 150 sequencing runs. In some such embodiments, the photobleaching is caused by a blue light having a wavelength between 450 nm to 460 nm. In some such embodiments, the fluorescent intensity is measured in the detection solution as described herein. In other embodiment, the fluorescent intensity is measured on a solid support surface, such as flow cell.

In all embodiments of the methods, the detection step may be carried out whilst the polynucleotide strand into which the labeled nucleotides are incorporated is annealed to a template strand, or after a denaturation step in which the two strands are separated. Further steps, for example chemical or enzymatic reaction steps or purification steps, may be included between the synthetic step and the detection step. In particular, the target strand incorporating the labeled nucleotide(s) may be isolated or purified and then processed further or used in a subsequent analysis. By way of example, target polynucleotides labeled with COT-modified nucleotide(s) as described herein in a synthetic step may be subsequently used as labeled probes or primers. In other embodiments the product of the synthetic step (a) may be subject to further reaction steps and, if desired, the product of these subsequent steps purified or isolated.

Suitable conditions for the synthetic step will be well known to those familiar with standard molecular biology techniques. In one embodiment the synthetic step may be analogous to a standard primer extension reaction using nucleotide precursors, including labeled nucleotides according to the present disclosure, to form an extended target strand complementary to the template strand in the presence of a suitable polymerase enzyme. In other embodiments the synthetic step may itself form part of an amplification reaction producing a labeled double stranded amplification product comprised of annealed complementary strands derived from copying of the target and template polynucleotide strands. Other exemplary "synthetic" steps include nick translation, strand displacement polymerization, random primed DNA labeling etc. The polymerase enzyme used in the synthetic step must be capable of catalyzing the incorporation of labeled nucleotides according to the present disclosure. Otherwise, the precise nature of the polymerase is not particularly limited but may depend upon the conditions of the synthetic reaction. By way of example, if the synthetic reaction is carried out using thermocycling then a thermostable polymerase is required, whereas this may not be essential for standard primer extension reactions. Suitable thermostable polymerases which are capable of incorporating the labeled nucleotides according to the present disclosure include those described in WO 2005/024010 or WO 2006/120433. In synthetic reactions which are carried out at lower temperatures such as 37° C., polymerase enzymes need not necessarily be thermostable polymerases, therefore the choice of polymerase will depend on a number of factors such as reaction temperature, pH, strand-displacing activity and the like.

In specific non-limiting embodiments, the nucleotides or nucleosides labeled with the COT moiety-bonded fluorescent dyes with longer Stokes shift according to the present application may be used in a method of nucleic acid sequencing, re-sequencing, whole genome sequencing, single nucleotide polymorphism scoring, any other application involving the detection of the labeled nucleotide or nucleoside when incorporated into a polynucleotide, or any other application requiring the use of polynucleotides labeled with the nucleotides comprising fluorescent dyes according to the present application.

In a particular embodiment the present application provides use of nucleotides comprising COT modified dye compounds described herein in a polynucleotide "sequencing-by-synthesis" reaction. Sequencing-by-synthesis generally involves sequential addition of one or more nucleotides or oligonucleotides to a growing polynucleotide chain in the 5' to 3' direction using a polymerase or ligase in order to form an extended polynucleotide chain complementary to the template nucleic acid to be sequenced. The identity of the base present in one or more of the added nucleotide(s) is determined in a detection or "imaging" step. The identity of the added base may be determined after each nucleotide incorporation step. The sequence of the template may then be inferred using conventional Watson-Crick base-pairing rules. The use of the nucleotides labeled with dyes according to the present disclosure for determination of the identity of a single base may be useful, for example, in the scoring of single nucleotide polymorphisms, and such single base extension reactions are within the scope of this application.

In an embodiment, the sequence of a template polynucleotide is determined by detecting the incorporation of one or more nucleotides into a nascent strand complementary to the template polynucleotide to be sequenced through the detection of fluorescent label(s) attached to the incorporated nucleotide(s). Sequencing of the template polynucleotide is primed with a suitable primer (or prepared as a hairpin construct which will contain the primer as part of the hairpin), and the nascent chain is extended in a stepwise manner by addition of nucleotides to the 3' end of the primer in a polymerase-catalyzed reaction.

In particular embodiments each of the different nucleotide triphosphates (A, T, G and C) may be labeled with a unique fluorophore and also comprises a blocking group at the 3' position to prevent uncontrolled polymerization. Alternatively, one of the four nucleotides may be unlabeled (dark). The polymerase enzyme incorporates a nucleotide into the nascent chain complementary to the template polynucleotide, and the blocking group prevents further incorporation of nucleotides. Any unincorporated nucleotides are removed and the fluorescent signal from each incorporated nucleotide is "read" optically by suitable means, such as a charge-coupled device using laser excitation and suitable emission filters. The 3'-blocking group and fluorescent dye compounds are then removed (deprotected), particularly by the same chemical or enzymatic method, to expose the nascent chain for further nucleotide incorporation. Typically, the identity of the incorporated nucleotide will be determined after each incorporation step but this is not strictly essential. Similarly, U.S. Pat. No. 5,302,509 discloses a method to sequence polynucleotides immobilized on a solid support. The method relies on the incorporation of fluorescently labeled, 3'-blocked nucleotides A, G, C and T into a growing strand complementary to the immobilized polynucleotide, in the presence of DNA polymerase. The polymerase incorporates a base complementary to the target polynucleotide, but is prevented from further addition by the 3'-blocking group. The label of the incorporated nucleotide can then be determined and the blocking group removed by chemical cleavage to allow further polymerization to occur. The nucleic acid template to be sequenced in a sequencing-by-synthesis reaction may be any polynucleotide that it is desired to sequence. The nucleic acid template for a sequencing reaction will typically comprise a double stranded region having a free 3' hydroxyl group which serves as a primer or initiation point for the addition of further nucleotides in the sequencing reaction. The region of the template to be sequenced will overhang this free 3' hydroxyl group on the complementary strand. The overhanging region of the template to be sequenced may be single stranded but can be double-stranded, provided that a "nick is present" on the strand complementary to the template strand to be sequenced to provide a free 3' OH group for initiation of the sequencing reaction. In such embodiments sequencing may proceed by strand displacement. In certain embodiments a primer bearing the free 3' hydroxyl group may be added as a separate component (e.g. a short oligonucleotide) which hybridizes to a single-stranded region of the template to be sequenced. Alternatively, the primer and the template strand to be sequenced may each form part of a partially self-complementary nucleic acid strand capable of forming an intra-molecular duplex, such as for example a hairpin loop structure. Hairpin polynucleotides and methods by which they may be attached to solid supports are disclosed in PCT Publication Nos. WO 2001/057248 and WO 2005/047301. Nucleotides are added successively to the free 3'-hydroxyl group, resulting in synthesis of a polynucleotide chain in the 5' to 3' direction. The nature of the base which has been added may be determined, particularly but not necessarily after each nucleotide addition, thus providing sequence information for the nucleic acid template. The term "incorporation" of a nucleotide into a nucleic acid strand (or polynucleotide) in this context refers to joining of the nucleotide to the free 3' hydroxyl group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments the nucleic acid template to be sequenced may be attached to a solid support via any suitable linkage method known in the art, for example via covalent attachment. In certain embodiments template polynucleotides may be attached directly to a solid support (e.g. a silica-based support). However, in other embodiments the surface of the solid support may be modified in some way so as to allow either direct covalent attachment of template polynucleotides, or to immobilize the template polynucleotides through a hydrogel or polyelectrolyte multilayer, which may itself be non-covalently attached to the solid support.

Arrays in which polynucleotides have been directly attached to silica-based supports are those for example disclosed in PCT Publication No. WO 2000/006770, wherein polynucleotides are immobilized on a glass support by reaction between a pendant epoxide group on the glass with an internal amino group on the polynucleotide. In addition, PCT Publication No. WO2005/047301 discloses arrays of polynucleotides attached to a solid support, e.g. for use in the preparation of SMAs, by reaction of a sulfur-based nucleophile with the solid support. A still further example of solid-supported template polynucleotides is where the template polynucleotides are attached to hydrogel supported upon silica-based or other solid supports. Silica-based supports are typically used to support hydrogels and hydrogel arrays as described in PCT Publication Nos. WO 00/31148, WO 01/01143, WO02/12566, WO 03/014392, WO 00/53812 and U.S. Pat. No. 6,465,178.

A particular surface to which template polynucleotides may be immobilized is a polyacrylamide hydrogel. Polyacrylamide hydrogels are described in the prior art, some of which is discussed above. Specific hydrogels that may be used in the present application include those described in WO 2005/065814 and U.S. Pub. No. 2014/0079923. In one embodiment, the hydrogel is PAZAM (poly(N-(5-azidoacetamidylpentyl) acrylamide-co-acrylamide)).

DNA template molecules can be attached to beads or microparticles for the purposes of sequencing; for example as described in U.S. Pat. No. 6,172,218. Further examples of the preparation of bead libraries where each bead contains different DNA sequences can be found in Margulies et al., Nature 437, 376-380 (2005); Shendure et al., Science. 309(5741):1728-1732 (2005). Sequencing of arrays of such beads using nucleotides as described is within the scope of the present application.

The template(s) to be sequenced may form part of an "array" on a solid support, in which case the array may take any convenient form. Thus, the method of the present disclosure is applicable to all types of "high density" arrays, including single-molecule arrays, clustered arrays and bead arrays. Nucleotides labeled with dye compounds of the present application may be used for sequencing templates on essentially any type of array formed by immobilization of nucleic acid molecules on a solid support, and more particularly any type of high-density array. However, nucleotides labeled with the COT moiety-bonded fluorescent dyes described herein are particularly advantageous in the context of sequencing of clustered arrays.

In multi-polynucleotide or clustered arrays, distinct regions on the array comprise multiple polynucleotide template molecules. The term "clustered array" refers to an array wherein distinct regions or sites on the array comprise multiple polynucleotide molecules that are not individually resolvable by optical means. Depending on how the array is formed each site on the array may comprise multiple copies of one individual polynucleotide molecule or even multiple copies of a small number of different polynucleotide molecules (e.g. multiple copies of two complementary nucleic acid strands). Multi-polynucleotide or clustered arrays of nucleic acid molecules may be produced using techniques generally known in the art. By way of example, WO 98/44151 and WO 00/18957 both describe methods of amplification of nucleic acids wherein both the template and amplification products remain immobilized on a solid support in order to form arrays comprised of clusters or "colonies" of immobilized nucleic acid molecules. The nucleic acid molecules present on the clustered arrays prepared according to these methods are suitable templates for sequencing using nucleotides labeled with the COT moiety-bonded fluorescent dyes described herein.

The nucleotides labeled with dye compounds of the present application are also useful in sequencing of templates on single molecule arrays. The term "single molecule array" or "SMA" as used herein refers to a population of polynucleotide molecules, distributed (or arrayed) over a solid support, wherein the spacing of any individual polynucleotide from all others of the population is such that it is possible to effect individual resolution of the polynucleotides. The target nucleic acid molecules immobilized onto the surface of the solid support should thus be capable of being resolved by optical means. This means that, within the resolvable area of the particular imaging device used, there must be one or more distinct signals, each representing one polynucleotide.

This may be achieved wherein the spacing between adjacent polynucleotide molecules on the array is at least 100 nm, more particularly at least 250 nm, still more particularly at least 300 nm, even more particularly at least 350 nm. Thus, each molecule is individually resolvable and detectable as a single molecule fluorescent point, and fluorescence from said single molecule fluorescent point also exhibits single step photo-bleaching.

The terms "individually resolved" and "individual resolution" are used herein to specify that, when visualized, it is possible to distinguish one molecule on the array from its neighboring molecules. Separation between individual molecules on the array will be determined, in part, by the particular technique used to resolve the individual molecules. The general features of single molecule arrays will be understood by reference to PCT Publication Nos. WO 2000/006770 and WO 2001/057248. Although one application of the labeled nucleotides of the present disclosure is in sequencing-by-synthesis reactions, the utility of such labeled nucleotides is not limited to such methods. In fact, the nucleotides may be used advantageously in any sequencing methodology which requires detection of fluorescent labels attached to nucleotides incorporated into a polynucleotide.

In particular, the labeled nucleotides of the present disclosure may be used in automated fluorescent sequencing protocols, particularly fluorescent dye-terminator cycle sequencing based on the chain termination sequencing method of Sanger and co-workers. Such methods generally use enzymes and cycle sequencing to incorporate fluorescently labeled dideoxynucleotides in a primer extension sequencing reaction. So called Sanger sequencing methods, and related protocols (Sanger-type), rely upon randomized chain termination with labeled dideoxynucleotides.

Thus, the present disclosure also encompasses labeled nucleotides which are dideoxynucleotides lacking hydroxyl groups at both of the 3' and 2' positions, such modified dideoxynucleotides being suitable for use in Sanger type sequencing methods and the like.

EXAMPLES

Additional embodiments are disclosed in further detail in the following examples, which are not in any way intended to limit the scope of the claims.

Example 1

In this example, the photobleaching rates of four labeled fully functionalized nucleotides (ffC-sPA-Dye 1, ffA-Dye 2, ffA-Dye 3 and ffA-Dye 4) were tested in a detection solution containing 10 mM cyclooctatetraene and 0.25 mM quercetin ("COT mix") in addition to a control detection solution against a control detection solution containing just a universal scanning mix ("USM"). After 30 minutes of blue LED light irradiation, the percentage remained fluorescent intensity was measured for each of the labeled nucleotides and the results are shown in FIG. 1. The results indicate that for each of labeled nucleotides, the photobleaching rate of the dye was significantly reduced in the COT mix.

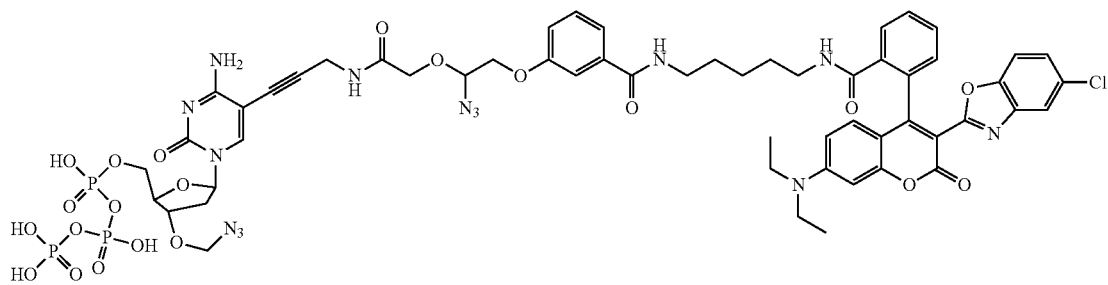

ffC-sPA-Dye 1

-continued
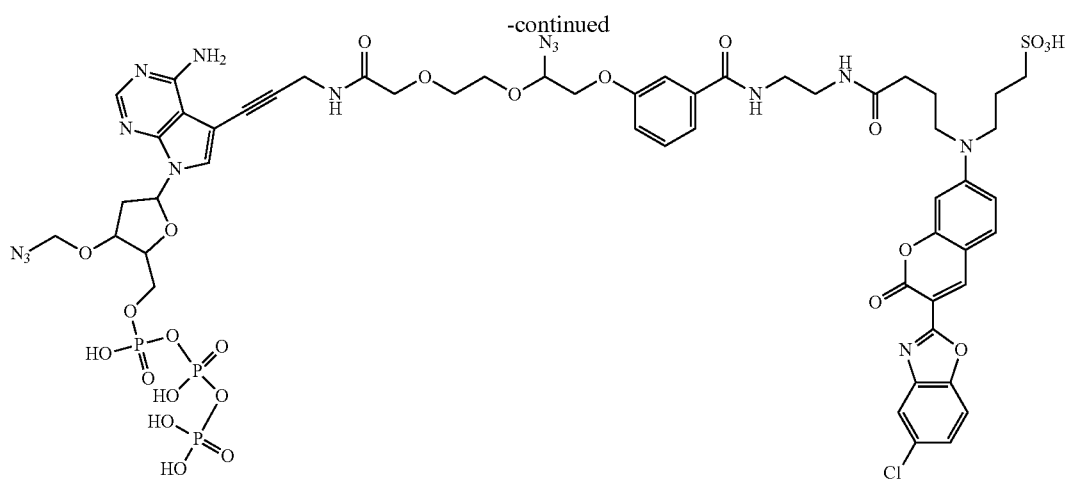
ffA-Dye 2
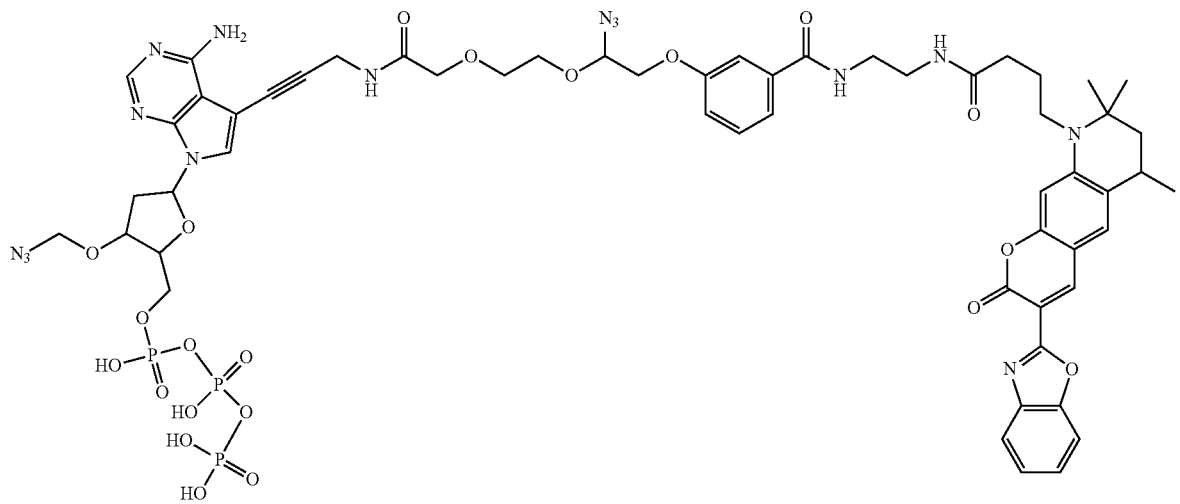
ffA-Dye 3
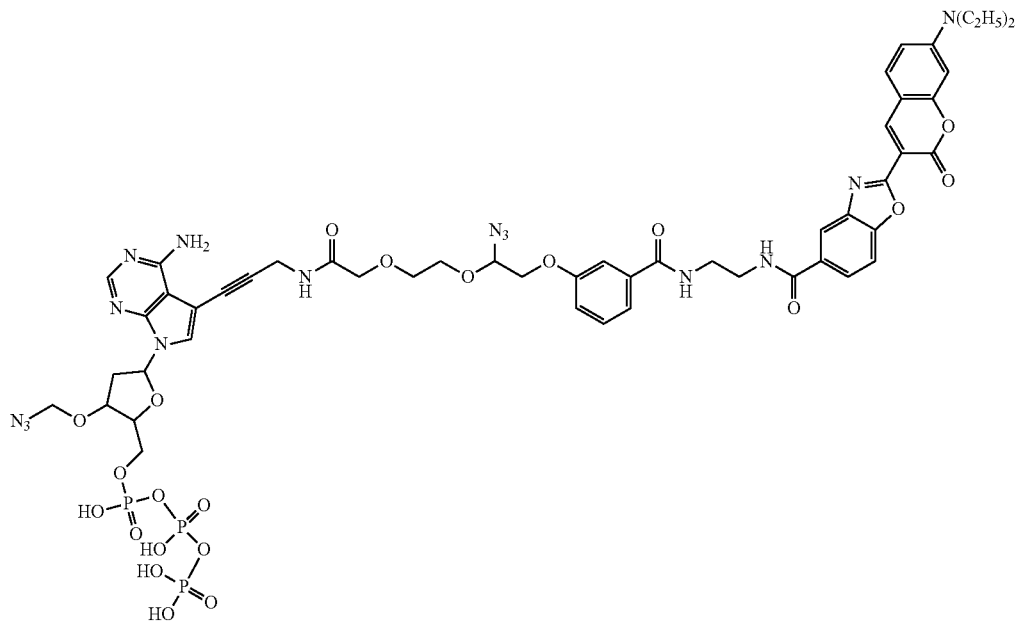
ffA-Dye 4

Figure 2:
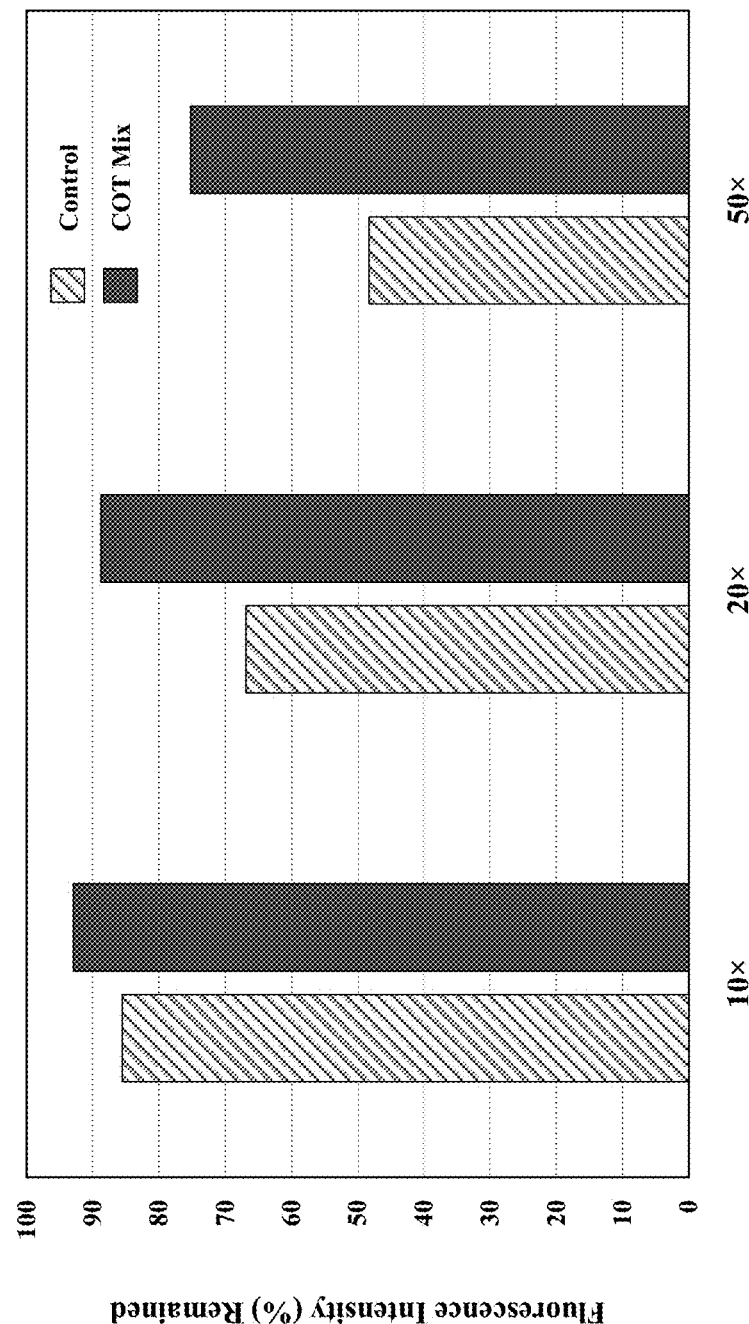
FIG. 2 illustrates the photobleaching rate of a fluorescent dye after incorporated into the cluster on the flow cell surface when a standard detection solution and a solution containing cyclooctatetraene and quercetin are used respectively.

In a separate experiment, the photobleaching rate of ffA labeled with Dye 4 was measured after the labeled nucleotide was incorporated into the cluster on the surface of a flowcell. FIG. 2 illustrates the percentage remained fluorescent intensity measured after 10 times, 20 times, and 50 times of irradiation when a standard detection solution (control) and the COT mix were used respectively. The results indicated the addition of cyclooctatetraene and quercetin into the control detection solution had a positive impact on the reduction rate of dye bleaching.

Figure 3A:
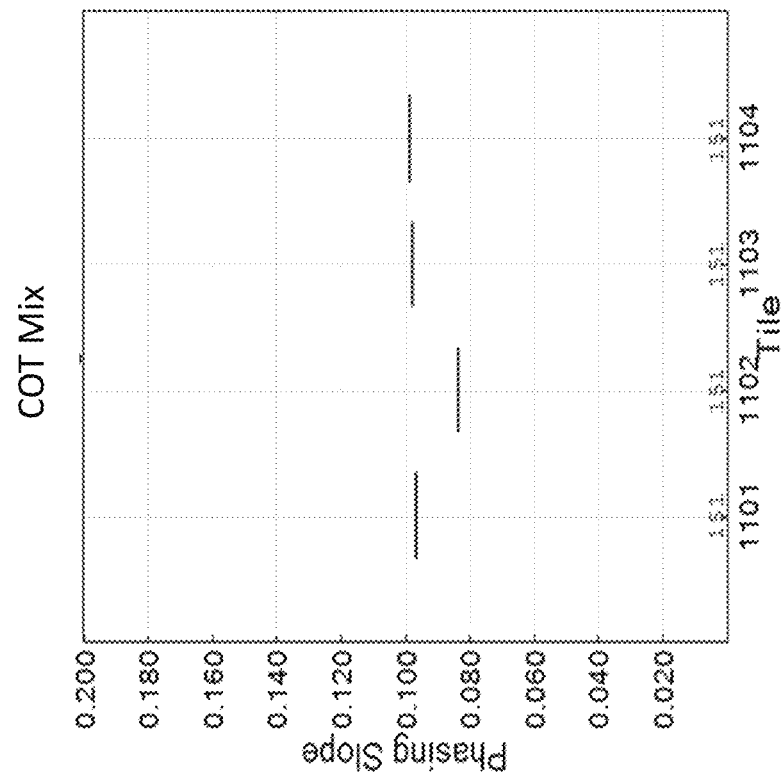
FIG. 3A illustrates the phasing values of DNA cluster during sequencing with increased light exposure when a standard detection solution is used during the scan step of the sequencing.
Figure 3B:
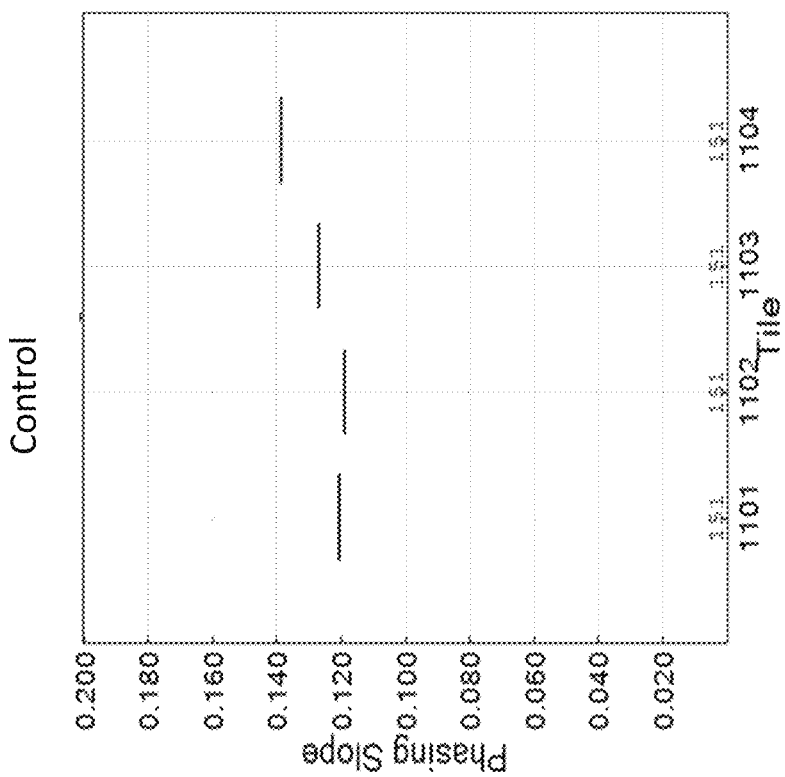
FIG. 3B illustrates the phasing values of DNA cluster during sequencing with increased light exposure when a solution containing cyclooctatetraene and quercetin is used during the scan step of the sequencing.

Further experiments on Illumina sequencing platform MiSeq® using light irradiation on the DNA clusters also indicated that the addition of COT and quercetin could prevent DNA damage caused by light exposure during the detection step of the sequencing run. The sequencing matrix showed the phasing value increased with light exposure when using the standard scan mix (USM) (FIG. 3A), while there was no increasing in phasing value when the "COT mix" was used (FIG. 3B).

Example 2

In this example, various new amino-functionalized N-substituted amides of 1,3,5,7-cyclooktotetraenyl carboxylic acid were prepared from COT-COOH via carboxyl group activation. The exemplary compounds are shown below:

Synthesis of COT Compounds

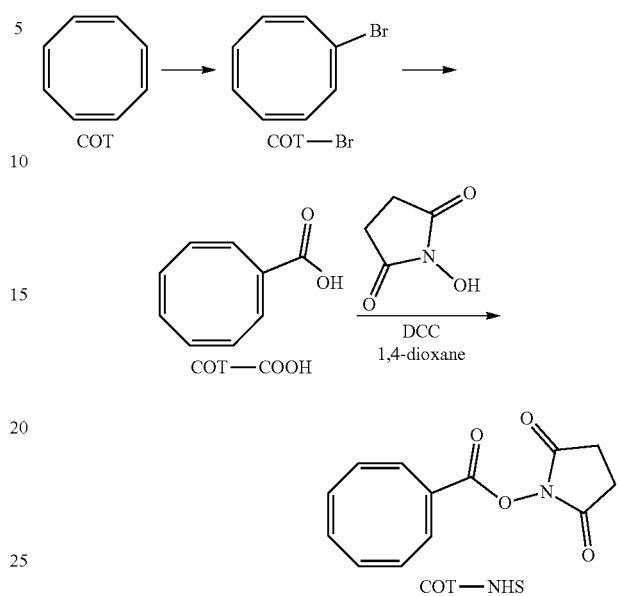

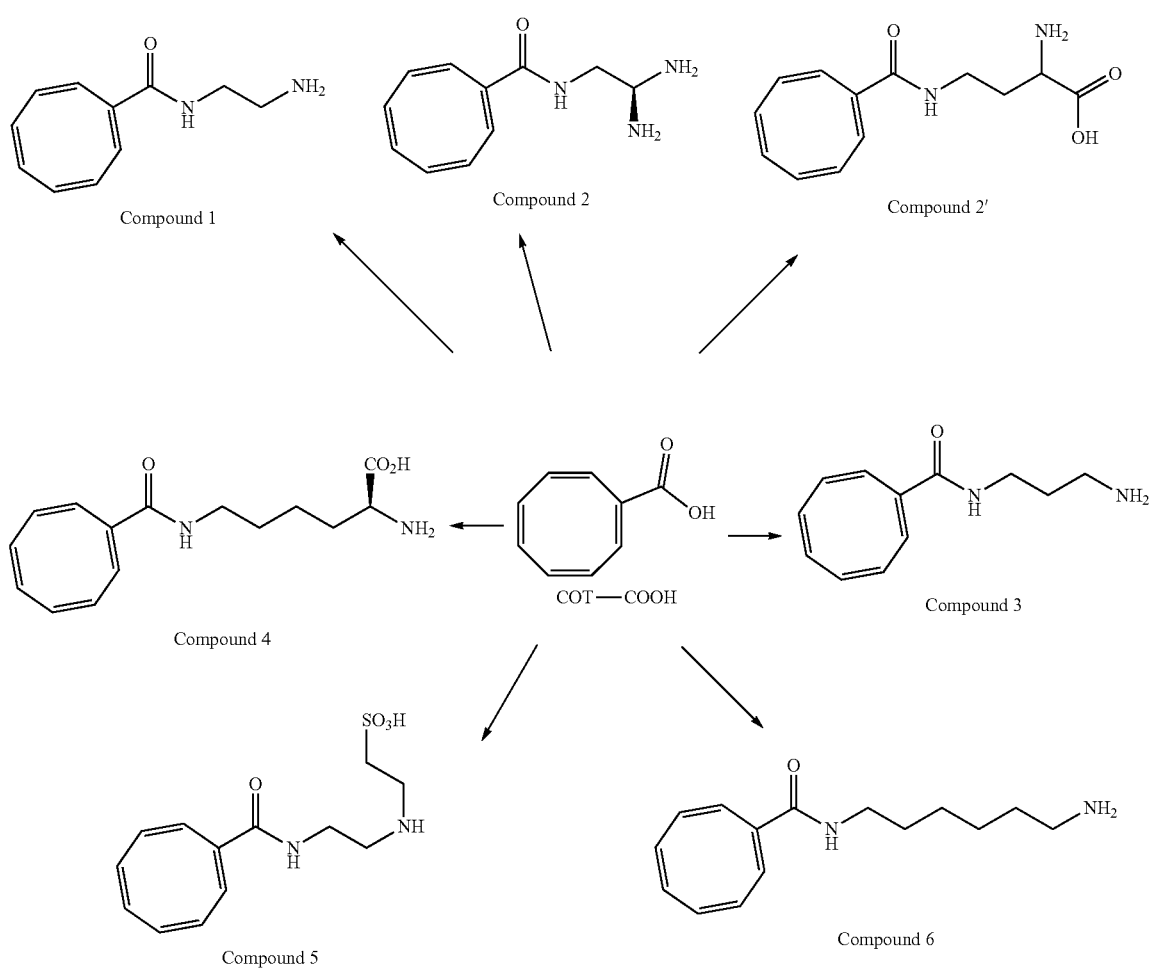

Carboxycycloocta-1,3,5,7-tetraen (COT-COOH) was prepared from COT in two steps following the general procedure described in J. Am. Chem. Soc. 1952, 74, pp 168-172 and pp 173-175. COT-COOH (10 mmol, 1.48 g) and N-hydroxy-succinimide (NHS, 10 mmol, 1.15 g) were dissolved in dioxane. Yellow-colored solution was cooled to 0° C. using ice bath before N,N'-dicyclohexylcarbodiimide (DCC, 10 mmol, 2.06 g) was added as a solid. The reaction mixture was stirred at 0° C. for 15 mins. Then the ice bath was removed and the reaction mixture was allowed to warm to room temperature (RT) while stirring. The reaction was completed after 1 hour as indicated by TLC. COT-NHS ester was confirmed by LC-MS and was used for the synthesis of COT compounds 1 through 6 without further purification.

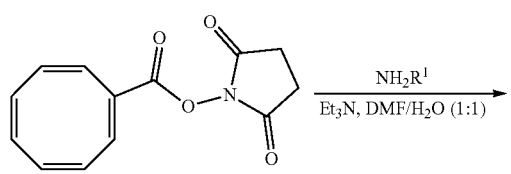

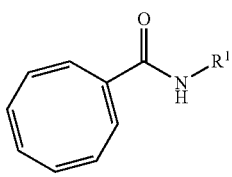

General Procedure: COT-NHS ester (245 mg, 1.0 mmol) was dissolved in DMF (6 mL) and added to a flask containing appropriate amine (1.25 mmol), water (6 mL) and triethylamine (0.41 mL, 3 mmol) at 0° C. The reaction mixture was allowed to warm to RT and stirred for 4 h. Saturated aqueous $NH_4C_1$ solution was added and the product was extracted from the reaction mixture with $CH_2Cl_2$ (DCM) (2×10 mL). The aqueous phase was acidified further with 1M aqueous HCl and extracted again with additional 2×10 mL of DCM. The combined organic phases were washed with brine, dried with $Na_2SO_4$. Solution was filtered and concentrated in vacuo. The crude residue was purified by column chromatography.

Compound 1: N-(2-Aminoethyl)cycloocta-1,3,5,7-tetraene-1-carboxamide

A solution of 1,2-ethylenediamine (10 Eq) in DCM was cooled to 0° C. in a round-bottomed flask fitted with stirring bar, nitrogen gas line and dropping funnel. Solution of COT-NHS prepared as described above was transferred into the dropping funnel and added to the ethylenediamine solution over 10 mins. The dropping funnel was rinsed with more DCM and solution was added into the flask. The reaction mixture was allowed to warm to RT and stirred at RT for three hours. Reaction confirmed as completed by TLC and LCMS. Most of the solvents were distilled off and residue purified by flash chromatography. Yield: 76%. Purity, structure and composition were confirmed by LCMS and NMR.

Compound 2 (BOC protected): 2-[(tert-Butoxycarbonyl)amino]-3-(cycloocta-1,3,5,7-tetraene-1-yl-carboxamido)propanoic acid

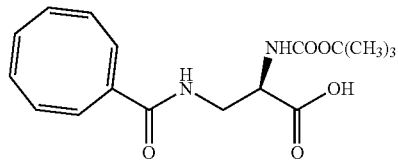

Boc-L-2,3-diaminopropionic acid (12.5 mmol, 2.55 g) was dissolved in deionized water (35 mL) treated with $Et_3N$ (30 mmol, 4.2 mL). Solution was cooled to 0° C. COT-NHS (10 mmol) was added as a solution in DMF (35 ml) dropwise, keeping temperature at 0° C. Warmed to RT and stirred for 90 mins. LCMS confirmed conversion to desired product, with all starting material consumed. Worked up reaction by diluting with aqueous ammonium chloride and extracting with DCM. Aqueous layer was acidified with 1M HCl and extracted again with further amount of DCM. Combined DCM fractions was dried by anhydrous magnesium sulphate, solvents evaporated and the residue was purified by flash chromatography. Yield 64%.

Compound 2: 2-Amino-3-(cycloocta-1,3,5,7-tetraene-1-yl-carboxamido)propanoic acid Compound 2 (BOC protected) (250 mg, 0.75 mmol) in DCM (5 mL) was treated with TFA (1 mL) and the mixture stirred at RT for 17 h. The solution was then concentrated in vacuo and $Et_2O$ added, forming a white precipitate. The solvent was decanted, and the precipitate washed with further $Et_2O$. The resulting precipitate was dried under vacuum to afford trifluoroacetate salt (TFA salt) of Compound 2 as an off-white solid (257 mg, Yield 98%). $^1H$ NMR (400 MHz, $D_2O$) δ 6.82 (s, 1H), 6.14 (dd, J=11.4, 3.1 Hz, 1H), 6.03-5.86 (m, 5H), 4.17-4.08 (m, 1H), 3.89-3.66 (m, 2H). $^{13}C$ NMR (101 MHz, D20) δ 170.50, 169.93, 139.68, 136.24, 135.22, 133.79, 132.13, 131.66, 130.16, 127.82, 53.83, 39.57. $^{19}F$ NMR (376 MHz, Deuterium Oxide) δ −75.64.

Compound 2' (BOC protected): 2-[(tert-Butoxycarbonyl)amino]-4-(cycloocta-1,3,5,7-tetraene-1-yl-carboxamido)butanoic acid

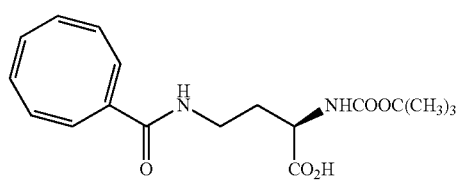

This intermediate was prepared following the procedure described in the synthesis of Compound 2 (BOC protected) starting from Boc-L-2,4-diaminobutanoic acid.

Compound 2': 2-Amino-4-(cycloocta-1,3,5,7-tetraene-1-yl-carboxamido)butanoic acid Compound 2' was prepared following the procedure described in the synthesis of Compound 2 starting from Compound 2' (BOC protected). It was purified by HPLC. Purity, structure and composition were confirmed by LCMS and NMR.

Compound 3: N-(3-Aminopropyl)cycloocta-1,3,5,7-tetraene-1-yl-carboxamide

COT-NHS ester (1.0 mmol) and 1,3-diaminopropane (0.84 mL, 10 mmol) were stirred for 4 h at RT. The crude residue was purified by column chromatography to give Compound 3 as an orange oil (197 mg, 97%). $^1$H NMR (400 MHz, Chloroform-d) δ 6.89-6.79 (m, 1H), 6.53 (s, 1H), 6.07-5.63 (m, 6H), 3.41-3.26 (m, 2H), 2.74 (t, J=6.3 Hz, 2H), 1.68-1.48 (m, 2H). $^{13}$C NMR (101 MHz, CDCl$_3$) δ 165.86, 137.99, 136.41, 135.30, 132.66, 132.37, 131.40, 130.87, 128.80, 40.22, 38.48, 32.00.

Compound 4 (BOC protected): N$^2$-(tert-butoxycarbonyl)-N$^6$-(cycloocta-1,3,5,7-tetraene-1-yl-carbonyl)-L-lysine

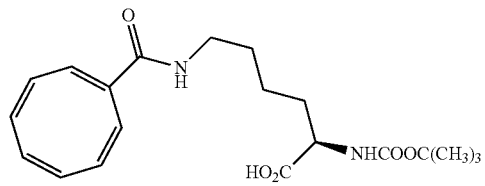

COT-NHS ester (2.57 mmol) and L-BOC-Lysine (3.21 mmol) were stirred for 2 h at RT. Reaction mixture was work-up as described above and the crude residue was purified by column chromatography to give Compound 4 (BOC protected) as pale yellow solid (yield=561 mg, 58%).

Compound 4: N$^6$-(Cycloocta-1,3,5,7-tetraene-1-yl-carbonyl)-L-lysine

Compound 4 (BOC-protected) from the previous step was treated with TFA in DCM following the procedure as described in the synthesis of Compound 2 to afford Compound 4 as an off-white solid (109 mg, 66%). $^1$H NMR (400 MHz, D2O) δ 6.63 (s, 1H), 6.11-5.70 (m, 6H), 3.91 (t, J=6.2 Hz, 1H), 3.14 (t, J=6.9 Hz, 2H), 1.99-1.68 (m, 2H), 1.53-1.21 (m, 4H). $^{13}$C NMR (101 MHz, D2O) δ 172.34, 168.63, 138.43, 136.00 (2C), 133.56, 132.12, 131.67, 130.31, 128.07, 52.93, 39.15, 29.45, 27.98, 21.63. $^{19}$F NMR (376 MHz, D2Oj) δ −75.64.

Compound 5: 2-(2-Cycloocta-1,3,5,7-tetraene-1-yl-carboxamido)ethyl)amino)ethane-1-sulfonic acid Compound 5 was prepared following the procedure described in the synthesis of Compound 1 from COT-NHS ester (1 mmol), sodium 2-[(2-aminoethyl)amino]ethanesulphonate (238 mg, 1.25 mmol), Et$_3$N (0.07 mL, 0.5 mmol) in DMF 7 mL. The reaction mixture was stirred at RT for 4 h and the crude residue purified by column chromatography. Compound 5 was obtained as a reddish gum (169 mg). Yield 57%. $^1$H NMR (400 MHz, Deuterium Oxide) δ 6.75 (s, 1H), 6.05 (s, 1H), 5.95-5.74 (m, 5H), 3.51 (t, J=5.4 Hz, 2H), 3.39 (t, J=6.8 Hz, 2H), 3.24-3.15 (m, 4H). $^{13}$C NMR (101 MHz, CDCl$_3$) δ 176.76, 167.38, 138.95, 135.89, 135.30, 133.27, 131.94, 130.50, 128.65, 47.75, 46.65, 44.13, 36.60.

Compound 6: N-(6-Aminohexyl)cycloocta-1,3,5,7-tetraene-1-yl-carboxamide

Compound 6 was prepared following the procedure described in the synthesis of Compound 1. COT-NHS ester (1 mmol) and hexamethylenediamine (1.46 g, 12.5 mmol) were stirred for 4 h at RT in DMF (7 mL). Solvent was distilled off and the crude residue was purified by column chromatography to afford Compound 6 as an orange oil (195 mg). Yield 79%. $^1$H NMR (400 MHz, Chloroform-d) δ 6.97-6.89 (s, 1H), 6.19-5.67 (m, 6H), 3.31 (br s, 1H), 2.79 (t, J=7.0 Hz, 2H), 1.63-1.47 (m, 4H), 1.46-1.30 (m, 4H). $^{13}$C NMR (101 MHz, CDCl$_3$) δ 165.73, 138.11, 136.34, 135.66, 132.69, 132.47, 131.30, 130.81, 128.60, 41.94, 39.80, 33.21, 29.50, 26.72, 26.46.

Compound 7: 2-amino-3-[3-(cycloocta-1,3,5,7-tetraen-1-yl)acrylamido]propanoic acid

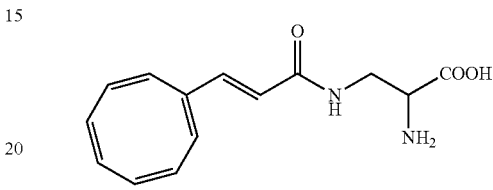

Solution of formyl cyclooctatetraene (212 mg, 1.60 mmol) in THF (15 mL) was cooled to 0° C. and treated with sodium hydride (96 mg, 2.41 mmol). The mixture was stirred for 45 min at 0° C. and ethyl 2-(diethoxyphosphoryl)acetate (0.57 mL, 2.89 mmol) in THF (5 mL) added. The reaction mixture was stirred at room temperature for 2 h, and then quenched with excess of saturated aqueous ammonium chloride. The product was extracted with ethyl acetate the combined organics extracts were washed with brine, dried over anhydrous sodium sulfate and concentrated in vacuo. The crude residue was purified by column to afford ethyl 3-(cycloocta-1,3,5,7-tetraen-1-yl)acrylate as an orange oil. Yield: 374 mg (95%).

Solution of ethyl 3-cycloocta-1,3,5,7-tetraen-1-yl)acrylate (383 mg, 16 mmol) in ethanol (8 mL) was treated with 2M LiOH (aq) (8 mL, 1.6 mmol) and stirred at room temperature for 18 h. The mixture was acidified with 2 M HCl (aq) and the product was extracted with ethyl acetate. The combined organics were dried over anhydrous sodium sulfate and concentrated in vacuo, affording 3-cycloocta-1,3,5,7-tetraen-1-yl)acrylic acid as a brown solid. Yield: 234 mg (72%). LC-MS (−): 173 (M-1).

3-(Cycloocta-1,3,5,7-tetraen-1-yl)acrylic acid (100 mg, 0.49 mmol) in DMF (4 mL) was treated with PyBOP (283 mg, 0.54 mmol) and DIPEA (1 mL) and stirred at room temperature for 10 min. L 3-amino-2-[(tert-butoxycarbonyl)amino]propanoic acid (120 mg, 0.59 mmol) was then added and the mixture stirred at room temperature for 18 h. The reaction mixture was then acidified with 1M hydrochloric acid and diluted with further water. The product was extracted with ethyl acetate, and the combined organics washed with brine, dried over anhydrous sodium sulfate and concentrated in vacuo. The crude residue was purified by column chromatography. After concentrating in vacuo, the residue was redissolved in DCM and treated with TFA (1 mL). The reaction mixture was stirred at room temperature for 5 h and then concentrated in vacuo. The residue was triturated with diethyl ether and resulting solid was dried under vacuum to afford the trifluoroacetate salt of Compound 7 as a brown solid. Yield 132 mg (72%). $^1$H NMR (400 MHz, D2O): δ 7.14 (d, J=15.6 Hz, 1H), 6.18 (d, J=3.9 Hz, 1H), 6.06-5.73 (m, 7H), 4.12 (dd, J=6.0, 4.1 Hz, 1H), 3.83 (dd, J=15.0, 4.1 Hz, 1H), 3.68 (dd, J=15.0, 6.0 Hz, 1H). $^{13}$C NMR (101 MHz, CDCl$_3$): δ 170.34, 169.92, 143.61, 140.09, 139.22, 134.02, 133.05, 131.89, 131.69, 131.22, 129.19, 118.93, 53.69, 39.24. LC-MS (−): 261 (M-1).

Compound 8: 4-[N-(2-aminoethyl)cycloocta-1,3,5,7-tetraene-1-carboxamido]butanoic acid

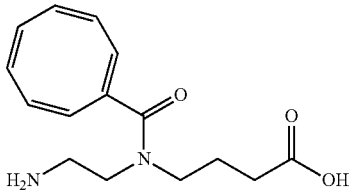 [SMILES: NCCN(CCCC(=O)O)C(=O)C1=C/C=C\C=C/C=C\1]

Carboxycycloocta-1,3,5,7-tetraene (COT-CO₂H, 674 mg, 4.56 mmol) in DMF (10 mL) treated with PyBOP (2.6 g, 5.0 mmol) and DIPEA (2 mL). The mixture was stirred at room temperature for 10 min and then 4-methoxybenzyl 4-((2-((tert-butoxycarbonyl)amino)ethyl)amino)butanoate (2.17 g, 5.92 mmol) was added. The reaction mixture was stirred at room temperature for 18 h and then concentrated in vacuo. The residue was diluted with ethyl acetate and washed with water and brine. The organics were dried over anhydrous sodium sulfate and then concentrated in vacuo. The crude residue was purified by column chromatography to give 4-methoxybenzyl 4-{N-[2-[(tert-butoxycarbonyl)amino]ethyl]cycloocta-1,3,5,7-tetraene-1-carboxamido)-butanoate as an orange oil.

Yield: 1.58 g (70%). LC-MS (−): 495 (M-1).

4-Methoxybenzyl 4-{N-[2-[(tert-butoxycarbonyl)amino]ethyl]cycloocta-1,3,5,7-tetraene-1-carboxamido)-butanoate (1.58 g, 3.18 mmol) in DCM (20 mL) was treated with TFA (3 mL) and stirred at room temperature for 16 h. The reaction mixture was concentrated in vacuo and the residue was triturated with diethyl ether. Solvent was decanted and the residue washed with diethyl ether then dried under vacuum to afford the trifluoroacetate salt of Compound 8 as a brown gum. ¹H NMR (400 MHz, D20) δ 6.13-5.77 (m, 7fH), 3.62 (t, J=6.4 Hz, 4H), 3.16 (d, J=6.3 Hz, 2H), 2.36 (t, J=7.2 Hz, 2H), 1.95-1.83 (m, 2H). LC-MS (+): 277 (M+1).

Synthesis of Dye-COT Compounds

In addition, the COT compounds described herein were covalently attached to fluorescent compounds, for example, those with emission wavelength in the blue light region ("blue dyes"), for example, by reacting an activated carboxyl group of the fluorescent compound with an amino group of the COT compound.

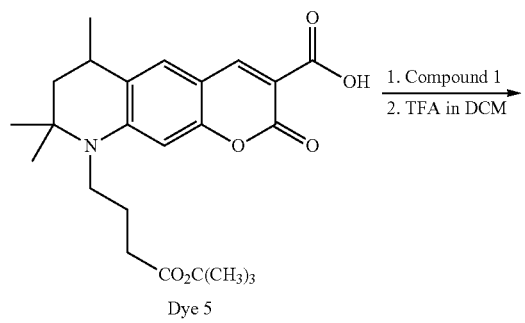

Dye 5

Dye 5 (75 μmol) was dried by co-evaporating with DMF (3×3 mL) and then dried over-night under high vacuum. A stirring bar and PyBOP (75 μmol) were placed in the flask with dried Dye 5. Under nitrogen was added DMF (1.5 mL), then DIPEA (30 ul) for activation reaction. The reaction progress was checked by HPLC and TLC after 15 mins of stirring. When activation of carboxyl-substituted Dye 5 was completed, Compound 1 was added as a solution in DMF (100 mg/ml, 60 μmol) and the reaction mixture was stirred at RT for four hours. TLC and HPLC were used to check the completion of the reaction then solvents were distilled in vacuum. The residue was dissolved in DCM (10 ml) and cooled to 0° C. under nitrogen gas. Trifluoroacetic acid (4 mL) was added, then the ice bath was removed the reaction mixture was stirred while warming to RT. Reaction complete after about 4 hours according to TLC. TFA and solvent were removed in vacuo. 50% TEAB (0.5M)/MeCN (20 mL) were added and filtered before injecting on to prep HPLC for purification (Axia column, 24-44% MeCN). Yield: 25%. Absorption (409 nm) and fluorescence (464 nm) maxima were measured in 1:1 mixture H₂O-MeCN (containing 1% triethylamine).

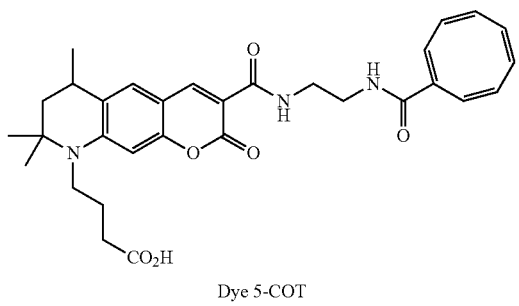

Dye 5-COT

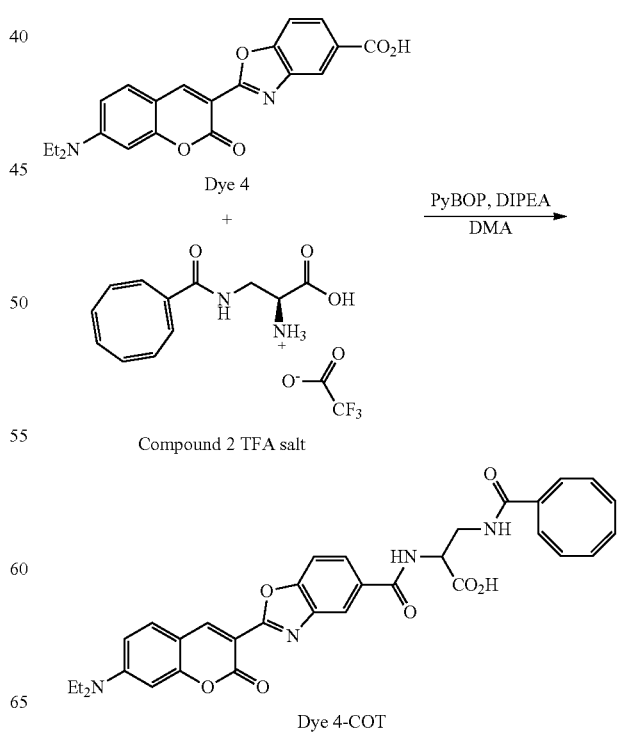

Following the similar procedure described in the synthesis of Dye 5-COT, Dye 4 (15 mg, 40 μmol) in DMA (0.8 mL) was treated with PyBOP (23 mg, 44 μmol) and DIPEA (0.2 mL), followed by Compound 2 (48 mol). The reaction mixture purified by preparative HPLC (40-70%; MeCN: 0.1 M TEAB) to afford Dye 4-COT. Yield: 61%. Absorption spectra (maximum 446 nm) was measured in ethanol.

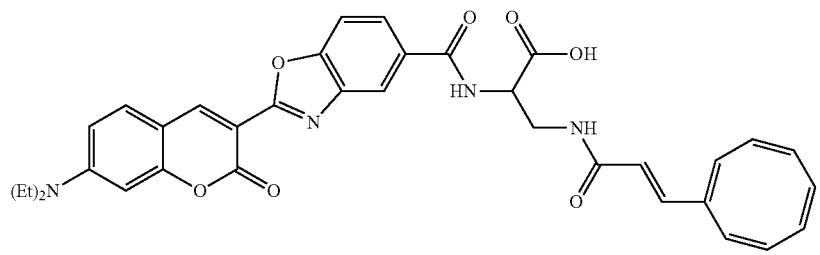

Dye 4-COT-A 2-(7-(Diethylamino)-2-oxo-2H-chromen-3-yl)benzoxazole-5-carboxylic acid (Dye 4, 11 mg, 30 μmol) in anhydrous dimethylacetamide (DMA, 0.8 mL) was treated with PyBOP (17 mg, 33 mol) and DIPEA (0.2 mL). The reaction mixture was stirred at room temperature for 10 min, and then 2-amino-3-[3-(cycloocta-1,3,5,7-tetraen-1-yl)acrylamido] propanoic acid (Compound 7, 15 mg, 36 μmol) was added. The mixture was stirred at room temperature for a further 18 h and then quenched with 0.1 M TEAB. The residue was purified by reverse phase prep HPLC to afford Dye 4-COT-A. Yield: 32%. LC-MS (−): 619 (M-1).

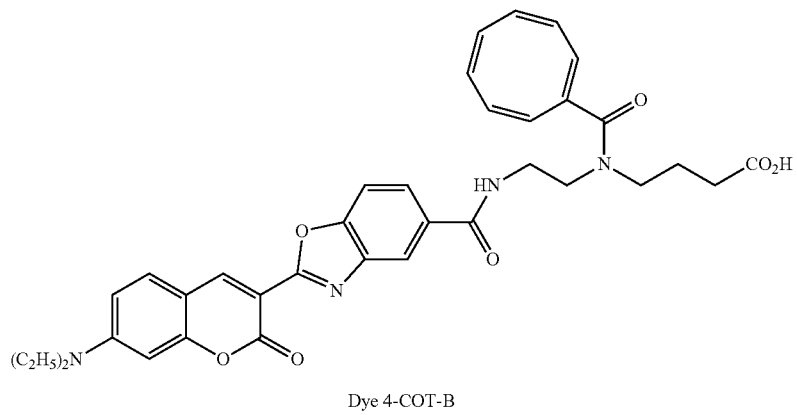

Dye 4-COT-B 2-(7-(Diethylamino)-2-oxo-2H-chromen-3-yl)benzoxazole-5-carboxylic acid (Dye 4, 7.6 mg, 20 μmol) in DMF (2 mL) was treated with TNTU (11 mg, 30 μmol) and DIPEA (35 μL, 200 mol). The mixture was stirred at room temperature for 30 min and then 4-[N-(2-aminoethyl)cycloocta-1,3,5,7-tetraene-1-carboxamido]butanoic acid trifluoroacetate (Compound 8, 24 μmol) in DMF was added. The reaction mixture was stirred at room temperature for 18 h and then quenched with 0.1 M TEAB (aq). The residue was purified by prep HPLC to afford Dye 4-COT-B. Yield: 64%. LC-MS (−): 637 (M-1).

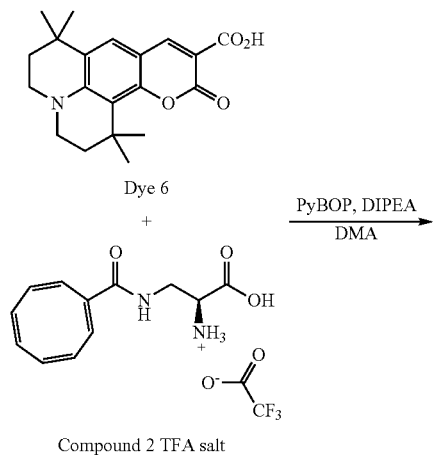

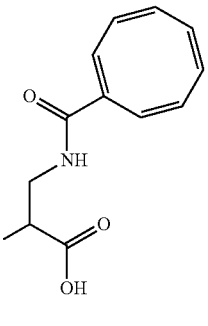

Dye 6-COT

Dye 6 (8.5 mg, 25 μmol) in DMF (0.4 mL) was treated with PyBOP (14 mg, 28 μmol) and DIPEA (0.2 mL) for carboxyl group activation as described above then followed by Compound 2 (10.4 mg, 30 μmol) and reaction mixture was stirred at RT for 18 h. Crude residue was purified by reverse phase preparative HPLC (40-60% MeCN/0.1M TEAB) to afford Dye 6 COT. Yield: 65%. Absorption spectra (maximum 448 nm) was measured in water.

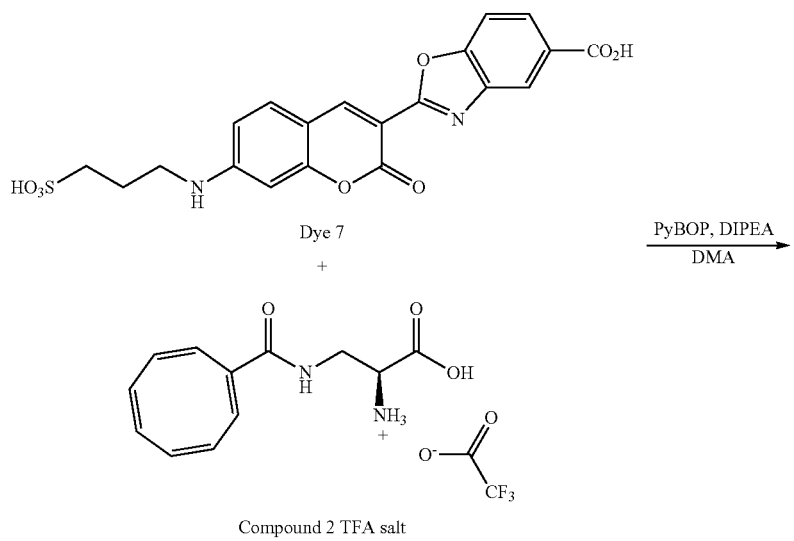

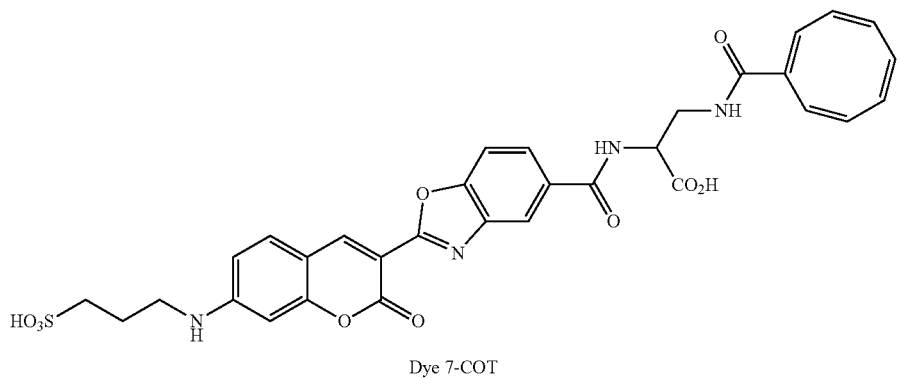

Dye 7-COT

Dye 7 (20 μmol) in DMA (0.4 mL) was treated with PyBOP (11.5 mg, 22 μmol) and DIPEA (0.1 mL), followed by Compound 2 (24 μmol) and the reaction mixture was stirred at RT for 18 h. Crude residue was purified by reverse phase Prep HPLC (20-40% MeCN/0.1M TEAB) to afford Dye 7 COT. Yield: 57%. Absorption spectra (maximum 437 nm) was measured in water.

Synthesis of PI-Dye-COT compounds

Finally, fully functionalized nucleotides (ffNs) were labeled with the COT-containing dyes described herein. The synthetic scheme and procedures are described below.

General procedure: a Dye-COT compound (1.0 eq) was dissolved in DIPEA-DMF (1:2) mixture and then an activation agent, for example PyBOP (1.1 eq), was added and the reaction mixture was stirred at RT for 10 min. ffN-Linker (1.2 eq) was added and reaction mixture was left stirred at RT for 18 h. This reaction mixture was quenched with 0.1M TEAB solution and the product was isolated and purified by reverse phase preparative HPLC.

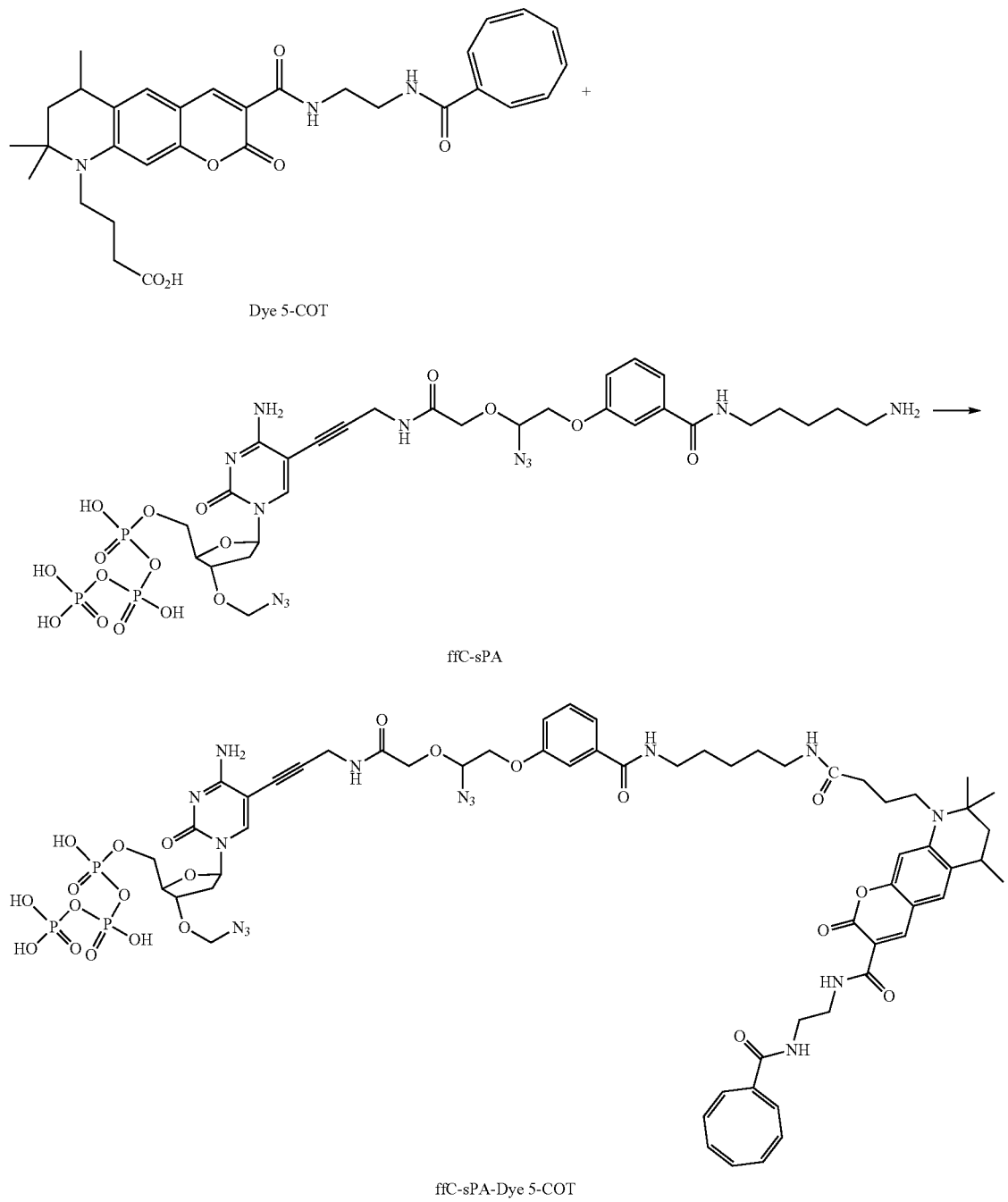

Dye 5-COT was dried by co-evaporating with DMF three times. Dried Dye 5-COT (10 µmol) was dissolved in DMA (0.5 mL). O-(N-Succinimidoyl)-1,1,3,3-tetramethyluronium tetrafluoroborate (TSTU, 15 µmol) and N,N-diisopropylethylamine (DIPEA, 30 µmol) were added. The reaction mixture was stirred at RT under nitrogen for 15 mins. Activation reaction progress was checked by HPLC and TLC.

Triphosphate-deoxyC-sPA (dCTP-sPA) (12 µmol, 20 mM solution in $H_2O$) was dried in vacuo before redissolving in $H_2O$ (0.1 ml). The activated Dye 5-COT was transferred to the flask containing dCTP-sPA. Reaction progress was monitored by HPLC and TLC. Upon completion of reaction, 0.1M TEAB (~2 mL) was added to the reaction flask. The crude reaction mixture was purified using a Sephadex column. Fractions were combined and dried in vacuo and further purified by prep-HPLC. All relevant fractions were combined and dried in vacuo, redissolved in 10 mM TRIS pH 8 buffer to make a 0.1 mM solution of ffC-sPA-Dye 5-COT. Checked purity by analytical HPLC and mass confirmed by LCMS. Yield 48%. Absorption (maximum 443 nm) and fluorescence spectra (maximum 484 nm) were measured in universal scanning mix (USM).

Following the similar procedure described above, Dye 4-COT (24 µmol) in DMA (1 mL) was treated with TSTU (7.8 mg, 26 µmol) and DIPEA (36 µL, 200 mol), followed by dCTP-sPA (20 µmol) in 0.1 M TEAB (100 µL), and $Et_3N$ (10 µL) and stirred at RT for 8 h. The crude residue was purified using reverse phase prep HPLC (YMC column, 10 mL/min, 38-58% MeCN/0.1M TEAB) to afford ffC-sPA-Dye 4-COT. Yield: 57%. Absorption (maximum 460 nm) and fluorescence spectra (maximum 505 nm) were measured in USM.

ffC-sPA-Dye 4-COT-A and ffA-sPA-Dye 4-COT-B were also prepared following similar procedure described herein. ffC-sPA-Dye 4-COT-A: absorption maximum 455 nm (in USM); fluorescence maximum 503 nm (in USM, excitation 450 nm). ffA-sPA-Dye 4-COT-B: absorption maximum 455 nm (in USM); fluorescence maximum 502 nm (in USM, excitation 450 nm).

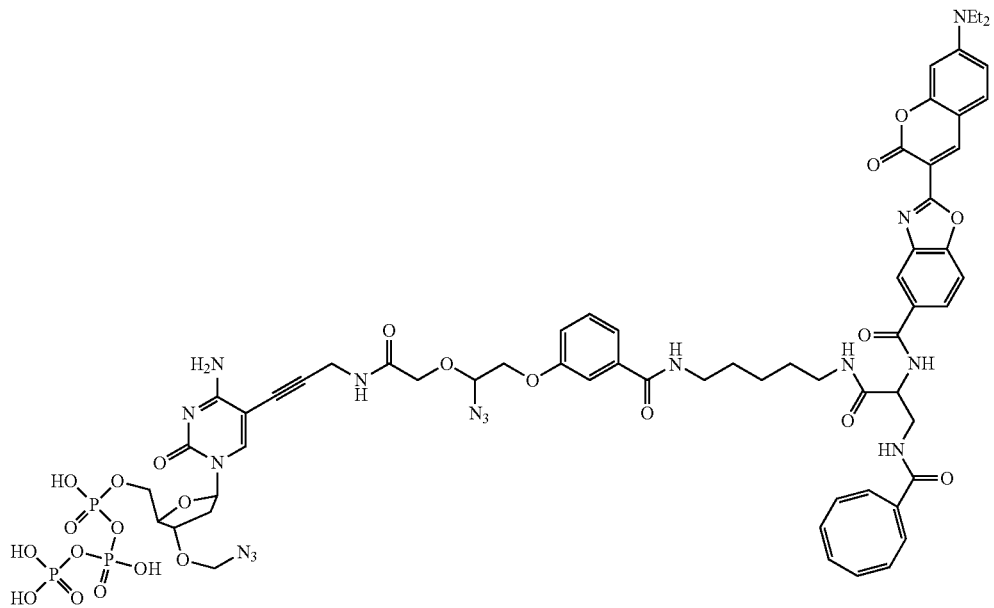

ffC-sPA-Dye 4-COT

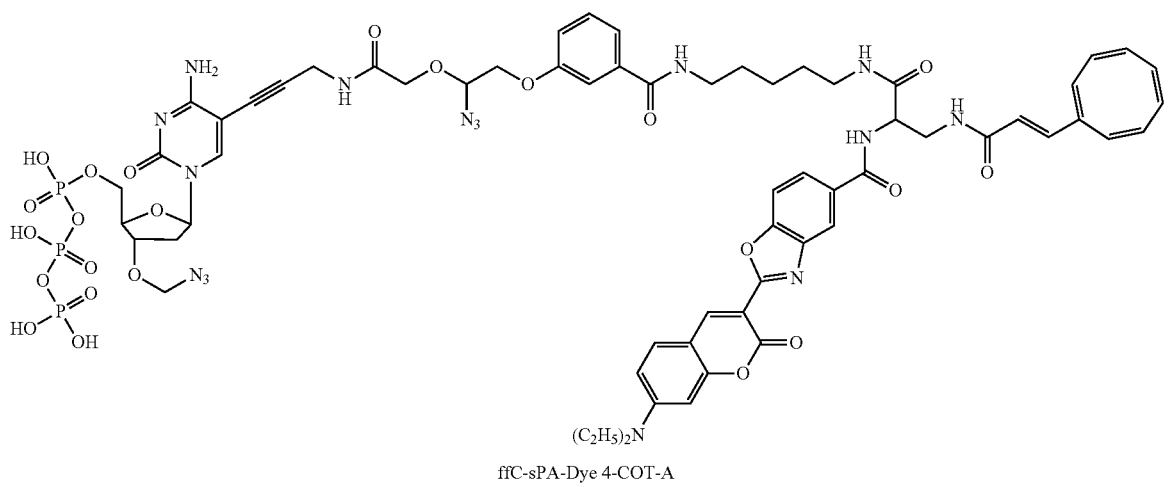

ffC-sPA-Dye 4-COT-A

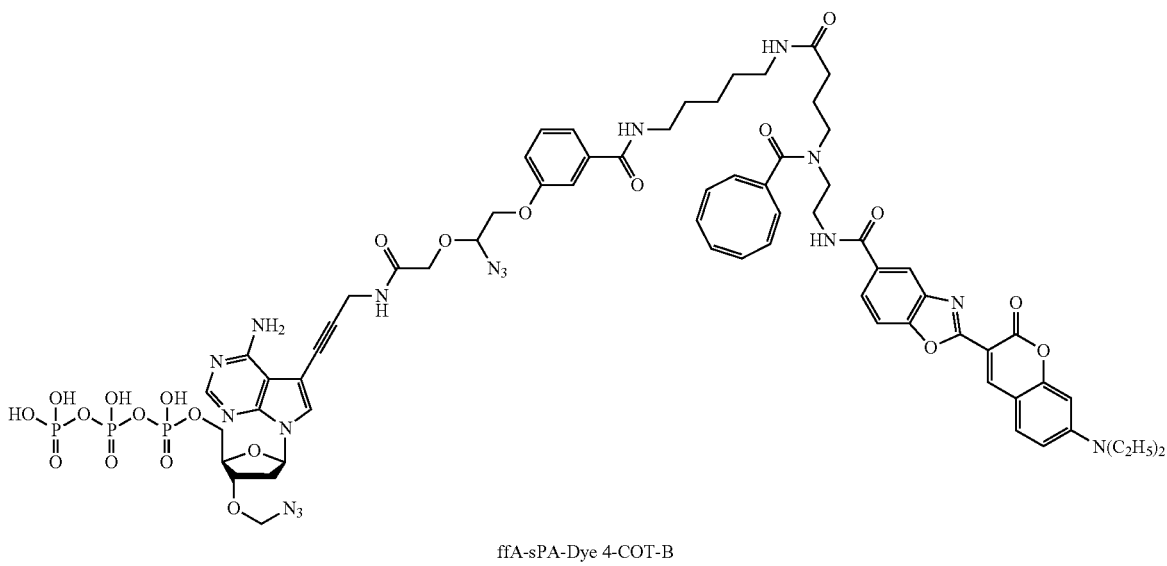

ffA-sPA-Dye 4-COT-B

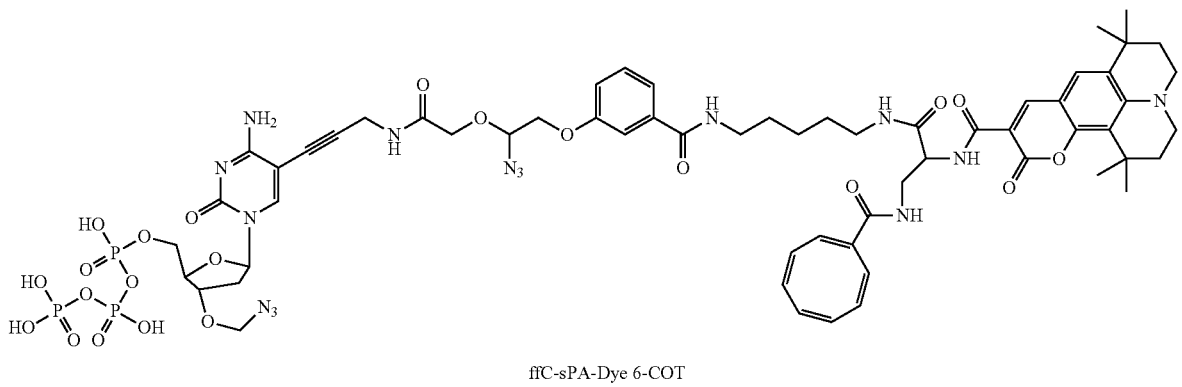

ffC-sPA-Dye 6-COT

Following the similar procedure described above, Dye-6-COT (16 µmol) in DMA (0.5 mL) was treated with TSTU (5.3 mg, 17.6 µmol) and DIPEA (17 µL, 100 mol), followed by dCTP-sPA (10 µmol) in 0.1 M TEAB (50 µL), and Et₃N (10 µL) and stirred at room temperature for 4 h. The crude residue was purified using reverse phase prep HPLC (YMC column, 10 mL/min, 45-65% MeCN/0.1M TEAB) to afford ffC-sPA-Dye 6-COT. Yield 40%. Absorption (maximum 455 nm) and fluorescence spectra (maximum 493 nm) were measured in USM.

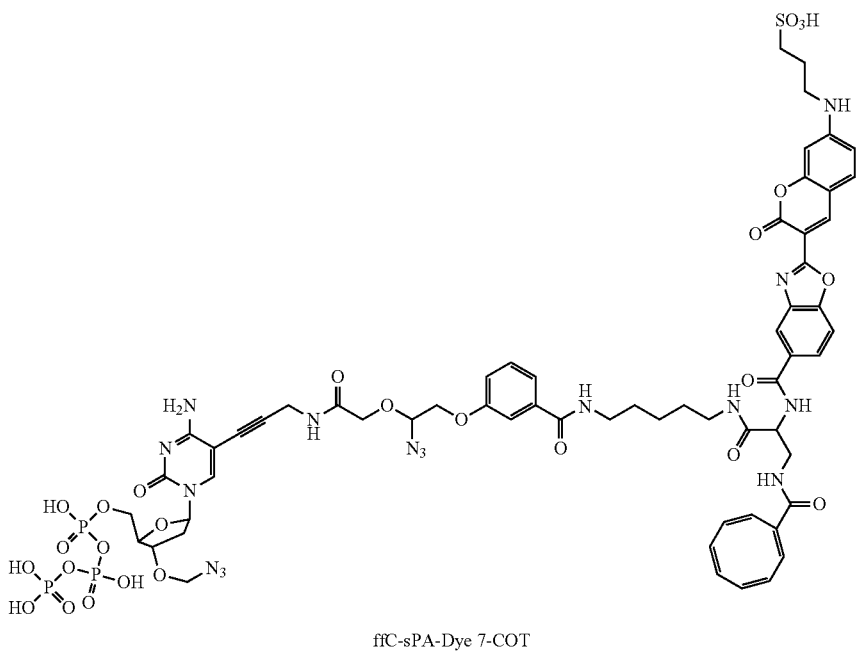 [SMILES: [N-]=[N+]=NCOC1CC(n2cc(C#CCNC(=O)COC(COc3cccc(C(=O)NCCCCCNC(=O)C(CNC(=O)C4=C/C=C\C=C/C=C\4)NC(=O)c4ccc5oc(-c6cc7ccc(NCCCS(=O)(=O)O)cc7oc6=O)nc5c4)c3)N=[N+]=[N-])c(N)nc2=O)OC1COP(=O)(O)OP(=O)(O)OP(=O)(O)O]

ffC-sPA-Dye 7-COT

Dye-7-COT (11.3 µmol) in DMA (0.5 mL) was treated with TSTU (3.8 mg, 12.4 µmol) and DIPEA (17 µL, 100 mol), followed by dCTP-sPA (11.3 µmol) in 0.1 M TEAB (50 µL), and Et₃N (10 µL) and stirred at RT for 4 h. The crude residue was purified using reverse phase prep HPLC to afford ffC-sPA-Dye 7-COT. Yield: 40%. Absorption (maximum 448 nm) and fluorescence spectra (maximum 488 nm) were measured in USM.

Figures 4A, 4B:
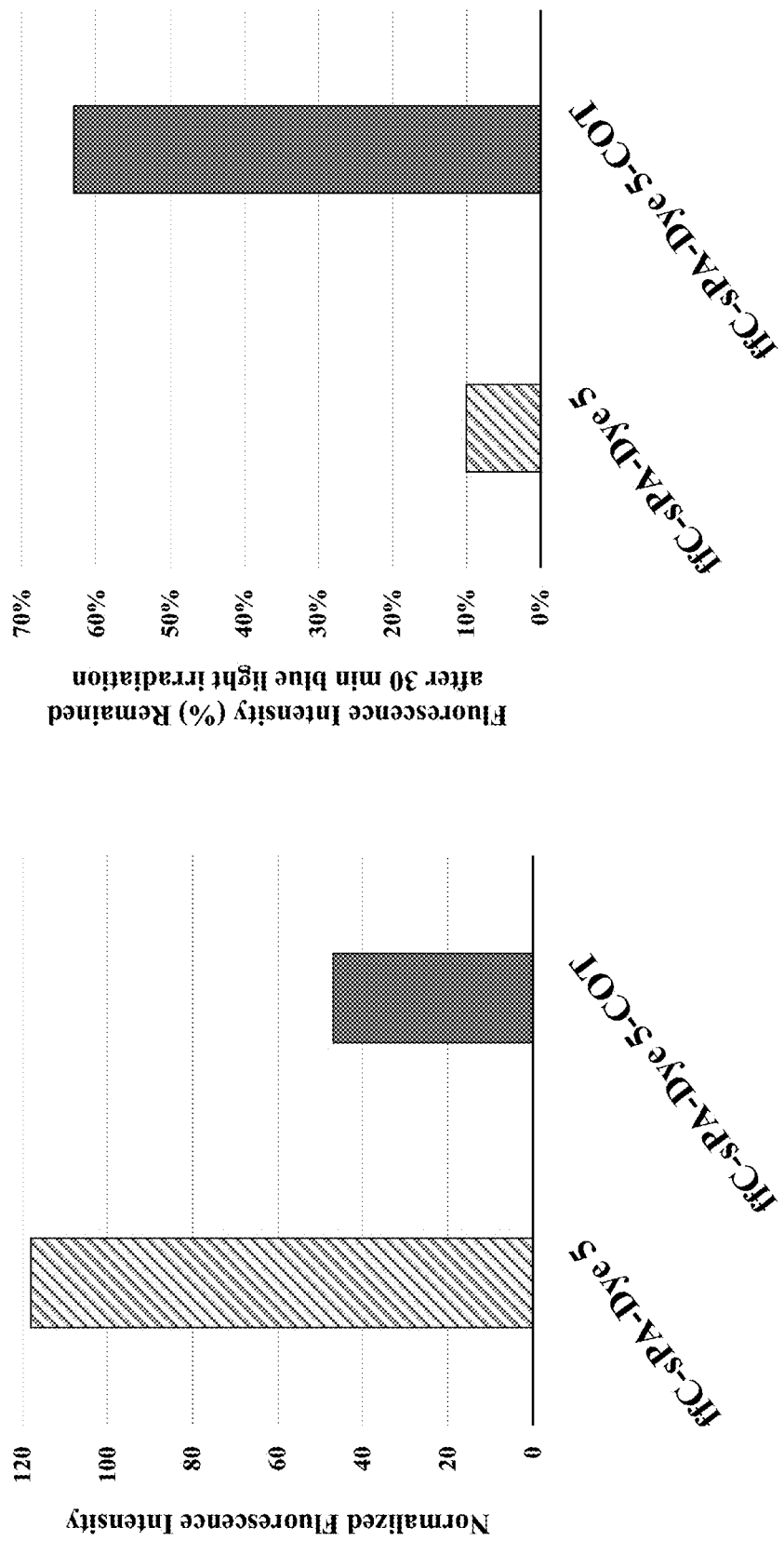
FIG. 4A illustrates the normalized fluorescent intensity of a labeled nucleotide, as compared to the normalized fluorescent intensity of the same labeled nucleotide comprising a covalently bonded COT moiety, in a standard detection solution.
FIG. 4B illustrates the photobleaching rate of the two labeled nucleotides in FIG. 4A after 30 minutes of LED irradiation in the solution.

The photobleaching rate of the ffC-sPA-Dye 5 and its corresponding dye containing of COT moiety (ffC-sPA-Dye 5-COT) were tested in a detection solution containing 10 mM cyclooctatetraene and 0.25 mM quercetin ("COT mix") against a control detection solution (USM). The normalized fluorescent intensity (1 mol, Excitation at 450 nm, PMT 600V) and the percentage remained fluorescent intensity after 30 minutes of blue LED light irradiation were measured and the results are shown in FIG. 4A and FIG. 4B respectively. FIG. 4A indicate that the blue fluorescent intensity was quenched 60% by the covalently bonded COT moiety. However, a substantial improvement of photo-stability while irradiated with blue LED light in the solution. after 30 min irradiation, there was only 10% fluorescent signal left in ffC-sPA-Dye 5 and 63% signal left in ffC-sPA-Dye 5-COT (FIG. 4B).

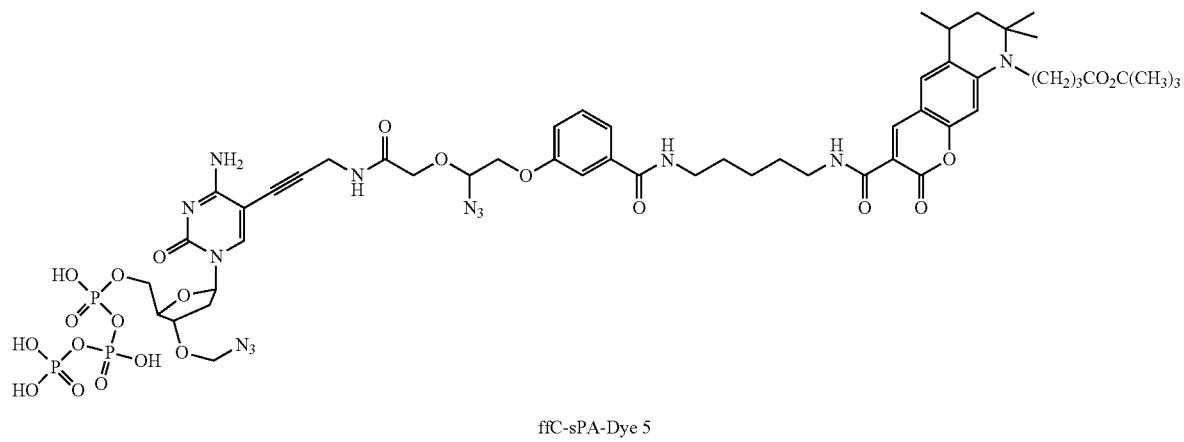

ffC-sPA-Dye 5

Figure 5A:
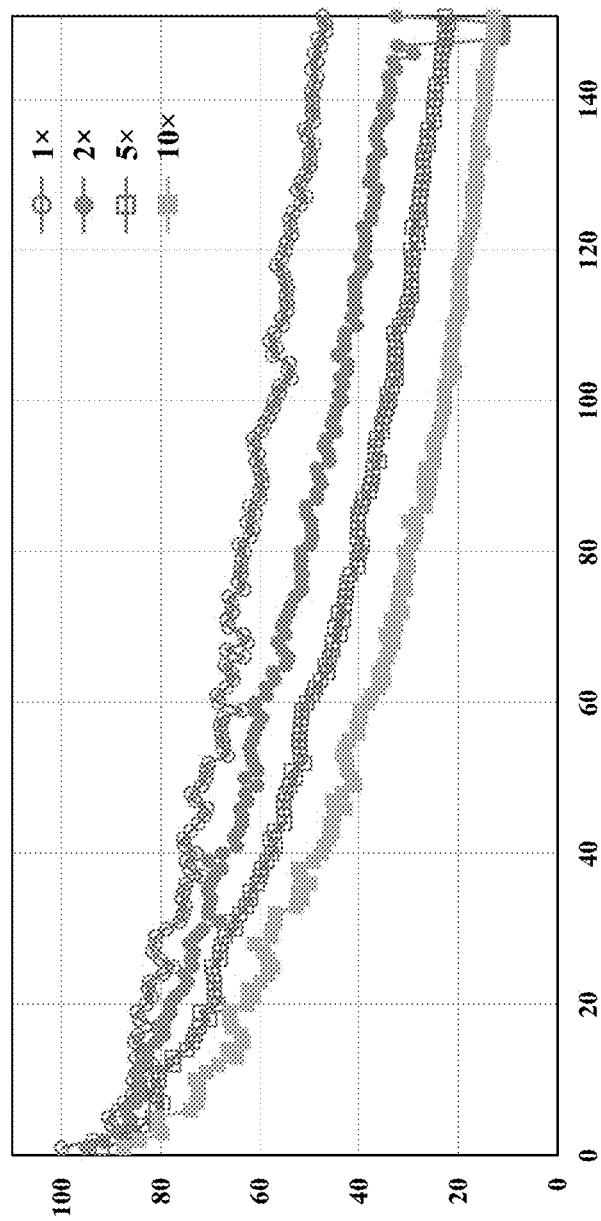
FIGS. 5A-5B illustrate the fluorescent signal decay of a labeled nucleotide and the same labeled nucleotide with a covalently bonded COT moiety respectively, with different light exposure (at 1 time, 2 times, 5 times and 10 times) after 150 cycles of sequencing run.
Figure 5B:
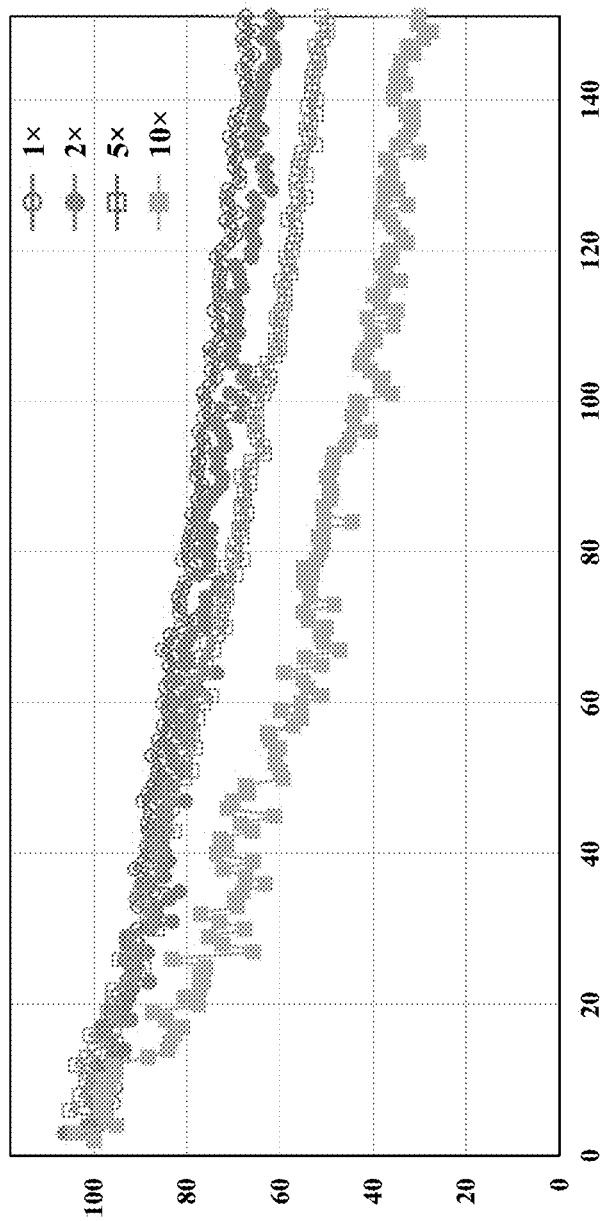

Sequencing run on the MiSeq® platform also showed substantial improvement of signal decay rate with ffC-sPA-Dye 5-COT (FIG. 5B) as compared to ffC-sPA-Dye 5 (FIG. 5A) after 150 cycles run with blue/green light exposure at four different intensities (1, 2 times, 5 times, or 10 times). The results demonstrate that COT moiety has reduced or prevented DNA damage caused by light irradiation.

Figure 6A:
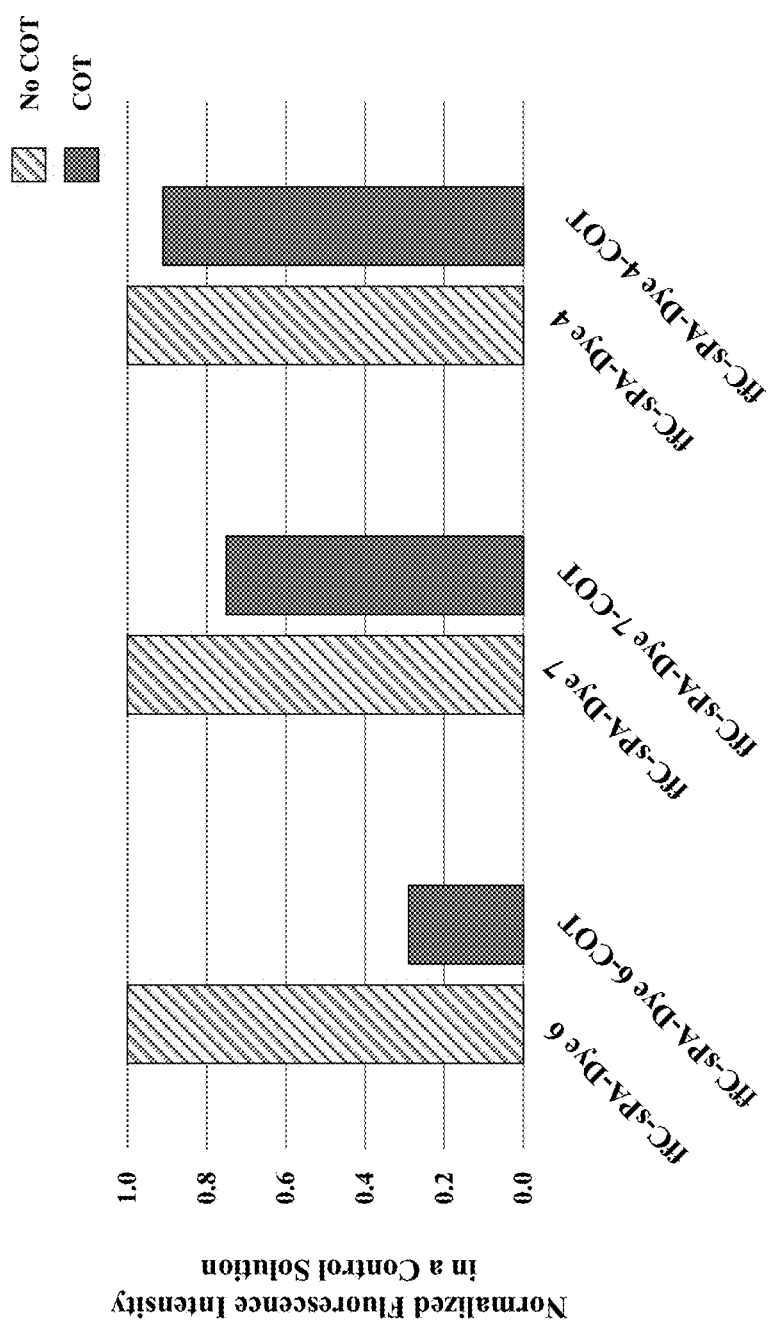
FIG. 6A illustrates the normalized fluorescent intensity of three labeled nucleotides, as compared to the normalized fluorescent intensity of the same three labeled nucleotides each comprising a covalently bonded COT moiety, in a standard detection solution.
Figure 6B:
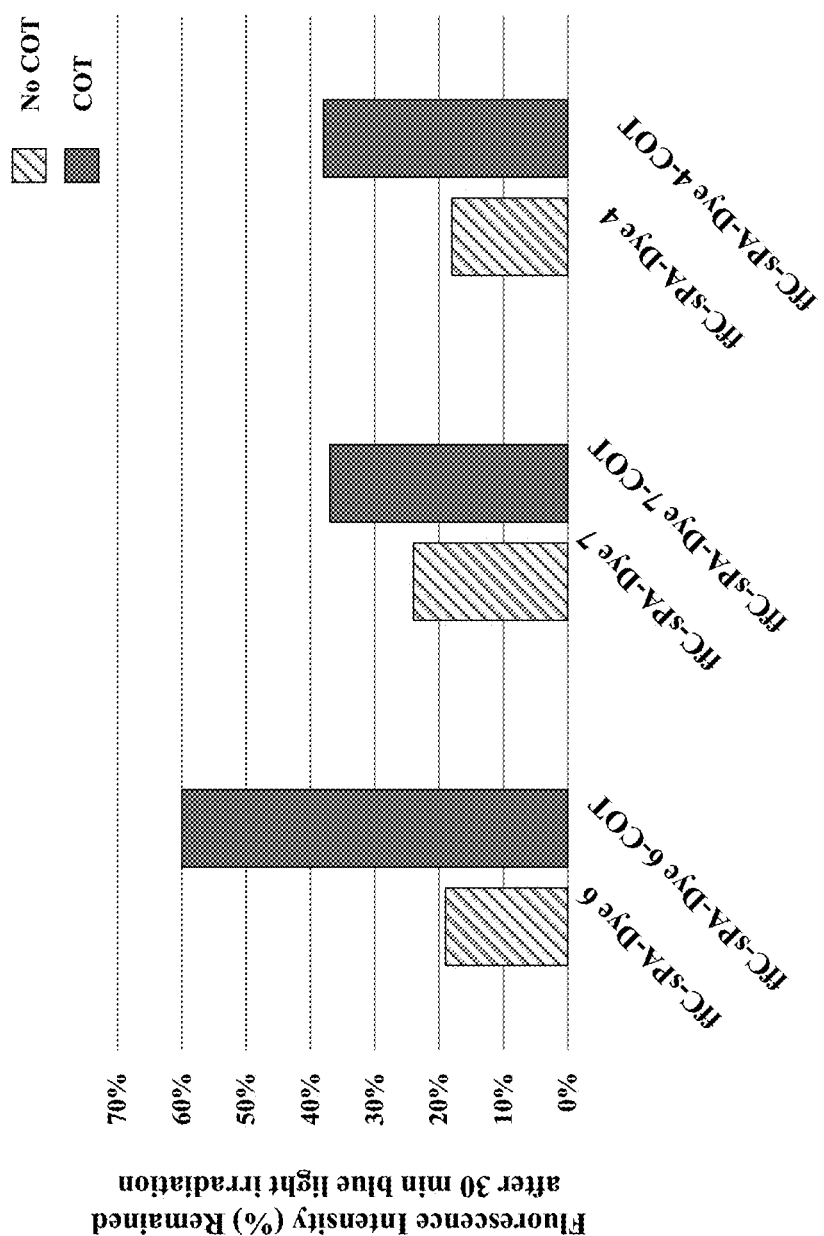
FIG. 6B illustrates the photobleaching rate of the six labeled nucleotides described in FIG. 6A after 30 minutes of LED irradiation in the solution.

As described above, additional COT modified blue dyes Dye 4-COT, Dye 6-COT and Dye 7-COT were prepared from Compound 2. For each COT modified dye, the point of connection to a fully functionalized nucleotides (ffN) is through the carboxyl group (—COOH) of the dye. FIG. 6A illustrates the normalized fluorescent intensity of ffC-sPA-Dye 6-COT, ffC-sPA-Dye 7-COT and ffC-sPA-Dye 4-COT (dye concentration 1 mol, Excitation at 450 nm, PMT 600V) in a standard detection solution (USM) as compared to the none-COT containing equivalent. FIG. 6A illustrates the effect of COT moiety on fluorescence of the dye and dye structure dependence of the quenching effect. FIG. 6B illustrates photo protecting effects of the COT moiety that were observed in all three blue dyes tested as the percentage remained fluorescent intensity of the dyes after 30 minutes of blue LED light irradiation.

| Set (n) | Photo-bleaching (% Int. 10x/1x) |
| --- | --- |
| C-Dye 7 | 60% |
| C-Dye 7-COT | 87% |
| C-Dye 4 | 63% |
| C-Dye4-COT | 86% |

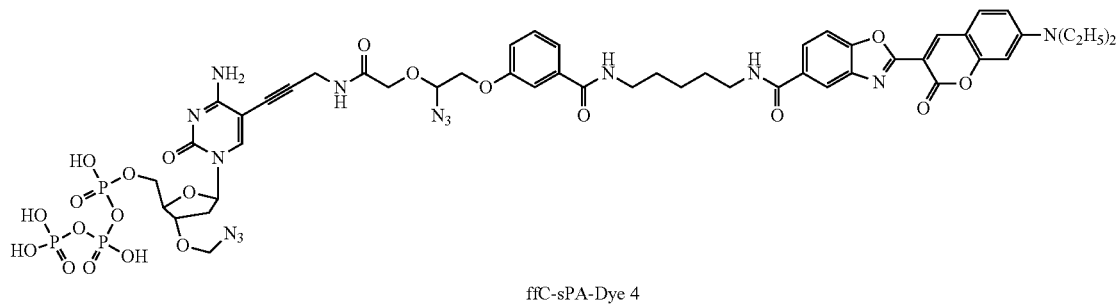

ffC-sPA-Dye 4

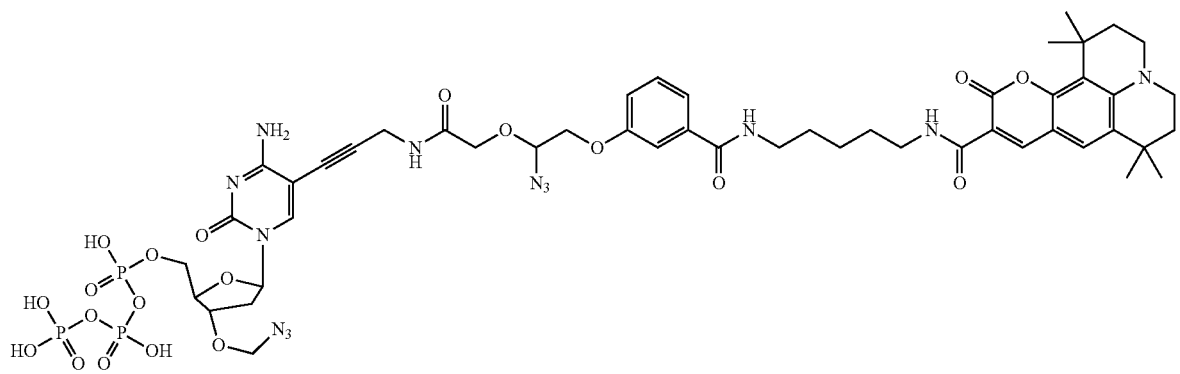

ffC-sPA-Dye 6

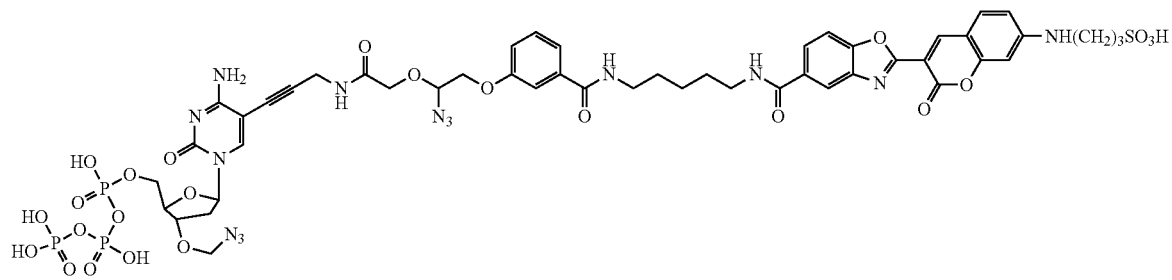

ffC-sPA-Dye 7

Figure 7:
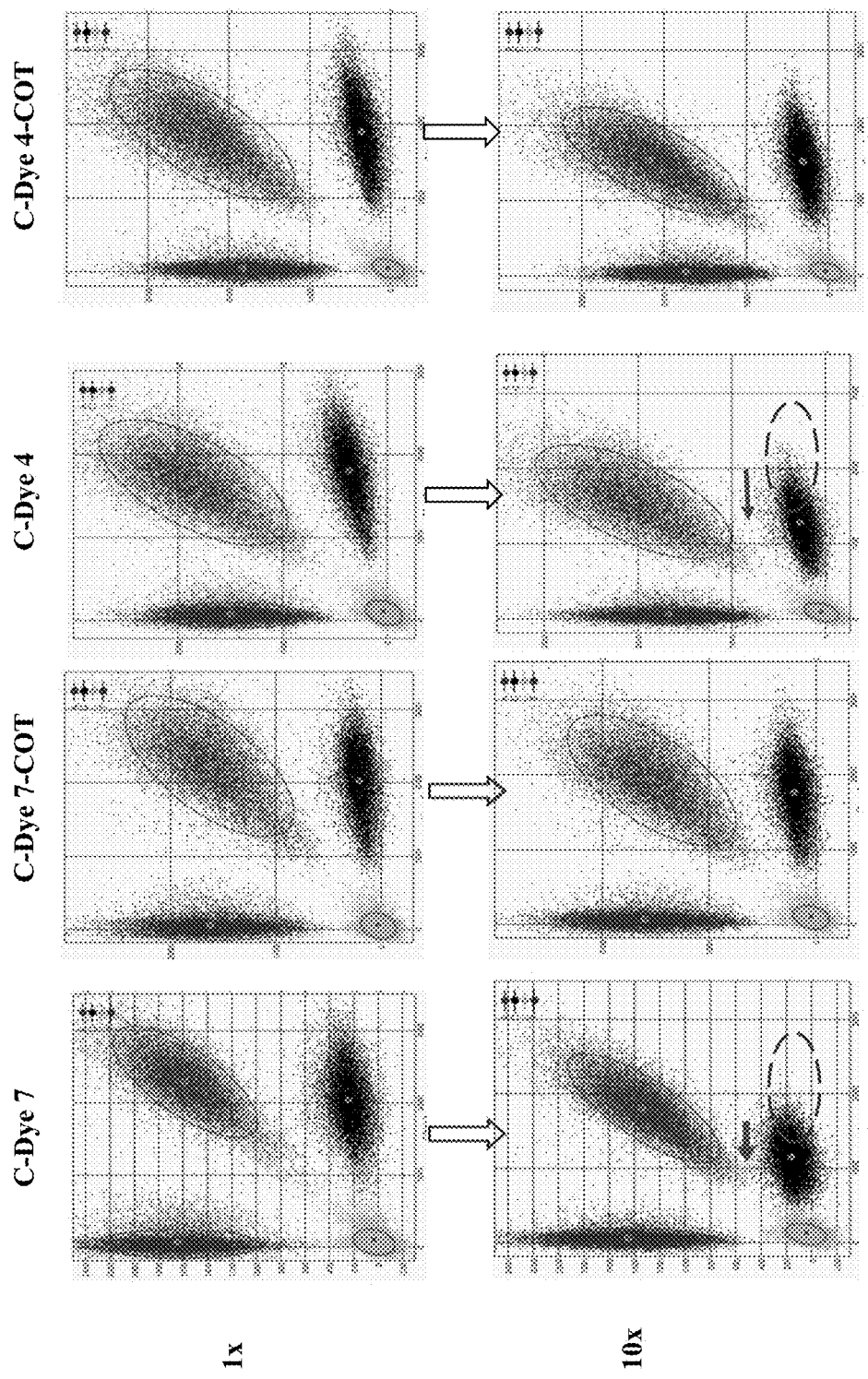
FIG. 7 illustrates the scatter plots of two labeled nucleotides, as compared to the scatter plots of the same two labeled nucleotides each comprising a covalently bonded COT moiety when the labeled nucleotides are exposed to 1 time and 10 times of blue light irradiation.

Furthermore, similar quenching and dye photostability were observed on the MiSeq® platform using a blue light irradiation. In FIG. 7, the black cloud (right bottom quadrant) at x-axis in the scatter plots indicated the intensity of fluorescent signals of labeled C-nucleotide. Dye photobleaching was measured by comparing the intensity change under blue light exposure at 1 time and 10 times intensity and the results are summarized in the table below.

Figure 8:
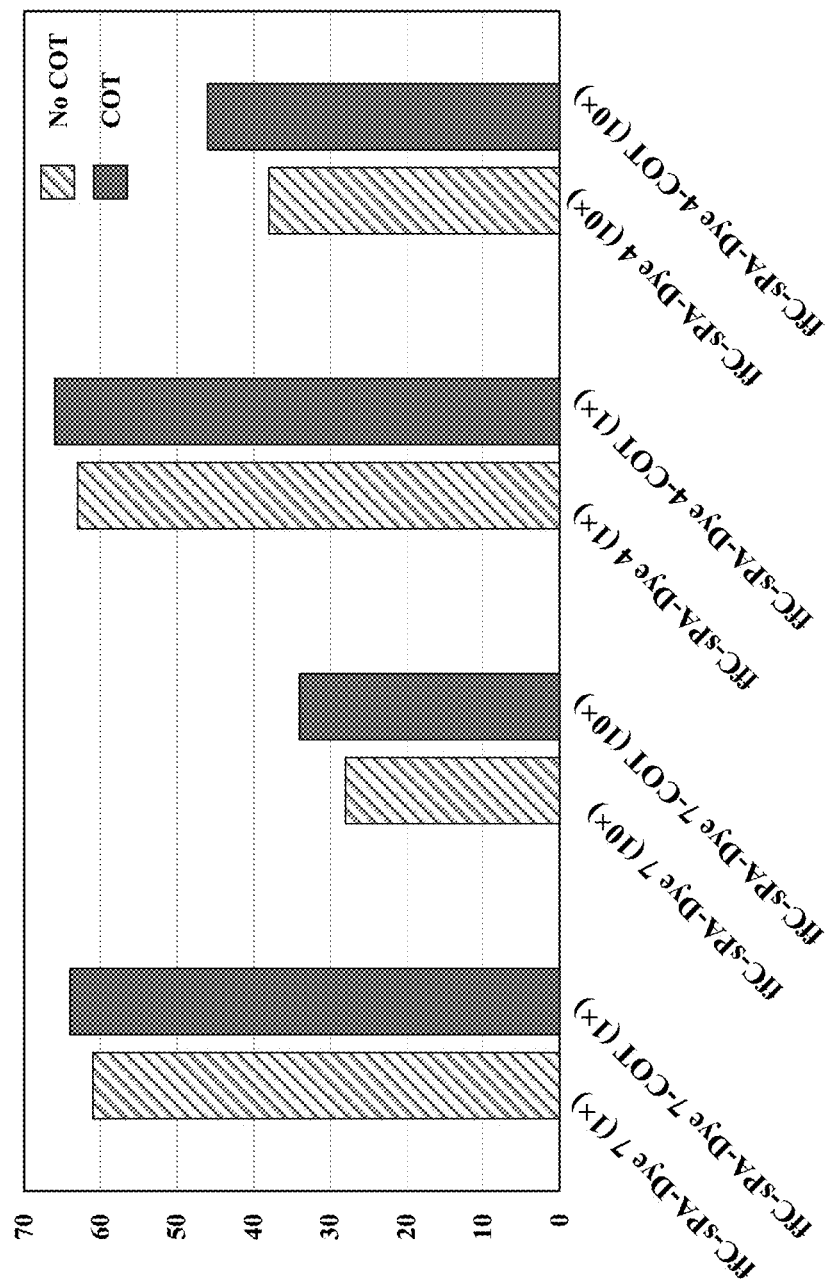
FIG. 8 illustrates the photobleaching rate of the four labeled nucleotides described in FIG. 7 when exposed to 1 time and 10 times of blue light irradiation.

As shown in FIG. 8, the signal decay rate (% of signal intensity at $150^{th}$ cycle of sequencing compared to first cycle) has also been improved in the COT modified dyes (ffC-sPA-Dye 4-COT and ffc-sPA-Dye 7-COT), which indicated the photo protective effect of the COT moiety on the DNA damage induced by the blue LED/laser during sequencing.

In conclusion, the covalent attachment of COT moiety to blue dyes has demonstrated a protective effect on both photo-bleaching and DNA damage.

What is claimed is:

1. A fluorescent compound comprising a photo-protecting cyclooctatetraene moiety, wherein the photo-protecting cyclooctatetraene moiety comprises the structure of formula (I):

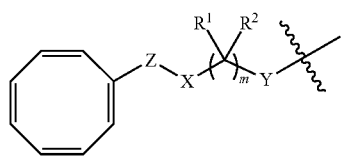

wherein:
each of $R^1$ and $R^2$ are each independently selected from the group consisting of H, hydroxyl, halogen, azido, thiol, nitro, cyano, unsubstituted and substituted amino, carboxyl, —C(O)OR$^5$, —C(O)NR$^6$R$^7$, unsubstituted and substituted $C_{1-6}$ alkyl, unsubstituted and substituted $C_{1-6}$ alkoxy, unsubstituted and substituted $C_{1-6}$ haloalkyl, unsubstituted and substituted $C_{1-6}$ haloalkoxy, unsubstituted and substituted $C_{2-6}$ alkenyl, unsubstituted and substituted $C_{2-6}$ alkynyl, unsubstituted and substituted $C_{6-10}$ aryl, unsubstituted and substituted $C_{7-14}$ aralkyl, unsubstituted and substituted $C_{3-7}$ carbocyclyl, unsubstituted and substituted 5 to 10 membered heteroaryl, and unsubstituted and substituted 3 to 10 membered heterocyclyl;

X is —C(=O)—NR$^4$;

Y is selected from the group consisting of —O—, —S—, —NR$^3$—, —C(=O)—, —C(=O)—O—, —C(=O)—NR$^4$—, —S(O)$_2$—, —NR$^3$—C(=O)—NR$^4$, —NR$^3$—C(=S)—NR$^4$—, and unsubstituted and substituted heteroalkylene where at least one carbon atom is replaced with O, S, or N;

Z is absent, unsubstituted or substituted $C_{2-6}$ alkenylene, or unsubstituted or substituted $C_{2-6}$ alkynylene;

each of $R^3$ and $R^4$ is independently H, unsubstituted or substituted $C_{1-6}$ alkyl, or unsubstituted or substituted $C_{6-10}$ aryl;

$R^5$ is unsubstituted or substituted $C_{1-6}$ alkyl, unsubstituted or substituted $C_{6-10}$ aryl, unsubstituted or substituted $C_{7-14}$ aralkyl, unsubstituted or substituted $C_{3-7}$ carbocyclyl, unsubstituted or substituted 5 to 10 membered heteroaryl, or unsubstituted or substituted 3 to 10 membered heterocyclyl;

each of $R^6$ and $R^7$ is independently H, unsubstituted or substituted $C_{1-6}$ alkyl, unsubstituted or substituted $C_{6-10}$ aryl, unsubstituted or substituted $C_{7-14}$ aralkyl, unsubstituted or substituted $C_{3-7}$ carbocyclyl, unsubstituted or substituted 5 to 10 membered heteroaryl, or unsubstituted or substituted 3 to 10 membered heterocyclyl;

the carbon atom to which $R^1$ and $R^2$ are attached in

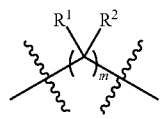

is optionally replaced with O, S, or N, provided that when said carbon atom is replaced with O or S, then $R^1$ and $R^2$ are both absent; when said carbon atom is replaced with N, then $R^2$ is absent; and m is an integral number between 1 and 10;

provided that the fluorescent compound is not a cyanine dye, and wherein the fluorescent compound is excitable by a light source having a wavelength between about 350 nm to about 500 nm.

2. The fluorescent compound of claim 1, wherein Z is absent.

3. The fluorescent compound of claim 1, wherein Z is unsubstituted $C_{2-6}$ alkenylene.

4. The fluorescent compound of claim 1, wherein $R^4$ is H or $C_{1-6}$ alkyl substituted with amino, —SO$_3$H, —SO$_3^-$, carboxyl, —C(O)OR$^5$, or —C(O)NR$^6$R$^7$.

5. The fluorescent compound of claim 1, wherein Y is —C(=O)O—, —NR$^3$— or —S(O)$_2$—.

6. The fluorescent compound of claim 5, wherein Y is —NR$^3$— and $R^3$ is H or $C_{1-6}$ alkyl substituted with amino, carboxyl, —SO$_3$H, —SO$_3^-$—O—SO$_3^-$, —C(O)OR$^5$, or —C(O)NR$^6$R$^7$.

7. The fluorescent compound of claim 1, wherein the photo-protecting moiety comprises the structure of formula (Ia), (Ib), (Ic) or (Id):

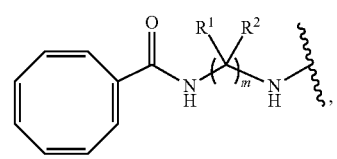

(Ia)

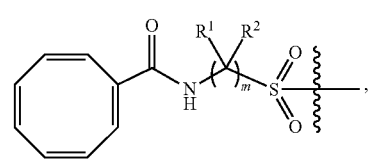

(Ib)

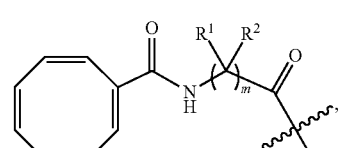

(Ic)

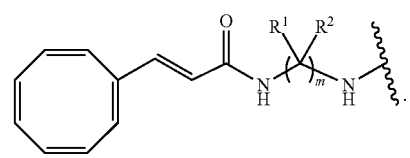

(Id)

8. The fluorescent compound of claim 1, wherein at least one of $R^1$ and $R^2$ is hydrogen, or both $R^1$ and $R^2$ is hydrogen.

9. The fluorescent compound of claim 1, wherein $R^1$ is H and $R^2$ is amino or carboxyl.

10. The fluorescent compound of claim 1, wherein at least one carbon atom
to which $R^1$ and $R^2$ are attached in

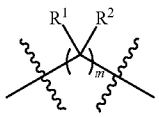

is replaced with O, S, or N, and wherein m is 1, 2, 3, 4, 5 or 6.

11. The fluorescent compound of claim 1, wherein m is 2, 3, 4, 5 or 6, and each one of $R^1$ and $R^2$ is hydrogen.

12. The fluorescent compound of claim 1, wherein m is 2, 3, 4, 5, or 6 wherein each of $R^1$ and $R^2$ is hydrogen in

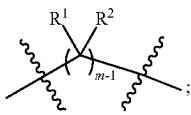

and wherein $R^1$ is H, and $R^2$ is amino, carboxyl, —C(O)$OR^5$, or —C(O)$NR^6R^7$ in the remaining

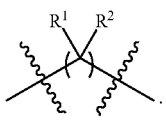

13. The fluorescent compound of claim 12, wherein $R^5$ is $C_{1-6}$ alkyl or unsubstituted phenyl, and wherein one or both of $R^6$ and $R^7$ is H or $C_{1-6}$ alkyl substituted with carboxyl, amino, —$SO_3H$, or —$SO_3^-$.

14. The fluorescent compound of claim 1, wherein the photo-protecting moiety comprises the structure:

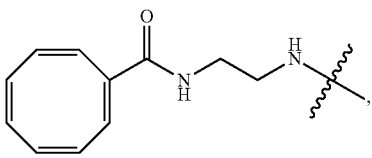

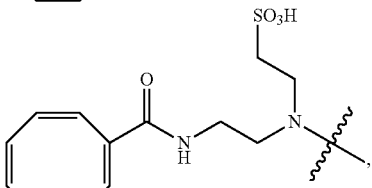

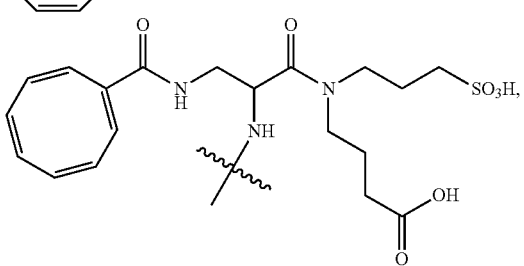

-continued

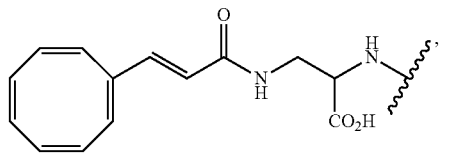

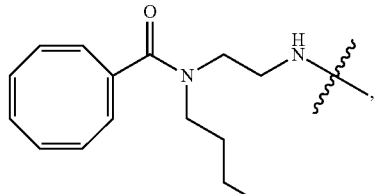

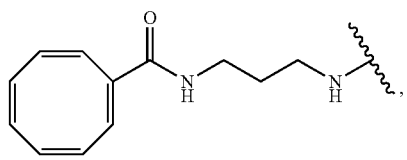

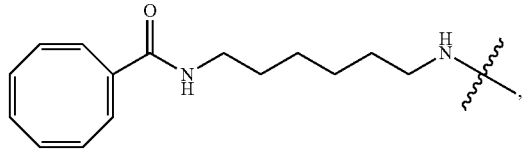

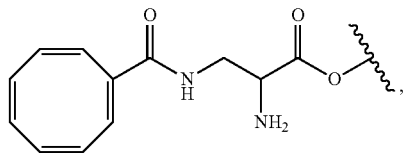

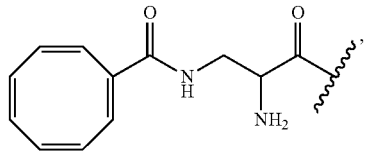

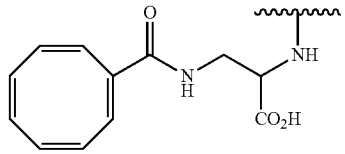

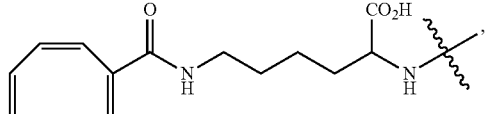

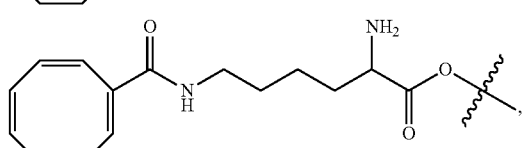

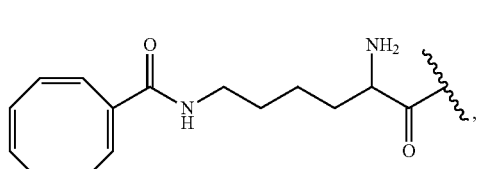

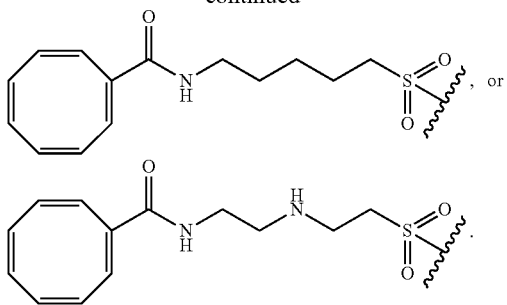

, or

15. The fluorescent compound of claim 1, wherein the fluorescent compound is excitable by a light source having a wavelength between about 420 nm and about 480 nm, or between about 450 nm and about 460 nm.

16. A nucleoside, nucleotide or oligonucleotide labeled with a fluorescent compound of claim 1.

17. A method of protecting a fluorescent dye from photobleaching, comprising covalently attaching the fluorescent dye to a photo-protecting cyclooctatetraene moiety comprising the structure of formula (I) according to claim 1.

18. A method of protecting a nucleoside or nucleotide from light-induced degradation, comprising covalently attaching the nucleoside or nucleotide to a fluorescent compound of claim 1.

19. A method of reducing or preventing light-induced degradation of nucleic acids during a nucleic acid sequencing reaction, comprising:

(a) incorporating a nucleotide into a copy polynucleotide strand complementary to at least a portion of a template polynucleotide strand, wherein the nucleotide comprises a 3' blocking group and is labeled with a fluorescent compound of claim 1;

(b) detecting the identity of the nucleotide incorporated into the copy strand in the presence of a first buffer composition;

(c) chemically removing the label and the 3' blocking group from the nucleotide incorporated into the copy polynucleotide strand; and (d) washing the chemically removed label and the 3' blocking group away from the copy strand with a wash solution.

20. A kit for use with a sequencing apparatus, comprising a plurality of chambers containing a plurality of compositions, wherein each chamber contains a single composition, wherein the plurality of compositions comprise:

reagents for incorporating a nucleotide into a copy polynucleotide strand complementary to at least a portion of a template polynucleotide strand, wherein the nucleotide comprises a 3' blocking group and is labeled with a fluorescent compound of claim 1;

a buffer composition comprising at least one antioxidant;

reagents for chemically removing a label and blocking moiety from the blocked, labeled nucleotide incorporated into the copy strand; and a wash solution.

\* \* \* \* \*

UNITED STATES PATENT AND TRADEMARK OFFICE
CERTIFICATE OF CORRECTION

PATENT NO. : 11,597,969 B2
APPLICATION NO. : 17/103169
DATED : March 7, 2023
INVENTOR(S) : Xiaolin Wu et al.

It is certified that error appears in the above-identified patent and that said Letters Patent is hereby corrected as shown below:

In the Specification

Column 10, Line 40, delete "isoquinlinyl," and insert -- isoquinolinyl, --.

Column 12, Line 22, delete "$R_b$" and insert -- $R_B$ --.

Column 19, Line 44, delete "—O—SO$_3$ $^-$" and insert -- —O—SO$_3$ $^-$, --.

Column 22, Lines 53-58 (approx.), delete " " and insert -- 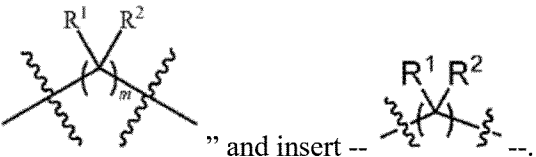 --.

Column 22, Line 60, after "the remaining" insert -- 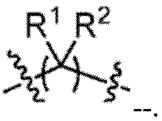 --.

Column 22, Lines 62-67 (approx.), delete " 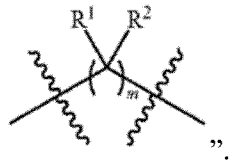 ".

Column 28, Line 15, delete "—SO$^3$H," and insert -- —SO$_3$H, --.

Column 28, Line 24, delete "—SO$^3$H," and insert -- —SO$_3$H, --.

Column 29, Line 9, delete "—(CH$_2$)$_q$—C(O)NR$^d$R$^c$," and insert -- —(CH$_2$)$_q$—C(O)NR$^d$R$^e$, --.

Signed and Sealed this
Seventeenth Day of October, 2023

Katherine Kelly Vidal
*Director of the United States Patent and Trademark Office*

CERTIFICATE OF CORRECTION (continued)
U.S. Pat. No. 11,597,969 B2

Column 34, Lines 1-9, delete " 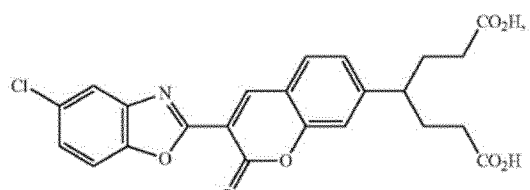 " and insert

-- 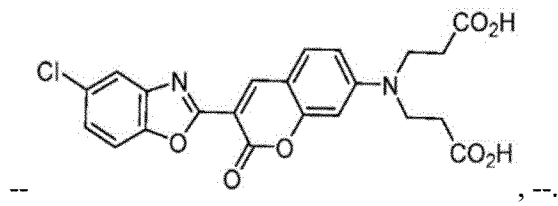 , --.

Column 38, Lines 1-10, delete " 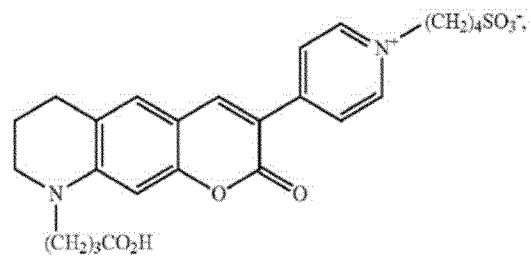 " and insert

-- 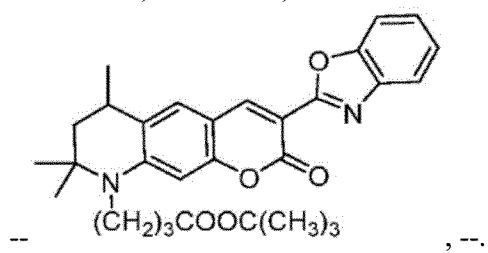 , --.

Column 41, Lines 36-44 (approx.), delete " 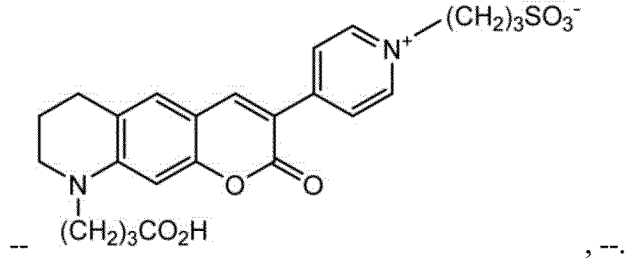 " and insert

-- 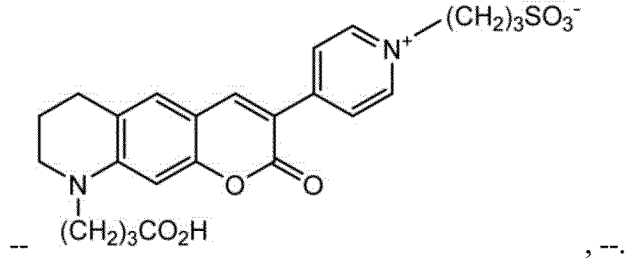 , --.

CERTIFICATE OF CORRECTION (continued)
U.S. Pat. No. 11,597,969 B2

Column 44, Lines 42-54 (approx.), delete " 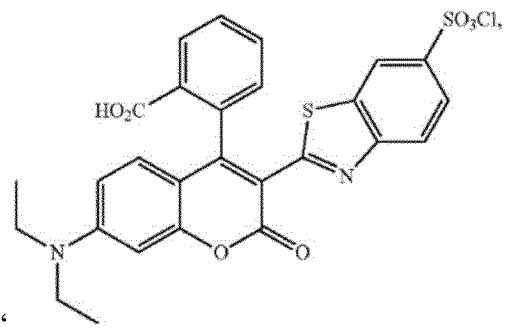 " and insert -- 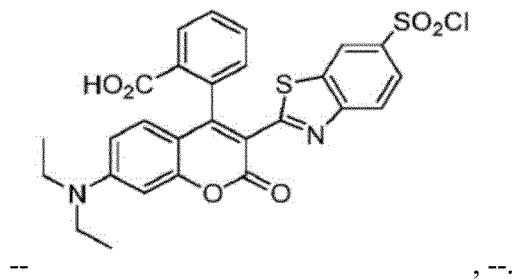 , --.

Column 44, Lines 55-67 (approx.), delete " 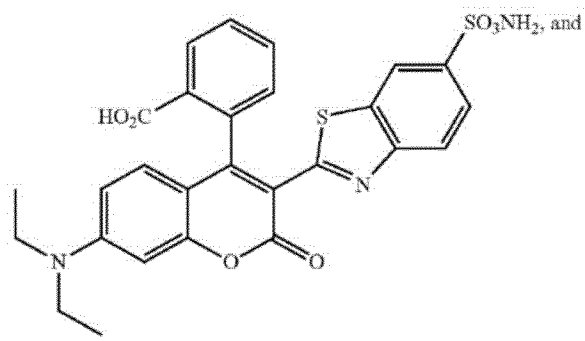 " and insert -- 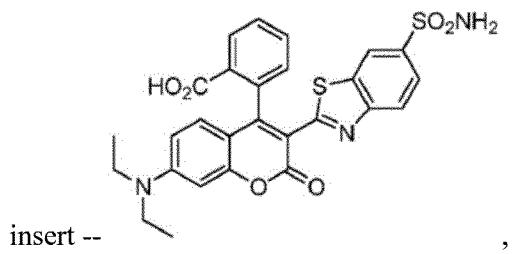 , and --.

Column 47, Line 44, delete "$R^{1a}$" and insert -- $R^{3a}$ --.

Column 50, Lines 14-18 (approx.), delete " 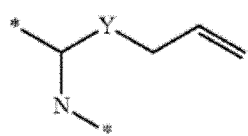 " and insert -- 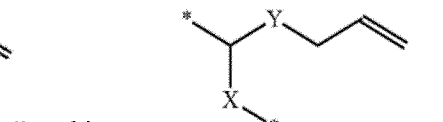 --.

CERTIFICATE OF CORRECTION (continued)
U.S. Pat. No. 11,597,969 B2

Column 56, Lines 27-36 (approx.), delete " 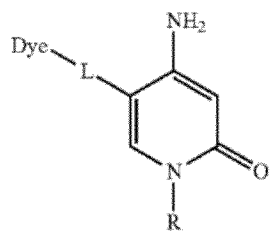 " and insert

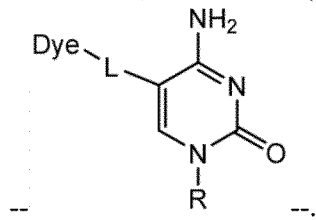 --.

Column 58, Lines 18-25 (approx.), delete " 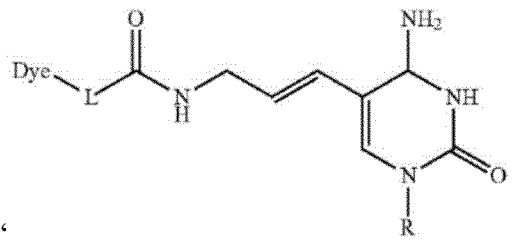 " and insert

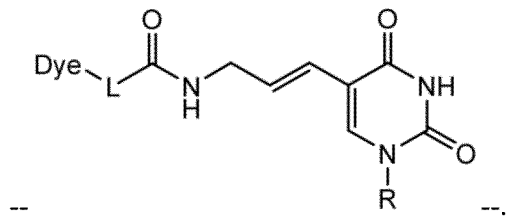 --.

Column 61-62, Line 3 (in structure), delete

" 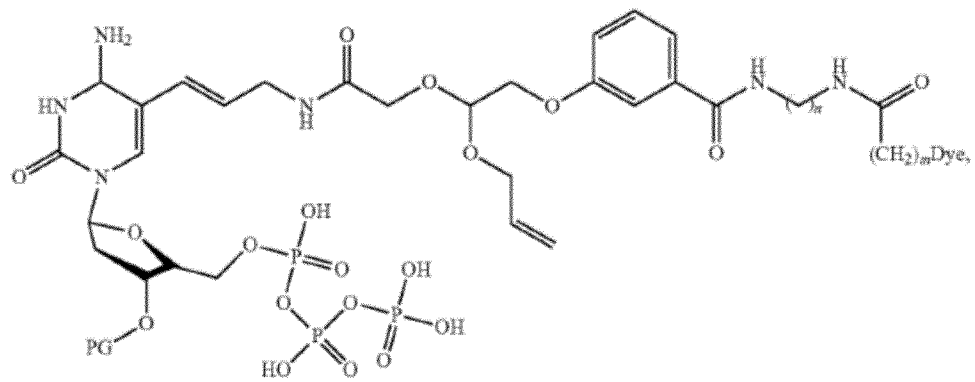 " and insert

CERTIFICATE OF CORRECTION (continued)
U.S. Pat. No. 11,597,969 B2

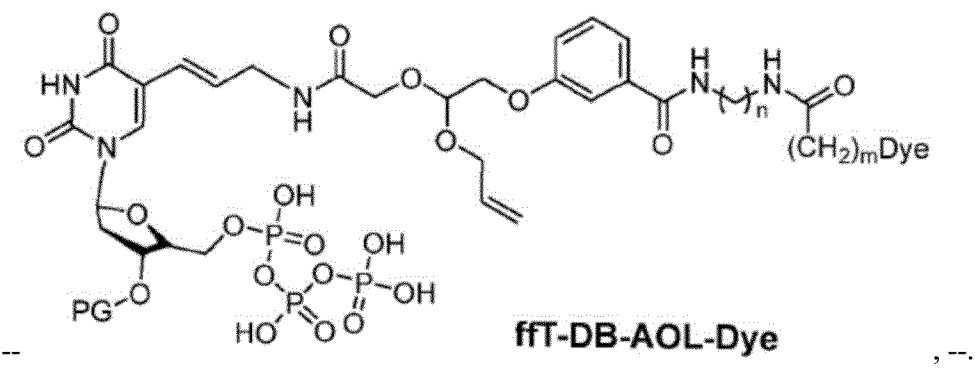

-- ffT-DB-AOL-Dye , --.

Column 77, Line 24, delete "1,3,5,7-cyclooktotetraenyl" and insert -- 1,3,5,7-cyclooctatetraenyl --.

Column 77, Lines 29-34 (approx.), delete " 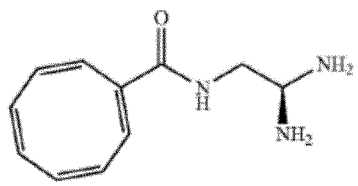 " and insert

-- 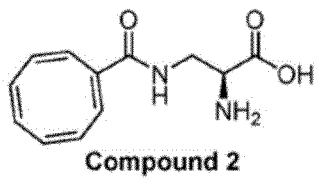 --.

Column 77-78, Line 65 (approx.), below

"  "

insert -- 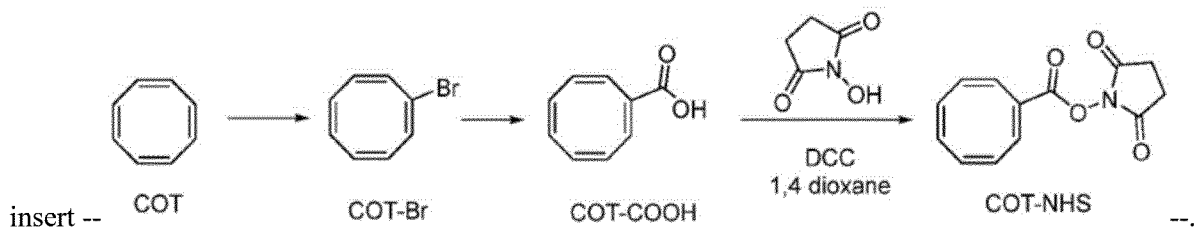 --.

Column 79, Line 41, delete "NH₄C₁" and insert -- NH₄Cl --.

Column 91, Line 3, delete "Succinimidoyl)" and insert -- Succinimidyl) --.

Column 96, Line 30 (approx.), delete "after" and insert -- After --.

Column 98, Line 7 (approx.), delete "C-Dye4-COT" and insert -- C-Dye 4-COT --.

Column 98, Line 7 (approx.), delete "C-Dye4-COT" and insert -- C-Dye 4-COT --.

In the Claims

Column 100, Line 17 (approx.), Claim 4, delete "—$SO_3$ —" and insert -- —$SO_3^-$ --.

Column 100, Line 19 (approx.), Claim 5, delete "—$S(O)_2$ " and insert -- —$S(O)_2$— --.

Column 100, Line 24 (approx.), Claim 6, delete "—$SO_3^-$ —O—$SO_3$ —," and insert -- —$SO_3^-$ , —O—$SO_3^-$, --.

Column 101, Line 36 (approx.), Claim 13, after "unsubstituted" insert -- or substituted --.

Column 101, Line 38 (approx.), Claim 13, delete "—$SO_3$ —" and insert -- —$SO_3^-$ --.